United States Patent
Edwards et al.

(10) Patent No.: US 6,273,886 B1
(45) Date of Patent: Aug. 14, 2001

(54) INTEGRATED TISSUE HEATING AND COOLING APPARATUS

(75) Inventors: Stuart Edwards, Portola Valley; John Gaiser, Mountain View; David Utley, San Carlos; Scott West, Livermore; Jay Chin, Fremont, all of CA (US)

(73) Assignee: Curon Medical, Inc., Sunnyvale, CA (US)

( * ) Notice: Subject to any disclaimer, the term of this patent is extended or adjusted under 35 U.S.C. 154(b) by 0 days.

(21) Appl. No.: 09/305,079

(22) Filed: May 4, 1999

Related U.S. Application Data

(63) Continuation-in-part of application No. 09/026,296, filed on Feb. 19, 1998, now Pat. No. 6,009,877.

(51) Int. Cl.[7] ..................................... A61B 18/04
(52) U.S. Cl. ........................... 606/34; 607/101; 607/105; 606/41
(58) Field of Search ................... 606/31, 32, 34, 606/41, 42, 45–50; 607/101–105

(56) References Cited

U.S. PATENT DOCUMENTS

| | | |
|---|---|---|
| 1,798,902 | 3/1931 | Raney . |
| 3,517,128 | 6/1970 | Hines . |
| 3,901,241 | 8/1975 | Allen, Jr. . |

(List continued on next page.)

FOREIGN PATENT DOCUMENTS

| | | |
|---|---|---|
| 43 03 882 | 2/1995 | (DE) . |
| 38 38 840 | 2/1997 | (DE) . |
| 0 139 607 | 5/1985 | (EP) . |
| 0 608 609 | 8/1994 | (EP) . |
| 91/01773 | 2/1991 | (WO) . |
| 92/10142 | 6/1992 | (WO) . |
| 93/08755 | 5/1993 | (WO) . |
| 94/10925 | 5/1994 | (WO) . |
| 94/21165 | 9/1994 | (WO) . |
| 94/21178 | 9/1994 | (WO) . |
| 94/22366 | 10/1994 | (WO) . |
| 94/26178 | 11/1994 | (WO) . |
| 95/18575 | 7/1995 | (WO) . |
| 95/19142 | 7/1995 | (WO) . |
| 95/25472 | 9/1995 | (WO) . |
| 96/00042 | 1/1996 | (WO) . |
| 96/16606 | 6/1996 | (WO) . |
| 96/29946 | 10/1996 | (WO) . |
| 97/06857 | 2/1997 | (WO) . |
| 97/32532 | 9/1997 | (WO) . |
| 97/43971 | 11/1997 | (WO) . |

OTHER PUBLICATIONS

Castell, D.O. "Gastroesophageal Reflux Disease: Current Strategies for Patient Management." Arch Fam Med. 5(4):221–7.

Dallemagne, B. et al., "Laparoscopic Nissen Fundoplication: Preliminary." Surgical Laparoscopy & Endoscopy. 1991 1(3): 138–43.

Hinder, R.A. et al., "The Technique of Laparoscopic Nissen Fundoplication." Surgical Laparoscopy & Endoscopy. 1992. 2(3): 265–272.

Karlstrom, L.H. et al. "Ectopic jejunal pacemakers and enterogastric reflux after Roux gastrectomy: Effect of intestinal pacing." Surgery 1989. 106(3): 486–495.

(List continued on next page.)

Primary Examiner—Michael Peffley
(74) Attorney, Agent, or Firm—Ryan Kromholz & Manion,S.C.

(57) ABSTRACT

Systems and methods integrate the control of an energy generator, to supply energy to an electrode structure to heat a tissue region, and the control of a pumping mechanism, to supply cooling fluid to control tissue temperature in the region.

52 Claims, 41 Drawing Sheets

U.S. PATENT DOCUMENTS

| | | |
|---|---|---|
| 4,011,872 | 3/1977 | Komiya . |
| 4,196,724 | 4/1980 | Wirt et al. . |
| 4,411,266 | 10/1983 | Cosman . |
| 4,423,812 | 1/1984 | Sato . |
| 4,532,924 | 8/1985 | Auth et al. . |
| 4,565,200 | 1/1986 | Cosman . |
| 4,705,041 | 11/1987 | Kim . |
| 4,901,737 | 2/1990 | Toone . |
| 4,906,203 | 3/1990 | Margrave et al. . |
| 4,907,589 | 3/1990 | Cosman . |
| 4,943,290 | 7/1990 | Rexroth et al. . |
| 4,947,842 | 8/1990 | Marchosky et al. . |
| 4,955,377 | 9/1990 | Lennox et al. . |
| 4,966,597 | 10/1990 | Cosman . |
| 4,976,711 | 12/1990 | Parins et al. . |
| 5,019,075 | 5/1991 | Spears et al. . |
| 5,035,696 | 7/1991 | Rydell . |
| 5,046,512 | 9/1991 | Murchie . |
| 5,047,028 | 9/1991 | Qian . |
| 5,057,107 | 10/1991 | Parins et al. . |
| 5,078,717 | 1/1992 | Parins et al. . |
| 5,083,565 | 1/1992 | Parins . |
| 5,084,044 | 1/1992 | Quint . |
| 5,088,979 | 2/1992 | Filipi et al. . |
| 5,094,233 | 3/1992 | Brennan . |
| 5,100,423 | 3/1992 | Fearnot . |
| 5,106,360 | 4/1992 | Ishiwara et al. . |
| 5,122,137 | 6/1992 | Lennox . |
| 5,125,928 | 6/1992 | Parins et al. . |
| 5,156,151 | 10/1992 | Imran . |
| 5,190,541 | 3/1993 | Abele et al. . |
| 5,197,963 | 3/1993 | Parins . |
| 5,197,964 | 3/1993 | Parins . |
| 5,205,287 | 4/1993 | Erbel et al. . |
| 5,215,103 | 6/1993 | Desai . |
| 5,232,444 | 8/1993 | Just et al. . |
| 5,236,413 | 8/1993 | Fiering . |
| 5,242,441 | 9/1993 | Avitall . |
| 5,254,126 | 10/1993 | Filipi et al. . |
| 5,256,138 | 10/1993 | Vurek et al. . |
| 5,257,451 | 11/1993 | Edwards et al. . |
| 5,263,493 | 11/1993 | Avitall . |
| 5,275,162 | 1/1994 | Edwards et al. . |
| 5,275,608 | 1/1994 | Forman et al. . |
| 5,275,610 | 1/1994 | Eberbach . |
| 5,277,201 | 1/1994 | Stern . |
| 5,281,216 | 1/1994 | Klicek . |
| 5,281,217 | 1/1994 | Edwards et al. . |
| 5,281,218 | 1/1994 | Imran . |
| 5,290,286 | 3/1994 | Parins . |
| 5,292,321 | 3/1994 | Lee . |
| 5,293,869 | 3/1994 | Edwards et al. . |
| 5,309,910 | 5/1994 | Edwards et al. . |
| 5,313,943 | 5/1994 | Houser et al. . |
| 5,314,466 | 5/1994 | Stern et al. . |
| 5,316,020 | 5/1994 | Truffer . |
| 5,324,284 | 6/1994 | Imran . |
| 5,328,467 | 7/1994 | Edwards et al. . |
| 5,330,518 * | 7/1994 | Neilson et al. .................. 607/101 |
| 5,334,193 * | 8/1994 | Nardella ......................... 606/41 |
| 5,334,196 | 8/1994 | Scott et al. . |
| 5,336,222 | 8/1994 | Durgin, Jr. et al. . |
| 5,345,936 | 9/1994 | Pomeranz et al. . |
| 5,348,554 | 9/1994 | Imran et al. . |
| 5,363,861 | 11/1994 | Edwards et al. . |
| 5,365,926 | 11/1994 | Desai . |
| 5,365,945 | 11/1994 | Halstrom . |
| 5,366,490 | 11/1994 | Edwards et al. . |
| 5,368,557 | 11/1994 | Nita et al. . |
| 5,368,592 | 11/1994 | Stern et al. . |
| 5,370,675 | 12/1994 | Edwards et al. . |
| 5,370,678 | 12/1994 | Edwards et al. . |
| 5,383,876 | 1/1995 | Nardella . |
| 5,383,917 | 1/1995 | Desai et al. . |
| 5,385,544 | 1/1995 | Edwards et al. . |
| 5,397,339 | 3/1995 | Desai . |
| 5,398,683 | 3/1995 | Edwards et al. . |
| 5,401,272 | 3/1995 | Perkins . |
| 5,403,311 | 4/1995 | Abele et al. . |
| 5,409,453 | 4/1995 | Lundquist et al. . |
| 5,409,483 | 4/1995 | Campbell et al. . |
| 5,415,657 | 5/1995 | Taymor-Luia . |
| 5,421,819 | 6/1995 | Edwards et al. . |
| 5,423,808 | 6/1995 | Edwards et al. . |
| 5,423,811 * | 6/1995 | Imran et al. ..................... 606/41 |
| 5,423,812 | 6/1995 | Ellman et al. . |
| 5,433,739 | 7/1995 | Sluijter et al. . |
| 5,435,805 | 7/1995 | Edwards . |
| 5,441,499 | 8/1995 | Fritzsch . |
| 5,443,470 | 8/1995 | Stern et al. . |
| 5,454,782 | 10/1995 | Perkins . |
| 5,456,662 | 10/1995 | Edwards et al. . |
| 5,456,682 | 10/1995 | Edwards et al. . |
| 5,458,596 | 10/1995 | Lax et al. . |
| 5,458,597 | 10/1995 | Edwards et al. . |
| 5,465,717 | 11/1995 | Imran et al. . |
| 5,470,308 | 11/1995 | Edwards et al. . |
| 5,471,982 | 12/1995 | Edwards et al. . |
| 5,472,441 | 12/1995 | Edwards et al. . |
| 5,484,400 | 1/1996 | Edwards et al. . |
| 5,486,161 | 1/1996 | Lax et al. . |
| 5,490,984 | 2/1996 | Freed . |
| 5,496,271 | 3/1996 | Burton et al. . |
| 5,496,311 | 3/1996 | Abele et al. . |
| 5,500,012 | 3/1996 | Brucker et al. . |
| 5,505,728 | 4/1996 | Ellman et al. . |
| 5,505,730 | 4/1996 | Edwards . |
| 5,507,743 | 4/1996 | Edwards et al. . |
| 5,509,419 | 4/1996 | Edwards et al. . |
| 5,514,130 | 5/1996 | Baker . |
| 5,514,131 | 5/1996 | Edwards et al. . |
| 5,520,684 | 5/1996 | Imran . |
| 5,531,676 | 7/1996 | Edwards et al. . |
| 5,531,677 | 7/1996 | Lundquist et al. . |
| 5,536,240 | 7/1996 | Edwards et al. . |
| 5,536,267 | 7/1996 | Edwards et al. . |
| 5,540,655 | 7/1996 | Edwards et al. . |
| 5,549,644 | 8/1996 | Lundquist et al. . |
| 5,554,110 | 9/1996 | Edwards et al. . |
| 5,556,377 | 9/1996 | Rosen et al. . |
| 5,558,672 | 9/1996 | Edwards et al. . |
| 5,558,673 | 9/1996 | Edwards et al. . |
| 5,562,720 | 10/1996 | Stern et al. . |
| 5,571,116 | 11/1996 | Bolanos et al. . |
| 5,578,007 | 11/1996 | Imran . |
| 5,588,432 | 12/1996 | Crowley . |
| 5,588,960 | 12/1996 | Edwards et al. . |
| 5,599,345 | 2/1997 | Edwards et al. . |
| 5,609,151 | 3/1997 | Mulier et al. . |
| 5,624,439 | 4/1997 | Edwards et al. . |
| 5,672,153 | 9/1997 | Lax et al. . |
| 5,676,674 | 10/1997 | Bolanos et al. . |
| 5,688,266 | 11/1997 | Edwards et al. . |
| 5,688,490 | 11/1997 | Tournier et al. . |
| 5,702,438 | 12/1997 | Avitall . |
| 5,709,224 | 1/1998 | Behl et al. . |
| 5,732,698 | 3/1998 | Swanson et al. . |
| 5,738,096 | 4/1998 | Ben-Haim . |
| 5,800,482 * | 9/1998 | Pomeranz et al. ............... 607/101 |
| 5,830,213 | 11/1998 | Panescu et al. . |
| 5,836,874 | 11/1998 | Swanson et al. . |

| | | |
|---|---|---|
| 5,860,974 | 1/1999 | Abele . |
| 5,871,469 * | 2/1999 | Eggers et al. .................. 604/114 |
| 5,871,481 * | 2/1999 | Kannenberg et al. ............ 606/34 |
| 5,871,483 | 2/1999 | Jackson et al. . |
| 6,073,052 | 6/2000 | Zelickson et al. . |
| 6,106,460 | 8/2000 | Panescu et al. . |

OTHER PUBLICATIONS

Kelly, KA. et al., "Doudenal–gastric reflux and slowed gastric emptying by electrical pacing of the canine duodenal pacesetter potential." Gastroenterology. 1977. 72(3): 429–33.

Reynolds, J.C. "Influence of pathophysiology, severity, and cost on the medical management of gastroesophageal reflux disease." Am J Health–Syst Pharm. 53 (22 Suppl 3): S5–12.

Urschel, J.D. "Complications of Antireflux Surgery." Am J Surg. 1993. 166(1): 68–70.

Kaneko, et al., Physiological Laryngeal Pacemaker, May 1985, Trans Am Soc. Artif. Intern Organs, Vol. XXXI, pp. 293–296.

Mugica et al. Direct Diaphragm Stimulation, Jan. 1987 PACE, vol. 10, pp. 252–256.

Mugica et al., Neurostimulation: An Overview, Chapter 21, Preliminary Test of a Muscular Diaphragm pacing System on Human Patients. 1985. pp. 3. 263–279.

Rice et al., Endoscopic Paranasal Sinus Surgery, Chapter 5, Functional Endoscopic Paranasal Sinus Surgery, The Technique of Messerklinger, Raven Press, 1988, pp. 75–104.

Rice et al., Endoscopic Paranasal Sinus Surgery, Chapter 6, Total Endoscopic Sphenoethmoidectomy, The Technique of Wigand, Raven Press, 1988, pp. 105–125.

* cited by examiner

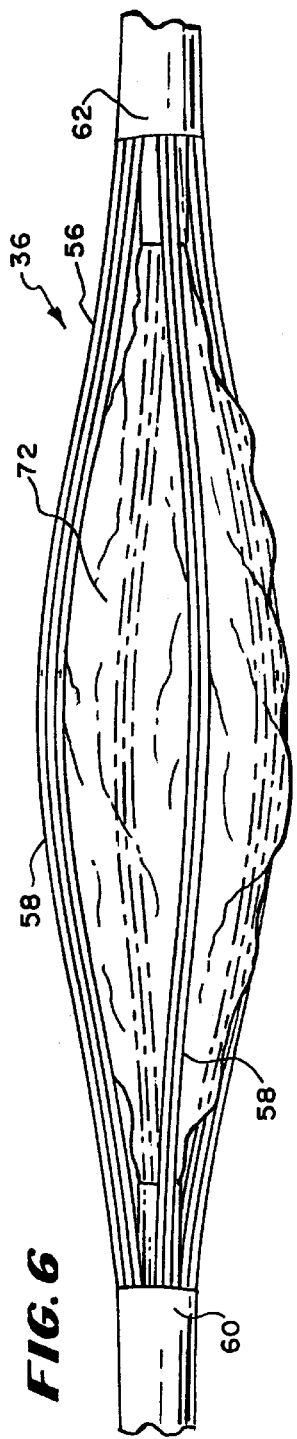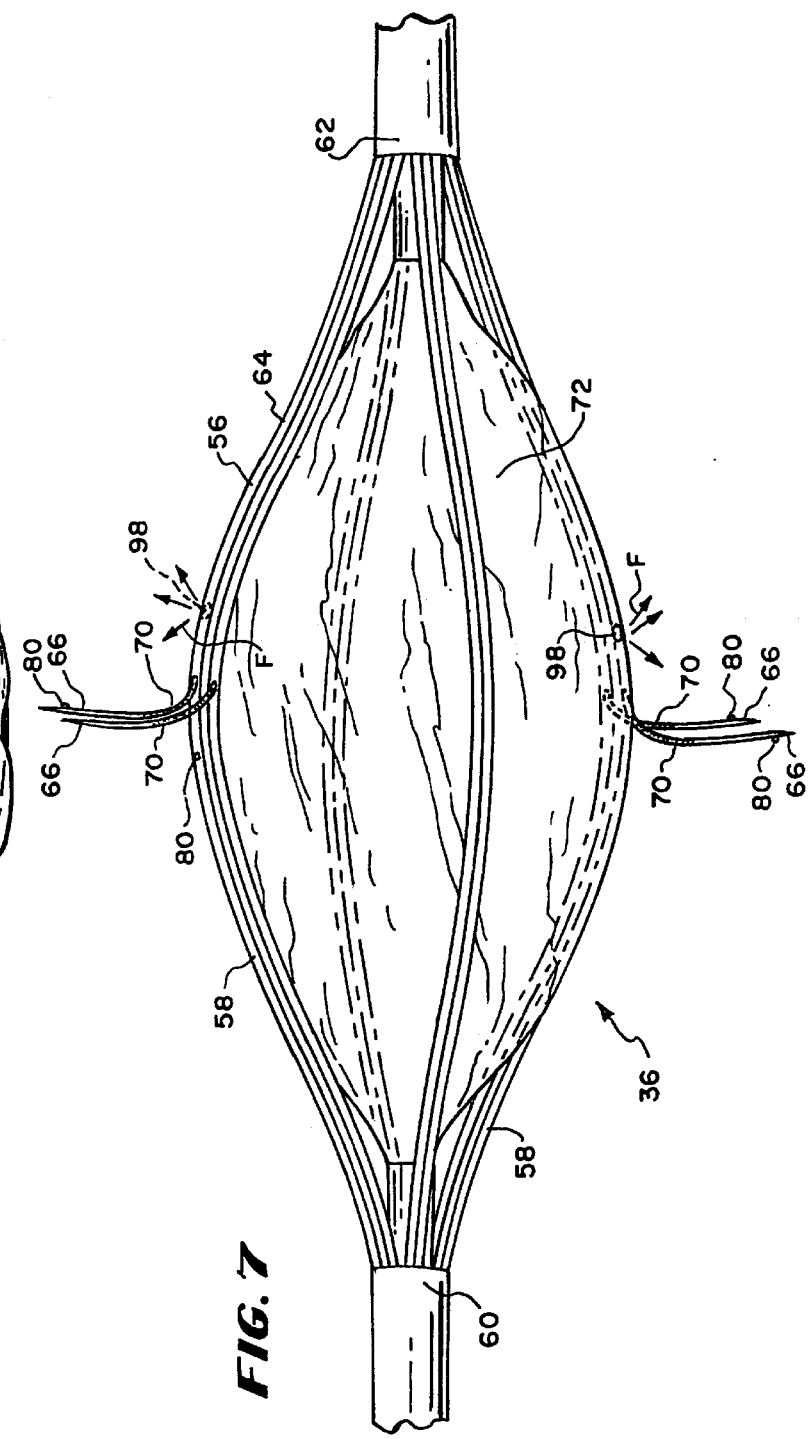
FIG. 6
FIG. 7

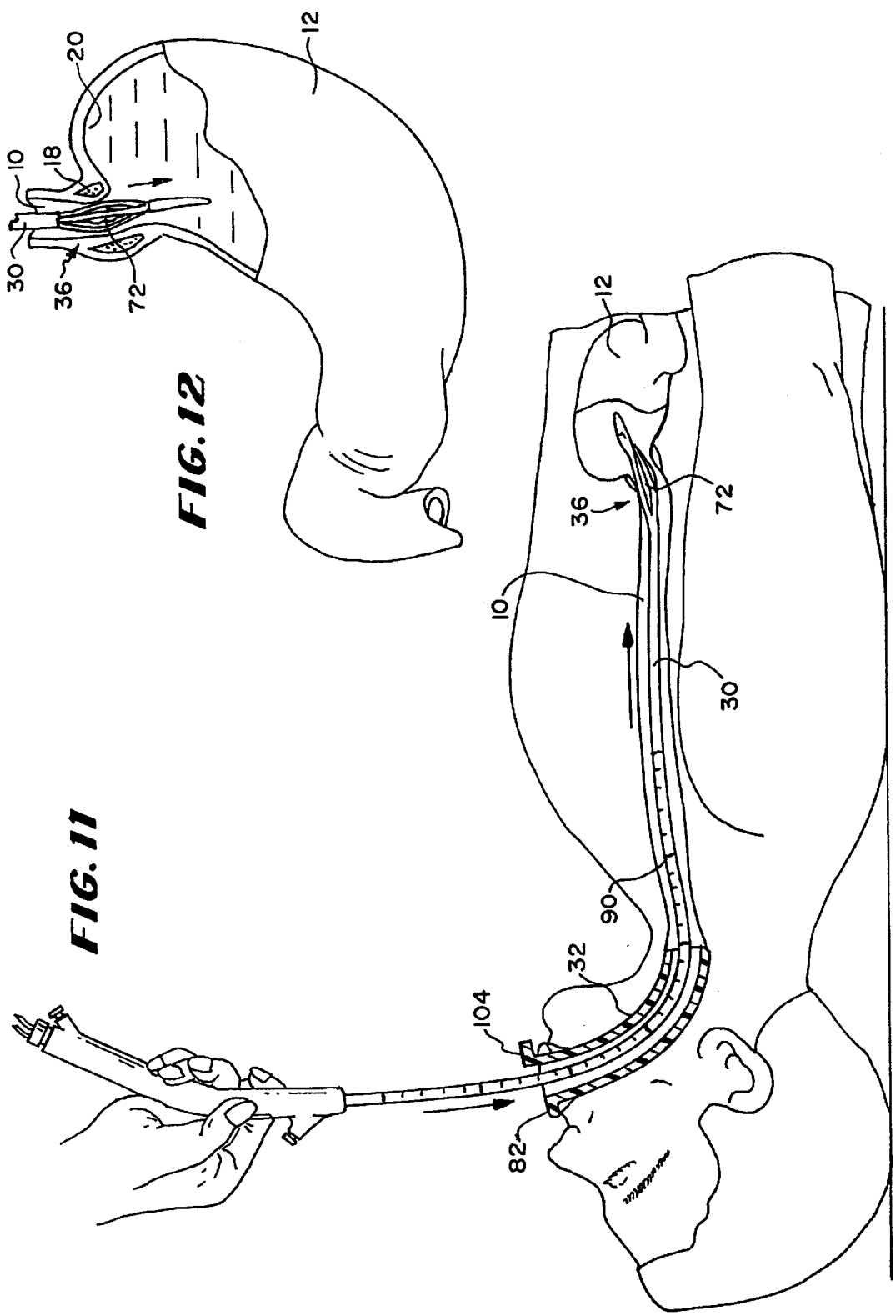

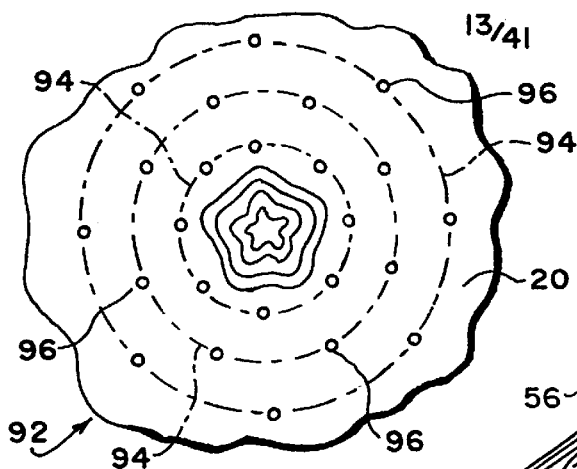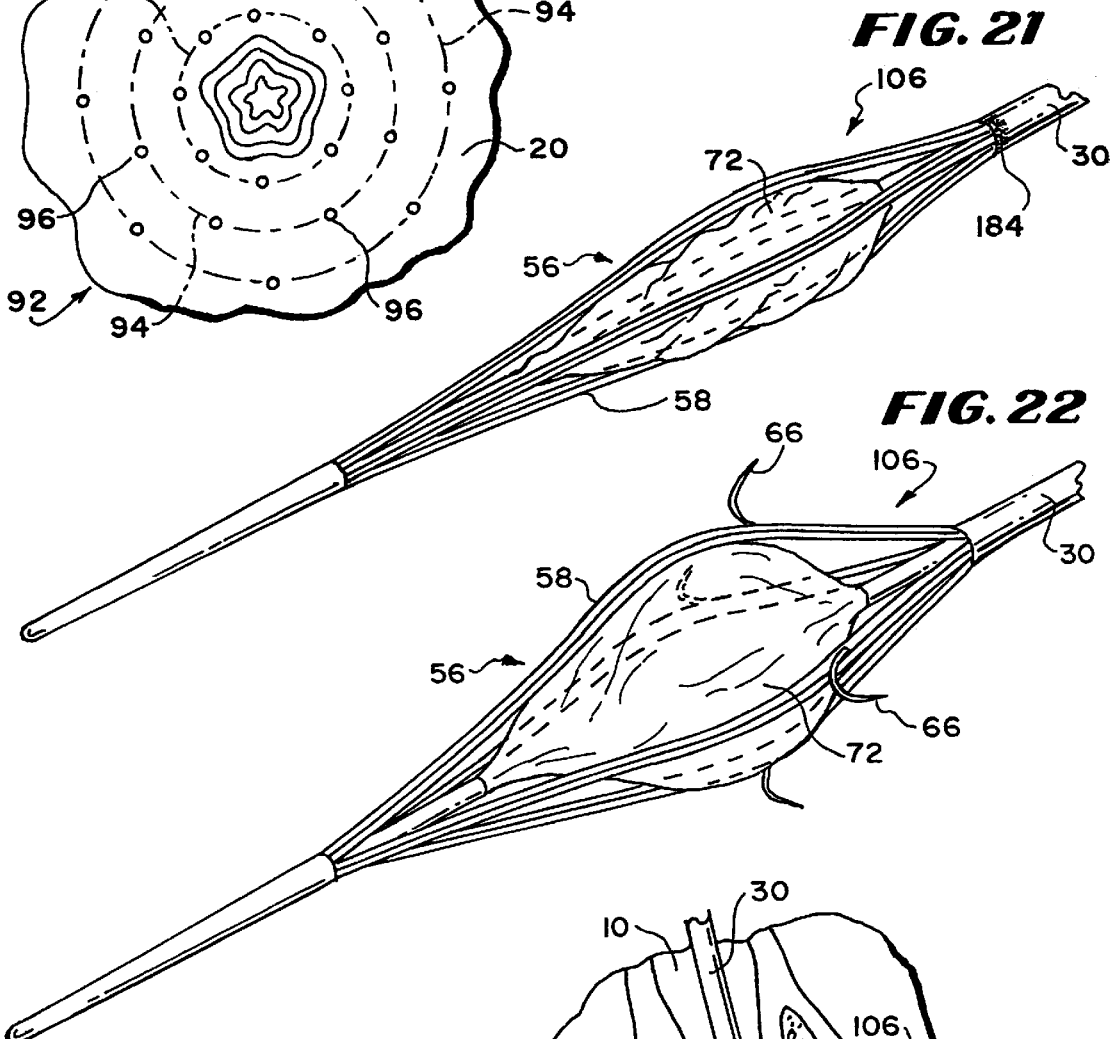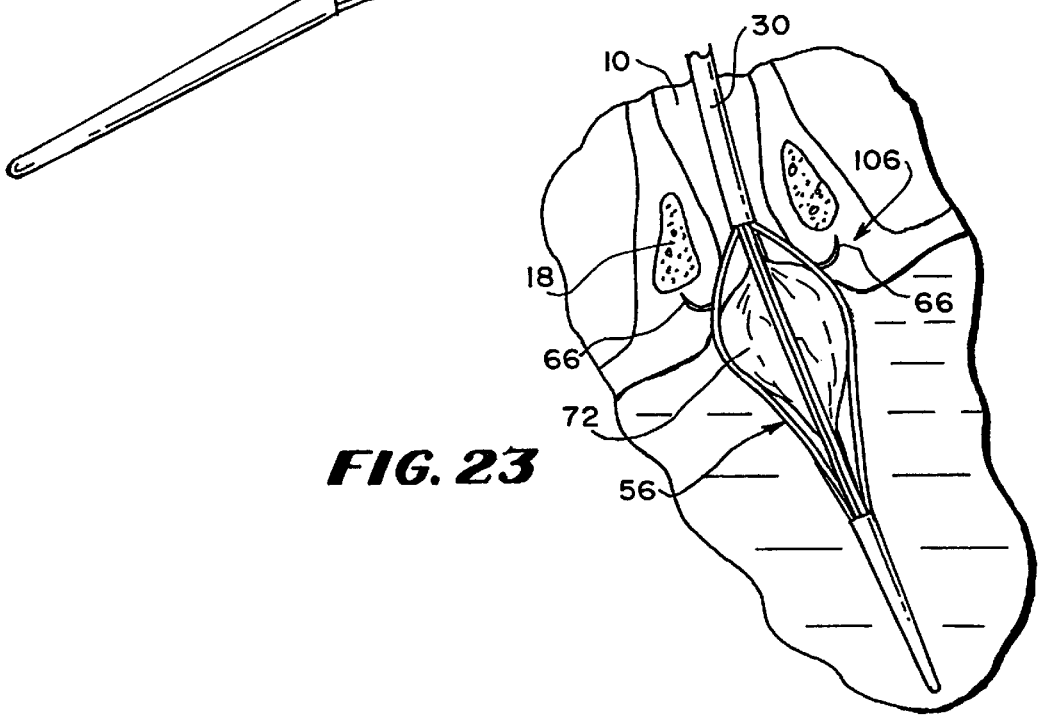

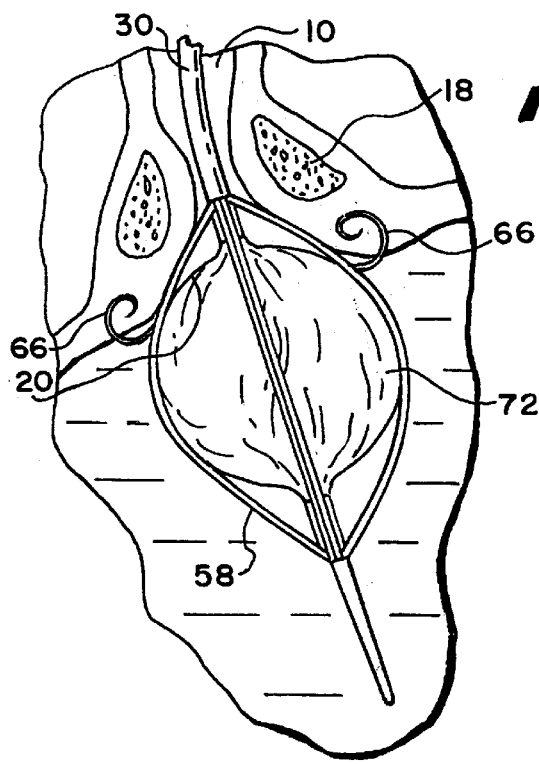
FIG. 29
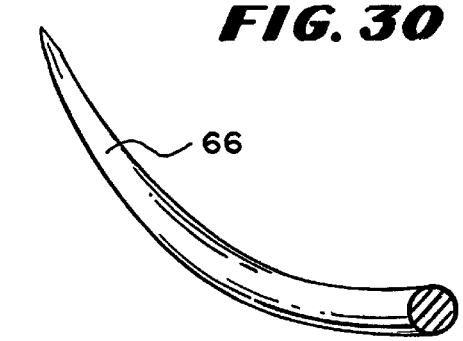
FIG. 30
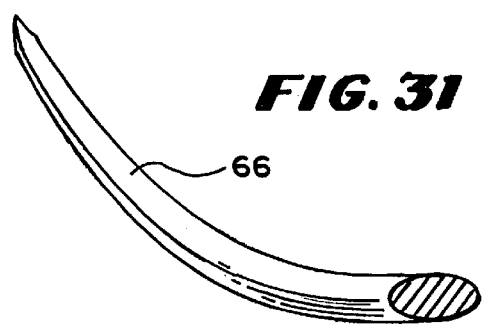
FIG. 31
FIG. 33
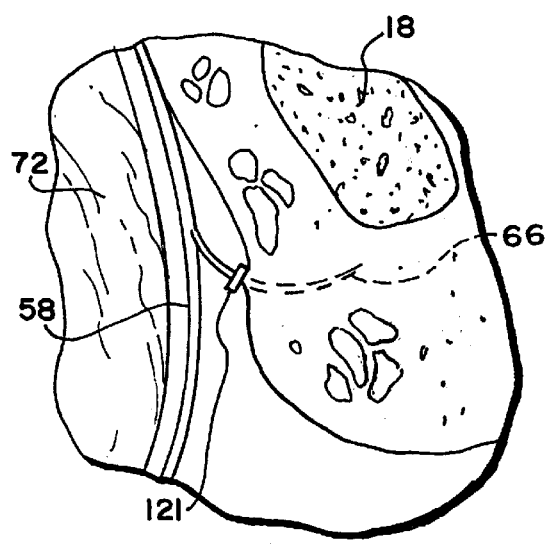
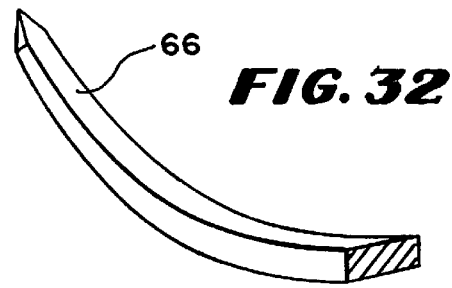
FIG. 32

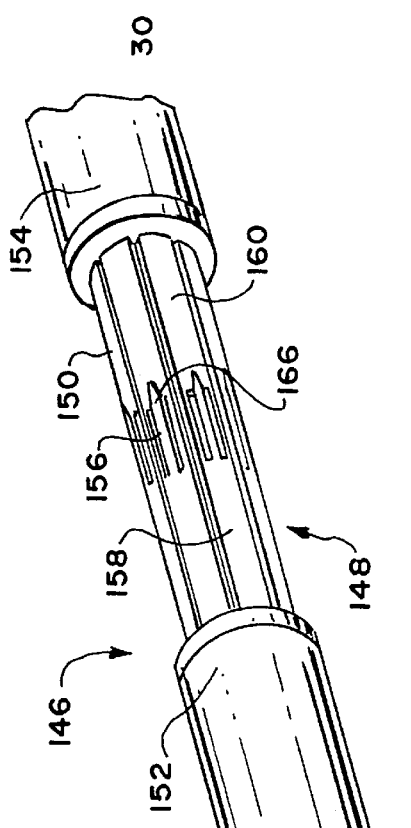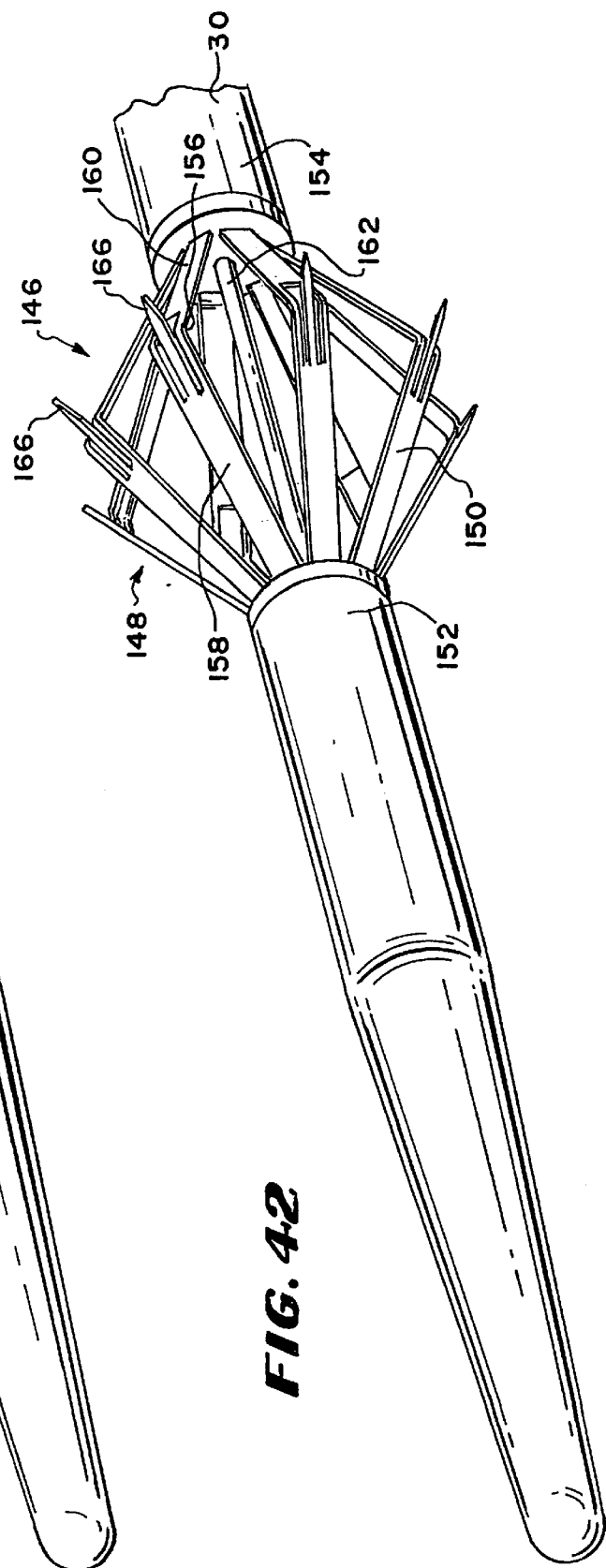
FIG. 41
FIG. 42

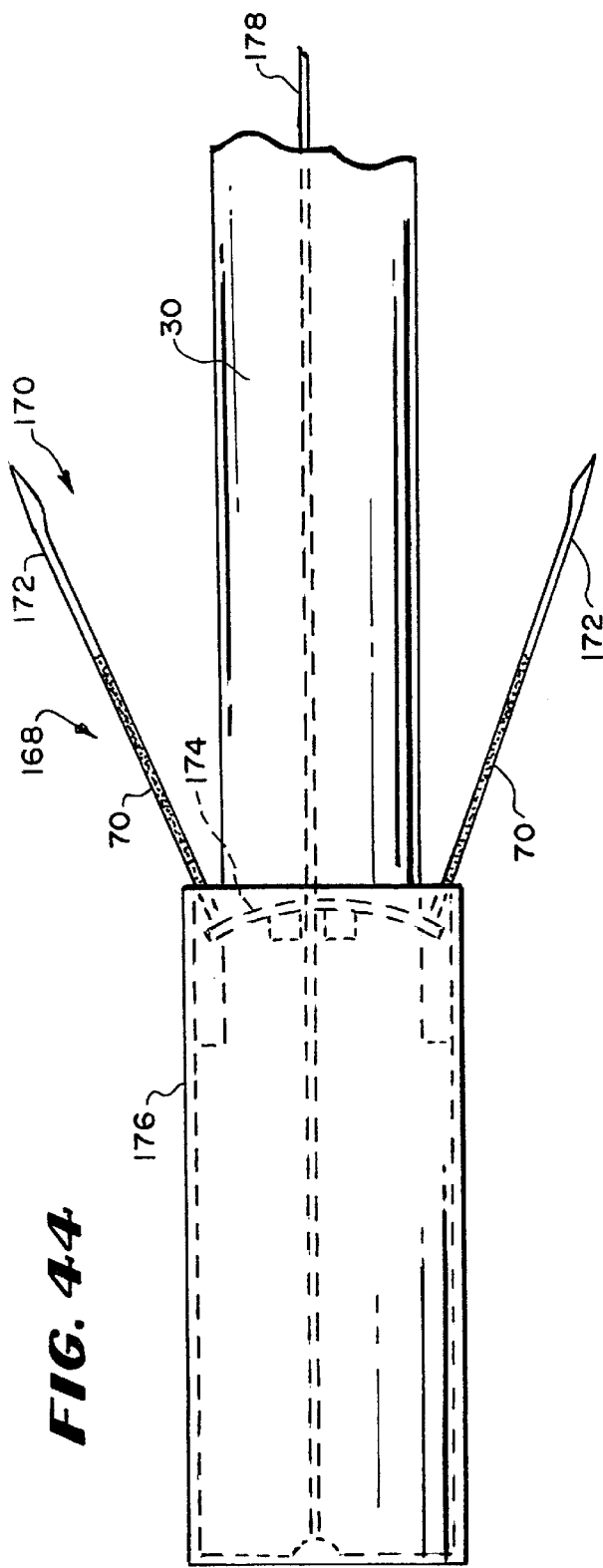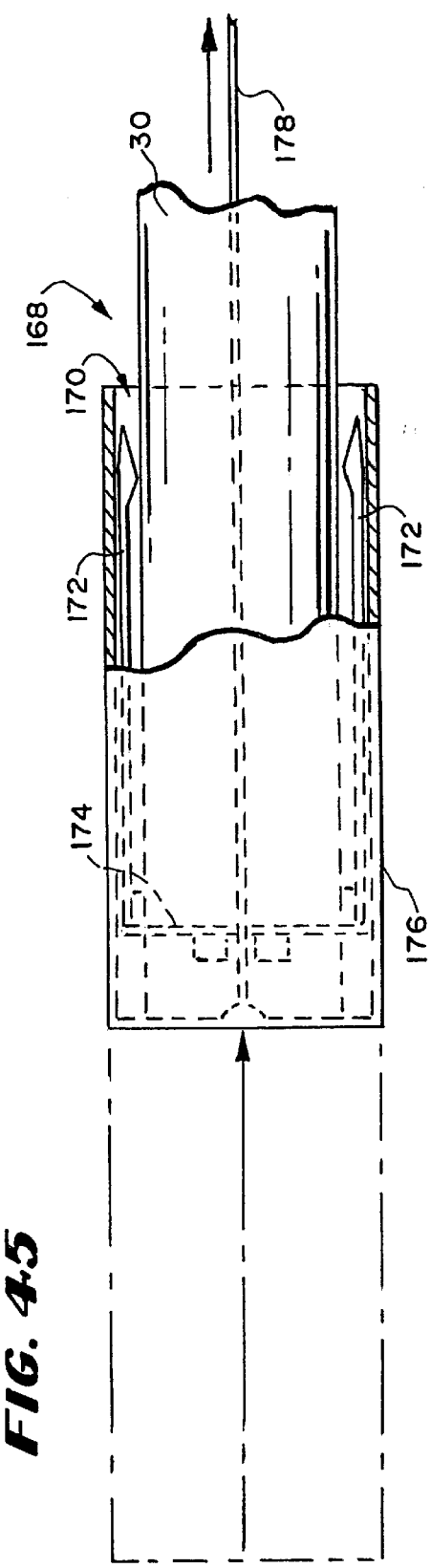
FIG. 44.
FIG. 45

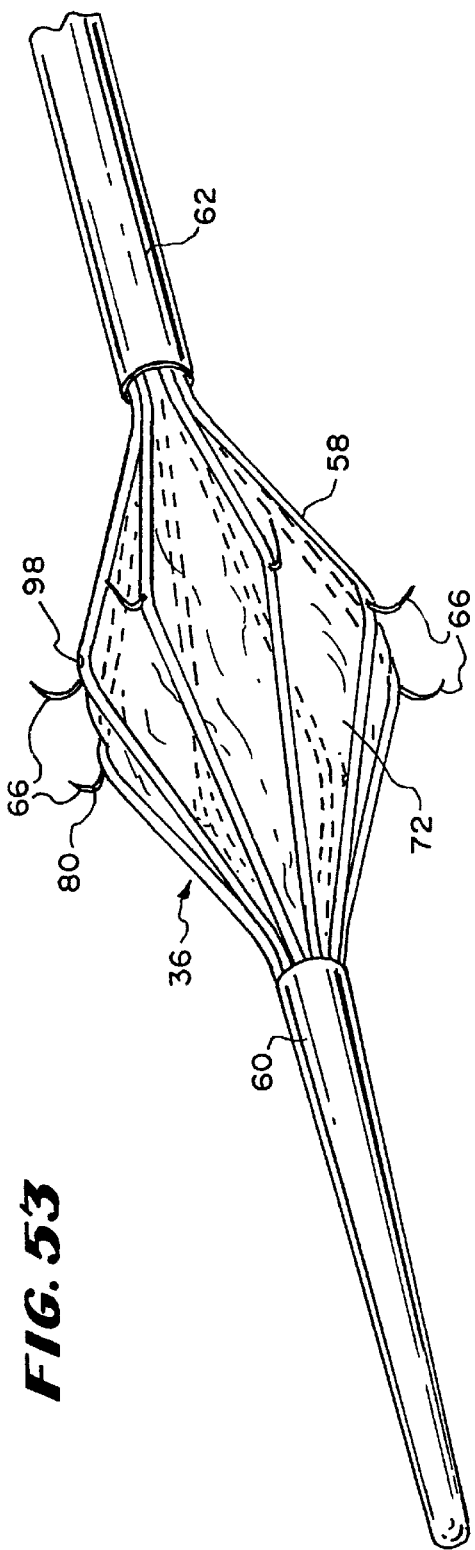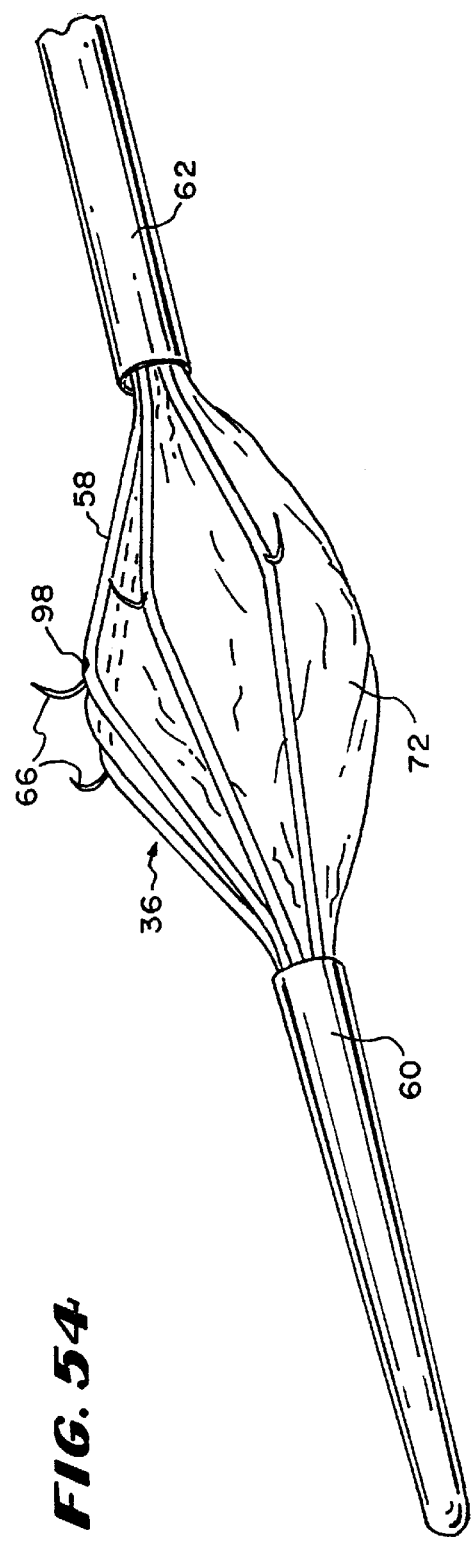

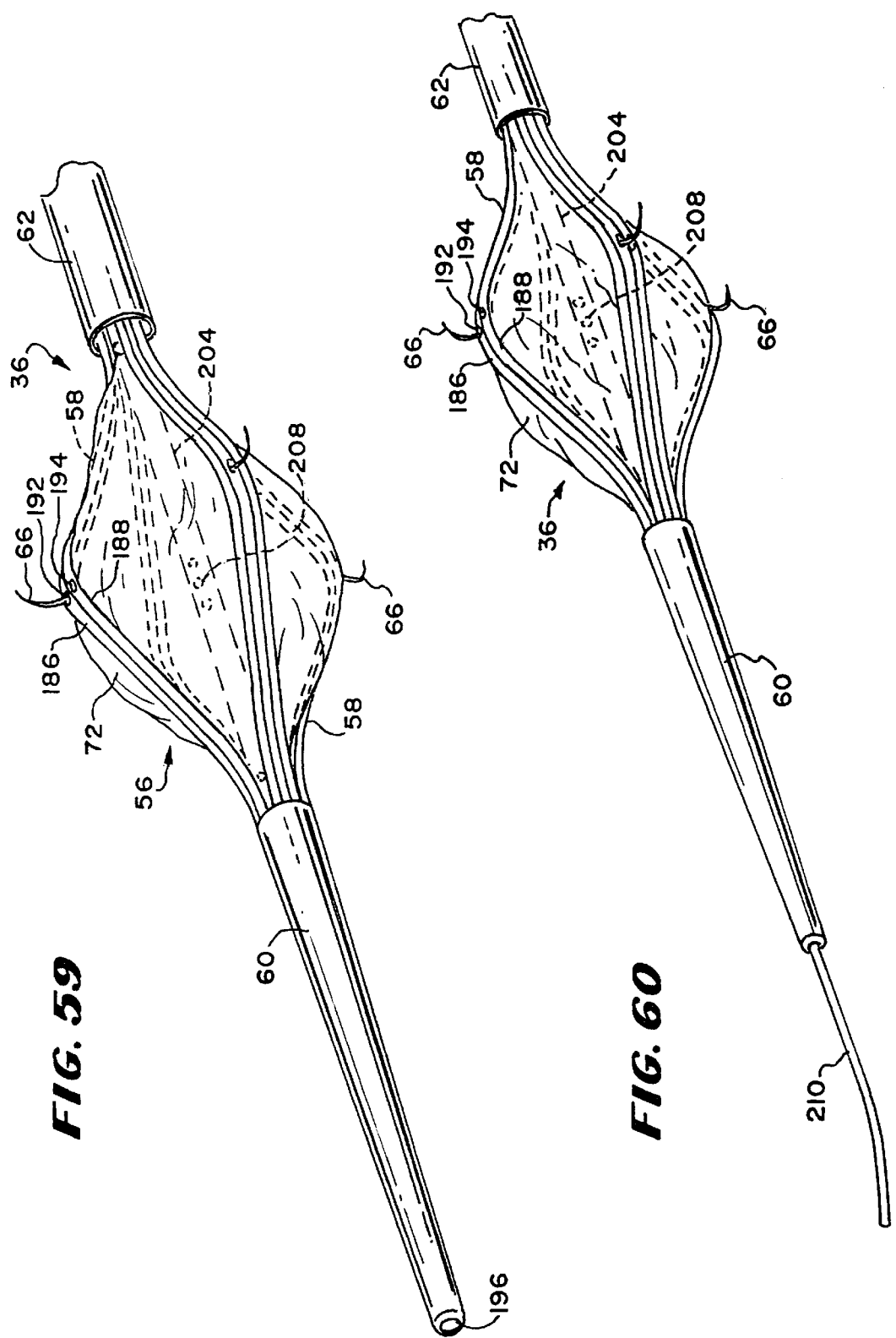

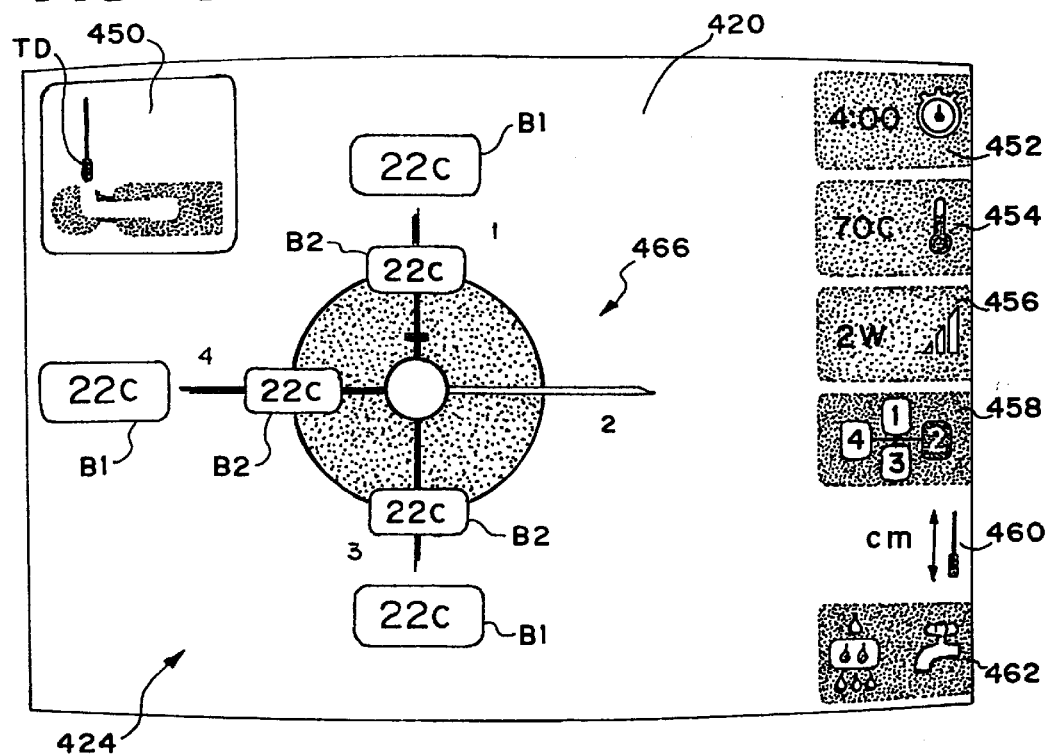
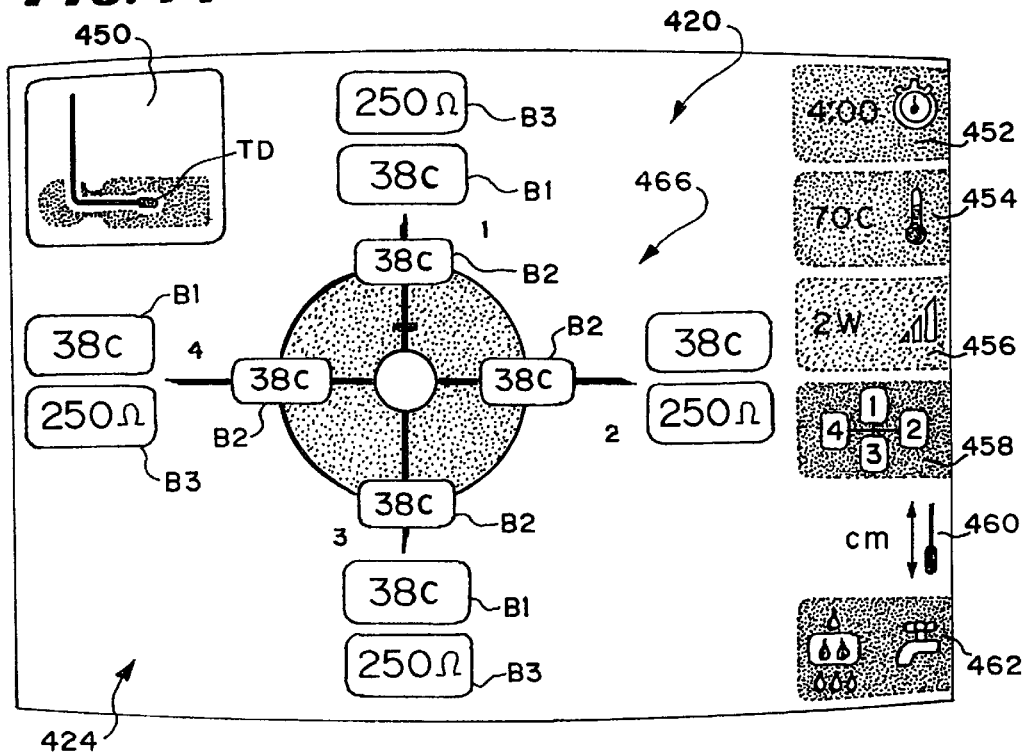

INTEGRATED TISSUE HEATING AND COOLING APPARATUS

RELATED APPLICATION

This application is a continuation-in-part of U.S. patent application Ser. No. 09/026,296, filed Feb. 19, 1998 now U.S. Pat. No. 6,009,877, and entitled "Method for Treating Sphincter."

FIELD OF THE INVENTION

In a general sense, the invention is directed to systems and methods for treating interior tissue regions of the body. More specifically, the invention is directed to systems and methods for treating dysfunction in body sphincters and adjoining tissue, e.g., in and around the lower esophageal sphincter and cardia of the stomach.

BACKGROUND OF THE INVENTION

The gastrointestinal tract, also called the alimentary canal, is a long tube through which food is taken into the body and digested. The alimentary canal begins at the mouth, and includes the pharynx, esophagus, stomach, small and large intestines, and rectum. In human beings, this passage is about 30 feet (9 meters) long.

Small, ring-like muscles, called sphincters, surround portions of the alimentary canal. In a healthy person, these muscles contract or tighten in a coordinated fashion during eating and the ensuing digestive process, to temporarily close off one region of the alimentary canal from an other.

For example, a muscular ring called the lower esophageal sphincter surrounds the opening between the esophagus and the stomach. The lower esophageal sphincter (or LES) is a ring of increased thickness in the circular, smooth-muscle layer of the esophagus. Normally, the lower esophageal sphincter maintains a high-pressure zone between fifteen and thirty mm Hg above intragastric pressures inside the stomach.

When a person swallows food, muscles of the pharynx push the food into the esophagus. The muscles in the esophagus walls respond with a wavelike contraction called peristalsis. The lower esophageal sphincter relaxes before the esophagus contracts, and allows food to pass through to the stomach. After food passes into the stomach, the lower esophageal sphincter constricts to prevent the contents from regurgitating into the esophagus.

The stomach muscles churn the food and digestive juices into a mass called chyme. Then the muscles squeeze the chyme toward the pyloric (intestinal) end of the stomach by peristaltic waves, which start at the top of the stomach and move downward. The pyloric sphincter, another ringlike muscle, surrounds the duodenal opening. The pyloric sphincter keeps food in the stomach until it is a liquid. The pyloric sphincter then relaxes and lets some chyme pass into the duodenum.

Dysfunction of a sphincter in the body can lead to internal damage or disease, discomfort, or otherwise adversely affect the quality of life. For example, if the lower esophageal sphincter fails to function properly, stomach acid may rise back into the esophagus. Unlike the stomach, the esophagus has no natural protection against stomach acids. When the stomach contents make contact with the esophagus, heartburn or other disease symptoms, including damage to the esophagus, can occur.

Gastrointestinal reflux disease (GERI)) is a common disorder, characterized by spontaneous relaxation of the lower esophageal sphincter. It has been estimated that approximately two percent of the adult population suffers from GERD. The incidence of GERD increases markedly after the age of 40, and it is not uncommon for patients experiencing symptoms to wait years before seeking medical treatment.

GERD is both a normal physiologic phenomenon that occurs in the general population and a pathophysiologic phenomenon that can result in mild to severe symptoms.

GERD is believed to be caused by a combination of conditions that increase the presence of acid reflux in the esophagus. These conditions include transient LES relaxation, decreased LES resting tone, impaired esophageal clearance, delayed gastric emptying, decreased salivation, and impaired tissue resistance. Since the resting tone of the lower esophageal sphincter is maintained by both myogenic (muscular) and neurogenic (nerve) mechanisms, some believe that aberrant electrical signals in the lower esophageal sphincter or surrounding region of the stomach (called the cardia) can cause the sphincter to spontaneously relax.

Lifestyle factors can also cause increased risk of reflux. Smoking, large meals, fatty foods, caffeine, pregnancy, obesity, body position, drugs, hormones, and paraplegia may all exacerbate GERD. Also, hiatal hernia frequently accompanies severe GERD. The hernia may increase transient LES relaxation and delay acid clearance due to impaired esophageal emptying. Thus, hiatal hernias may contribute to prolonged acid exposure time following reflux, resulting in GERD symptoms and esophageal damage.

The excessive reflux experienced by patients with GERD overwhelms their intrinsic mucosal defense mechanisms, resulting in many symptoms. The most common symptom of GERD is heartburn. Besides the discomfort of heartburn, reflux results in symptoms of esophageal inflammation, such as odynophagia (pain on swallowing) and dysphagia (difficult swallowing). The acid reflux may also cause pulmonary symptoms such as coughing, wheezing, asthma, aspiration pneumonia, and interstitial fibrosis; oral symptoms such as tooth enamel decay, gingivitis, halitosis, and waterbrash; throat symptoms such as a soreness, laryngitis, hoarseness, and a globus sensation; and earache.

Complications of GERD include esophageal erosion, esophageal ulcer, and esophageal stricture; replacement of normal esophageal epithelium with abnormal (Barrett's) epithelium; and pulmonary aspiration.

Treatment of GERD includes drug therapy to reduce or block stomach acid secretions. Still, daily drug therapy does not eliminate the root cause of the dysfunction.

Invasive abdominal surgical intervention has also been tried with success. One procedure, called Nissen fundoplication, entails invasive, open abdominal surgery. The surgeon wraps the gastric fundis about the lower esophagus, to, in effect, create a new "valve." Less invasive laparoscopic tehniques have also been tried to emulate Nissen fundoplication, also with success. Still, all surgical intervention entails making an incision into the abdomen and carry with it the usual risks of abdominal surgery.

SUMMARY OF THE INVENTION

The invention provides improved systems and methods for treating a tissue region. The systems and methods integrate the control of a generator, to supply energy to an electrode structure to heat a tissue region, and the control of a pumping mechanism, to supply cooling fluid to control tissue temperature in the region.

One aspect of the invention provides a device for association with an electrode structure which, in use, is deployed in a tissue region. The device comprises a housing. A generator is integrated in the housing to generate energy capable of heating tissue and adapted to be coupled to the electrode structure to apply the energy to the tissue region. A pumping mechanism is also integrated in the housing and adapted to be attached to tubing to dispense cooling fluid from a source to the tissue region. The device includes a controller integrated in the housing and coupled to the generator and the pumping mechanism. The controller enables control of the generator in supplying energy to the electrode structure to raise tissue temperature in the tissue region, in concert with operation of the pumping mechanism in supplying cooling fluid to the tissue region to control the tissue temperature.

In one embodiment, the generator generates radio frequency energy.

In one embodiment, the pumping mechanism includes a peristaltic pump rotor.

In one embodiment, the device further includes an aspiration module adapted to be attached to tubing to remove cooling liquid from the tissue region. In one embodiment, the aspiration module is integrated in the housing. In another embodiment, the aspiration module includes an external vacuum source.

According to another aspect of the invention, the integrated device also includes a display screen and an operating system coupled to the display screen to show an animated visual image indicating operation of the generator and an animated visual image indicating operation of the pumping mechanism.

According to another aspect of the invention, the electrode served by the device has a distal end that, in use, penetrates tissue in the tissue region. The controller includes an input adapted to be attached to a first temperature sensor carried by the electrode structure to monitor surface tissue temperature and a second temperature sensor carried by the distal end of the electrode to monitor subsurface tissue temperature. The controller includes a function responsive to monitored surface tissue temperature, or monitored subsurface tissue temperature, or both, to control operation of the generator in concert with operation of the pumping mechanism, to thereby enable command of the generator and the pumping mechanism to controllably heat tissue in the tissue region.

In one embodiment, the controller includes a display screen and an operating system coupled to the display screen. The operating system generates an image that, e.g., represents monitored surface tissue temperature, or monitored subsurface tissue temperature, or both; or represents changes to monitored surface tissue temperature, or monitored subsurface tissue temperature, or both over time; an idealized image of the distal end of the electrode in spatial relation to an idealized image of the support structure. In the latter arrangement, the viewable image can also include an indication of the monitored surface tissue temperature shown in spatial association with the idealized image of the support structure and an indication of the monitored subsurface tissue temperature shown in spatial association with the idealized image of the distal end of the electrode.

According to another aspect of the invention, the controller includes an ON input to command application of energy to the electrode structure and a function that, in response to the ON input, commences operation of the pumping mechanism for a prescribed time period while delaying operation of the generator until the prescribed time period lapses.

According to another aspect of the invention, the controller includes an OFF input to command termination of the application of energy to the electrode structure and a function that, in response to the OFF input, operates the pumping mechanism for a prescribed time period after the supply of energy is terminated.

According to another aspect of the invention, the controller includes an ON input to command application of energy to the electrode structure in concert with operation of the pumping mechanism and an OFF input to command termination of the application of energy to the electrode structure. The controller further includes a display screen and an operating system coupled to the display screen to generate, after the ON input, an ON image comprising a time record of changes in at least one operating condition over time during operation of the generator and the pumping mechanism and, after the OFF input, a PAUSE image that preserves the time record.

Features and advantages of the inventions are set forth in the following Description and Drawings, as well as in the appended Claims.

BRIEF DESCRIPTION OF THE DRAWINGS

FIG. 6 is an enlarged side view of the operative element when collapsed, as also shown in FIG. 3;

FIG. 7 is an enlarged side view of the operative element when expanded and with the electrodes extended for use, as also shown in FIG. 5;

FIG. 11 is a side view of the deployment of the device shown in FIG. 3 after deployment of the flexible endoscope shown in FIG. 9, placing the operative element in the region of the lower esophageal sphincter;

FIG. 12 is an enlarged view of the operative element shown in FIG. 11, when placed in the region of the lower esophageal sphincter;

FIG. 20 is a top view of a targeted tissue region in the cardia, showing a desired pattern of lesions;

FIG. 21 is a perspective view of a "pear-shaped" operative element intended for deployment in the cardiac shown in a collapsed condition;

FIG. 22 is a perspective view of the "pear-shaped" shown in FIG. 21, shown in an expanded condition with the electrodes extended for use in an antegrade orientation;

FIG. 23 is an enlarged view of the operative element shown in FIG. 22, when expanded into contact with muscosal tissue in the cardia and with the electrodes extended to create lesions in the smooth muscle of the cardia;

FIG. 29 is an enlarged side view an operative element expanded into contact with muscosal tissue in the cardia and with "pig-tail" electrodes extended to create lesions in the smooth muscle of the cardia;

FIG. 30 is a enlarged perspective section view of an electrode having a cyindrical cross section;

FIG. 31 is a enlarged perspective section view of an electrode having an elliptical cross section to resist twisting;

FIG. 32 is a enlarged perspective section view of an electrode having a rectilinear cross section to resist twisting;

FIG. 33 is an enlarged side view of an electrode deployed from an operative element in the region of the lower esophageal sphincter and having a collar to control the depth of tissue penetration;

FIG. 41 is a perspective view of an operative element comprising a mechanically expandable basket shown in a collapsed condition;

FIG. 42 is a perspective view of the operative element shown in FIG. 41, with the operative element shown in an expanded condition to extend the electrodes for use;

FIG. 44 is a side view of another operative element comprising a mechanically expandable basket shown in an expanded condition with the electrodes extended for use shown;

FIG. 45 is a side view of the operative element shown in FIG. 44 in a collapsed condition;

FIG. 53 is a perspective view of an operative element for treating body sphincters and adjoining tissue regions, shown in an expanded condition with eight electrodes extended for use;

FIG. 54 is a perspective view of an operative element for treating body sphincters and adjoining tissue regions, shown in an expanded condition and four closely spaced electrodes extended for use;

FIG. 59 a perspective view of an operative element for treating body sphincters and adjoining tissue regions, shown a spine structure with cooling ports located in the spines and an aspiration port located in its distal tip;

FIG. 60 a perspective view of the operative element shown in FIG. 59, deployed over a guide wire that passes through its distal tip;

FIG. 76 is a view of the graphical user interface shown in FIG. 73 showing the Standby screen after connection of a treatment device and after an electrode channel has been disabled by selection;

FIG. 77 is a view of the graphical user interface shown in FIG. 73 showing the Ready screen;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification discloses various catheter-based systems and methods for treating dysfunction of sphincters and adjoining tissue regions in the body. The systems and methods are particularly well suited for treating these dysfunctions in the upper gastrointestinal tract, e.g., in the lower esophageal sphincter and adjacent cardia of the stomach. For this reason, the systems and methods will be described in this context.

Still, it should be appreciated that the disclosed systems and methods are applicable for use in treating other dysfunctions elsewhere in the body, which are not necessarily sphincter-related. For example, the various aspects of the invention have application in procedures requiring treatment of hemorrhoids, or incontinence, or restoring compliance to or otherwise tightening interior tissue or muscle regions. The systems and methods that embody features of the invention are also adaptable for use with systems and surgical techniques that are not necessarily catheter-based.

I. Anatomy of the Lower Esopageal Sphincter Region

Figure 1:
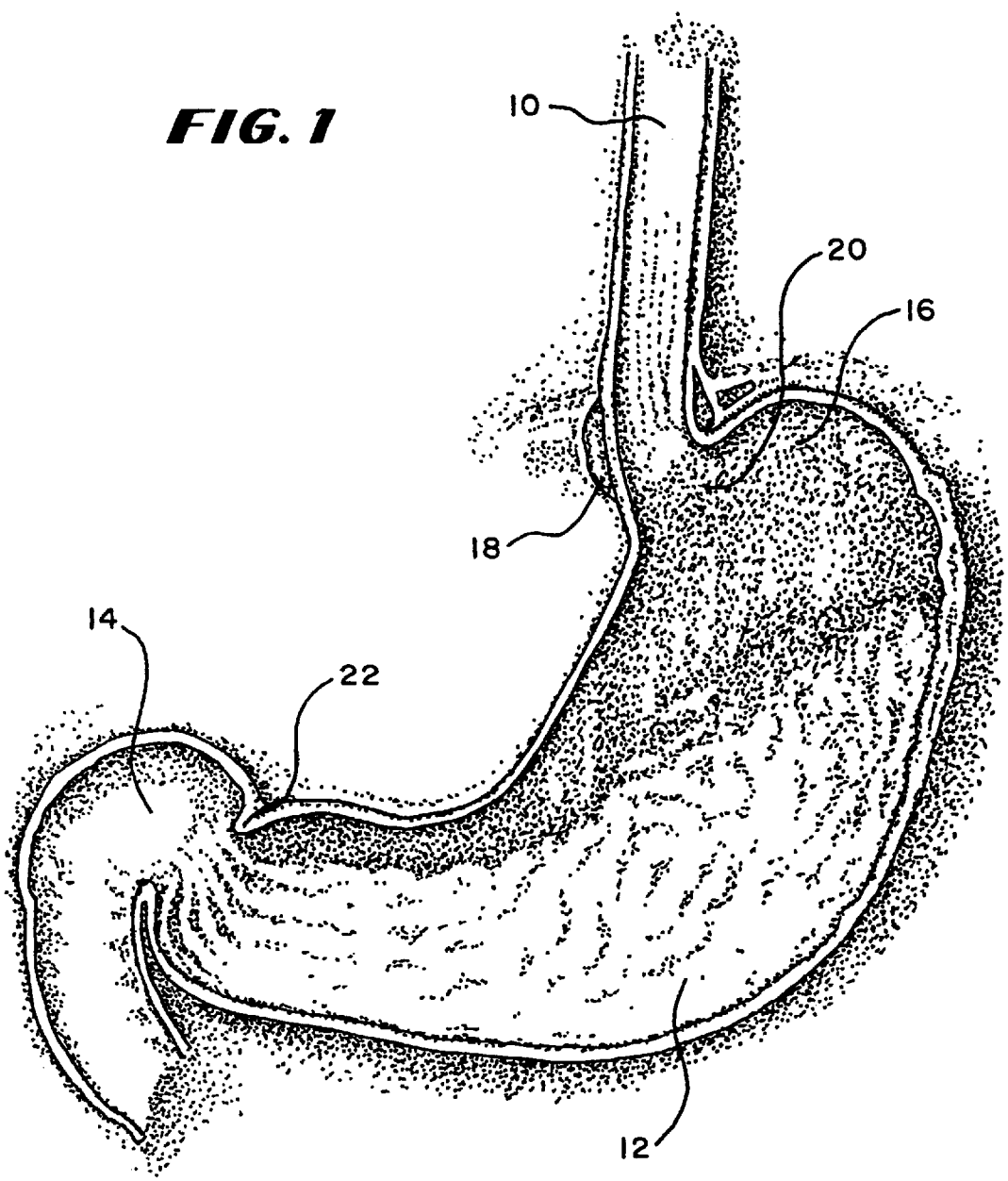
FIG. 1 is an anatomic view of the esophagus and stomach.

As FIG. 1 shows, the esophagus 10 is a muscular tube that carries food from the mouth to the stomach 12. The muscles in the walls of the esophagus 10 contract in a wavelike manner, moving the food down to the stomach 12. The interior wall of the esophagus includes glands that secrete mucus, to aid in the movement of food by providing lubrication. The human esophagus is about twenty-five centimeters long.

The stomach 12, located in the upper left hand side of the abdomen, lays between the esophagus 10 and the small intestine 14. In people and most animals, the stomach 12 is a simple baglike organ. A human being's stomach is shaped much like a J.

The average adult stomach can hold a little over one quart (0.95 liter). The stomach 12 serves, as a storage place for food. Food in the stomach 12 is discharged slowly into the intestines 14. The stomach 12 also helps digest food.

The upper end of the stomach connects with the esophagus 10 at the cardiac notch 16, at the top of the J-shape. The muscular ring called the lower esophageal sphincter 18 surrounds the opening between the esophagus 10 and the stomach 12. The funnel-shaped region of the stomach 12 immediately adjacent to the sphincter 18 is called the cardia 20. The cardia 20 comprises smooth muscle. It is not a sphincter.

The lower esophageal sphincter 18 relaxes, or opens, to allow swallowed food to enter the stomach 12. The lower esophageal sphincter 18, however, is normally closed, to keep the stomach 12 contents from flowing back into the esophagus 10.

Another sphincter, called the pyloric sphincter 22, surrounds the duodenal opening of the stomach 12. The pyloric sphincter 22 keeps non-liquid food material in the stomach 12 until it is processed into a more flowable, liquid form. The time that the stomach 12 retains food varies. Usually, the stomach 12 empties in three to five hours.

In a person suffering from GERD, the lower esophageal sphincter 18 is subject to spontaneous relaxation. The sphincter 18 opens independent of the normal swallowing function. Acidic stomach contents surge upward into the esophagus 10, causing pain, discomfort, and damage the mucosal wall of the esophagus 10.

The stomach 12 distends to accommodate various food volumes. Over time, stomach distention can stretch the cardia 20 or otherwise cause loss of compliance in the cardia 20. Loss of compliance in the cardia 20 can also pull the lower esophageal sphincter 18 open when the stomach 12 is distended, even absent sphincter muscle relaxation. The same undesired results occur: acidic stomach contents can surge upward into the esophagus 10 with the attendant undesired consequences.

It should be noted that the views of the esophagus and stomach shown in FIG. 1 and elsewhere in the drawings are not intended to be strictly accurate in an anatomic sense. The drawings show the esophagus and stomach in somewhat diagrammatic form to demonstrate the features of the invention.

II. Systems for Sphincters or Adjoining Tissue Regions

A. System Overview

Figure 2:
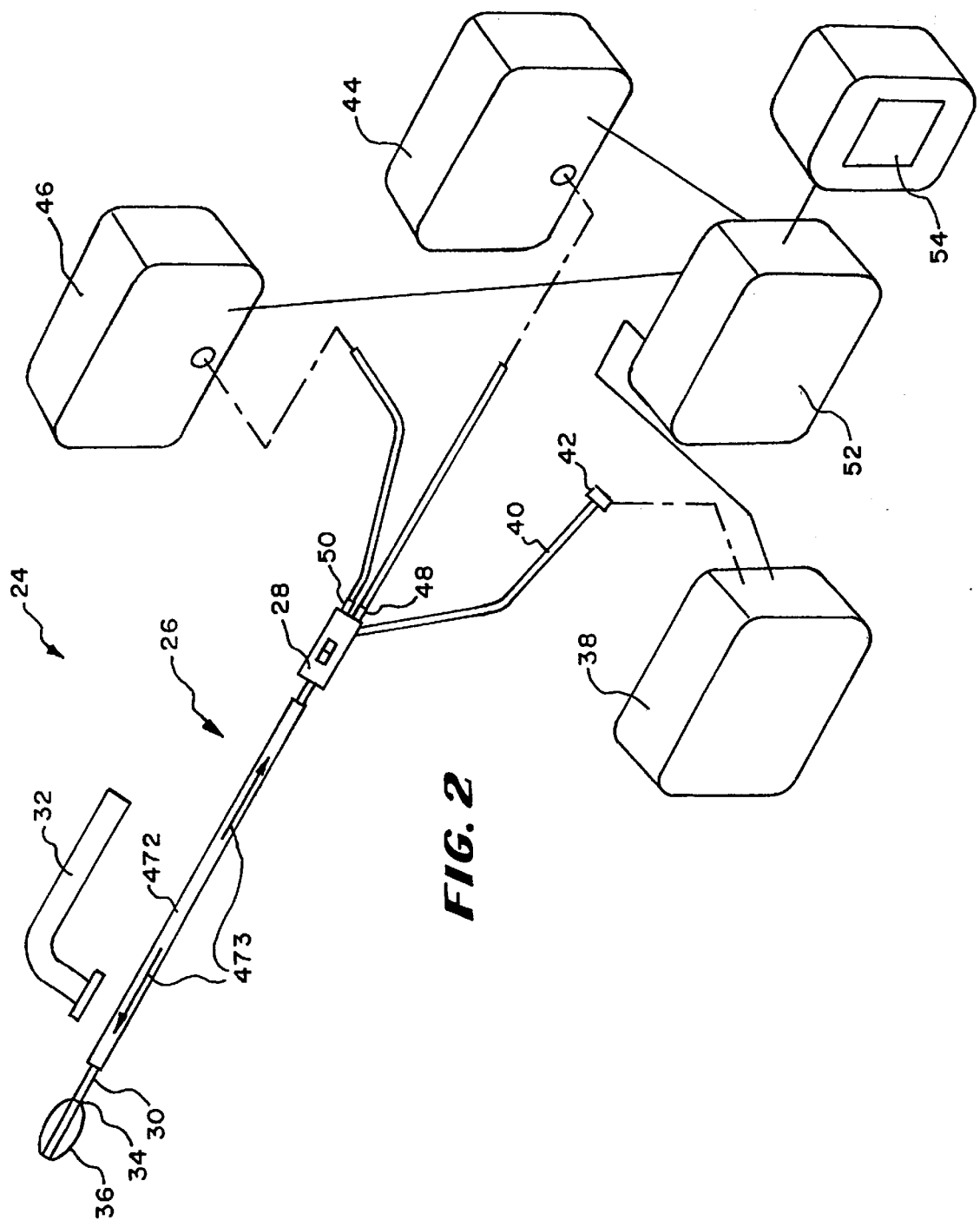
FIG. 2 is a diagrammatic view of a system for treating body sphincters and adjoining tissue regions, which embodies features of the invention.

FIG. 2 shows a system 24 for diagnosing and/or treating dysfunction of the lower esophageal sphincter 18 and/or the adjoining cardia 20 of the stomach 12.

The system 24 includes a treatment device 26. The device 26 includes a handle 28 made, e.g., from molded plastic. The handle 28 carries a flexible catheter tube 30. The catheter tube 30 can be constructed, for example, using standard flexible, medical grade plastic materials, like vinyl, nylon, poly(ethylene), ionomer, poly(urethane), poly(amide), and poly(ethylene terephthalate). The handle 28 is sized to be conveniently held by a physician, to introduce the catheter tube 30 into the esophagus 10. The details of using the treatment device 28 will be described later.

The handle 28 and the catheter tube 30 can form an integrated construction intended for a single use and subsequent disposal as a unit. Alternatively, the handle 28 can comprise a nondisposable component intended for multiple uses. In this arrangement, the catheter tube 30, and components carried at the end of the catheter tube 30 (as will be described), comprise a disposable assembly, which the physician releasably connects to the handle 28 at time of use and disconnects and discards after use. The catheter tube 30 can, for example, include a male plug connector that couples to a female plug receptacle on the handle 28.

The system 24 may include an esophageal introducer 32. The esophageal introducer 32 is made from a rigid, inert plastic material, e.g., poly(ethylene) or polyvinyl chloride. As will be described later, the introducer 32 aids in the deployment of the catheter tube 30 into the esophagus 10 through the mouth and throat of a patient.

Alternatively, the catheter tube 30 may be deployed over a guide wire through the patient's mouth and pharynx, and into the esophagus 10, without use of an introducer 32, as will be described later. Still alternatively, the catheter tube 30 may be passed through the patient's mouth and pharynx, and into the esophagus 10, without use of either a guide wire or introducer 32.

The catheter tube 30 has a distal end 34, which carries an operative element 36. The operative element 36 can take different forms and can be used for either therapeutic purposes, or diagnostic purposes, or both.

The catheter tube 30 can carry a protection sheath 472 (see FIG. 2) for the operative element 36. The sheath 472 slides along the catheter tube 30 (as indicated by arrows 473 in FIG. 2) between a forward position enclosing the operative element 36 and a rearward position free of the operative element 36. When in the forward position, the sheath 472 prevents contact between tissue and the operative element 36, thereby aiding in the deployment and removal of the operative element 36 through the patient's mouth and pharynx. When in the rearward position, the sheath 472 frees the operative element 36 for use.

As will be described in greater detail later, the operative element 36 can support, for example, a device for imaging body tissue, such as an endoscope, or an ultrasound transducer. The operative element 36 can also support a device to deliver a drug or therapeutic material to body tissue. The operative element 36 can also support a device for sensing a physiological characteristic in tissue, such as electrical activity, or for transmitting energy to stimulate or form lesions in tissue.

According to the invention, one function that the operative element 36 shown in the illustrated embodiment performs is to apply energy in a selective fashion to a targeted sphincter or other body region, which, for the purpose of illustration, are identified as the lower esophageal sphincter 18, or cardia 20, or both. The applied energy creates one or more lesions, or a prescribed pattern of lesions, below the mucosal surface of the esophagus 10 or cardia 20. The subsurface lesions are formed in a manner that preserves and protects the mucosal surface against thermal damage.

It has been discovered that natural healing of the subsurface lesions leads to a physical tightening of the sphincter 18 and/or adjoining cardia 20. The subsurface lesions can also result in the interruption of aberrant electrical pathways that may cause spontaneous sphincter relaxation. In any event, the treatment can restore normal closure function to the sphincter 18.

In this arrangement, the system 24 includes a generator 38 to supply the treatment energy. In the illustrated embodiment, the generator 38 supplies radio frequency energy, e.g., having a frequency in the range of about 400 kHz to about 10 mHz. Of course, other forms of energy can be applied, e.g., coherent or incoherent light; heated or cooled fluid; resistive heating; microwave; ultrasound; a tissue ablation fluid; or cryogenic fluid.

A cable 40 extending from the proximal end of the handle 28 terminates with an electrical connector 42. The cable 40 is electrically coupled to the operative element 36, e.g., by wires that extend through the interior of the handle 28 and catheter tube 30. The connector 42 plugs into the generator 38, to convey the generated energy to the operative element 36.

The system 24 also includes certain auxiliary processing equipment. In the illustrated embodiment, the processing equipment comprises an external fluid delivery apparatus 44 and an external aspirating apparatus 46.

The catheter tube 30 includes one or more interior lumens (not shown) that terminate in fittings 48 and 50, located on the handle 28. One fitting 40 connects to the fluid delivery apparatus 44, to convey processing fluid for discharge by or near the operative element 36. The other fitting 50 connects to the aspirating apparatus 46, to convey aspirated material from or near from the operative element 36 for discharge.

The system 24 also includes a controller 52. The controller 52, which preferably includes a central processing unit (CPU), is linked to the generator 38, the fluid delivery apparatus 44, and the aspirating apparatus 46. Alternatively, the aspirating apparatus 46 can comprise a conventional vacuum source typically present in a physician's suite, which operates continuously, independent of the controller 52.

The controller 52 governs the power levels, cycles, and duration that the radio frequency energy is distributed to the operative element 36, to achieve and maintain power levels appropriate to achieve the desired treatment objectives. In tandem, the controller 52 also governs the delivery of processing fluid and, if desired, the removal of aspirated material.

The controller 52 includes an input/output (I/O) device 54. The I/O device 54 allows the physician to input control and processing variables, to enable the controller to generate appropriate command signals. The I/O device 54 also receives real time processing feedback information from one or more sensors associated with the operative element (as will be described later), for processing by the controller 52, e.g., to govern the application of energy and the delivery of processing fluid. The I/O device 54 also includes a graphical user interface (GUI), to graphically present processing information to the physician for viewing or analysis. Further details regarding the GUI will be provided later.

B. Operative Elements

The structure of the operative element 36 can vary. Various representative embodiments will be described.

(i) Bipolar Devices

Figure 3:
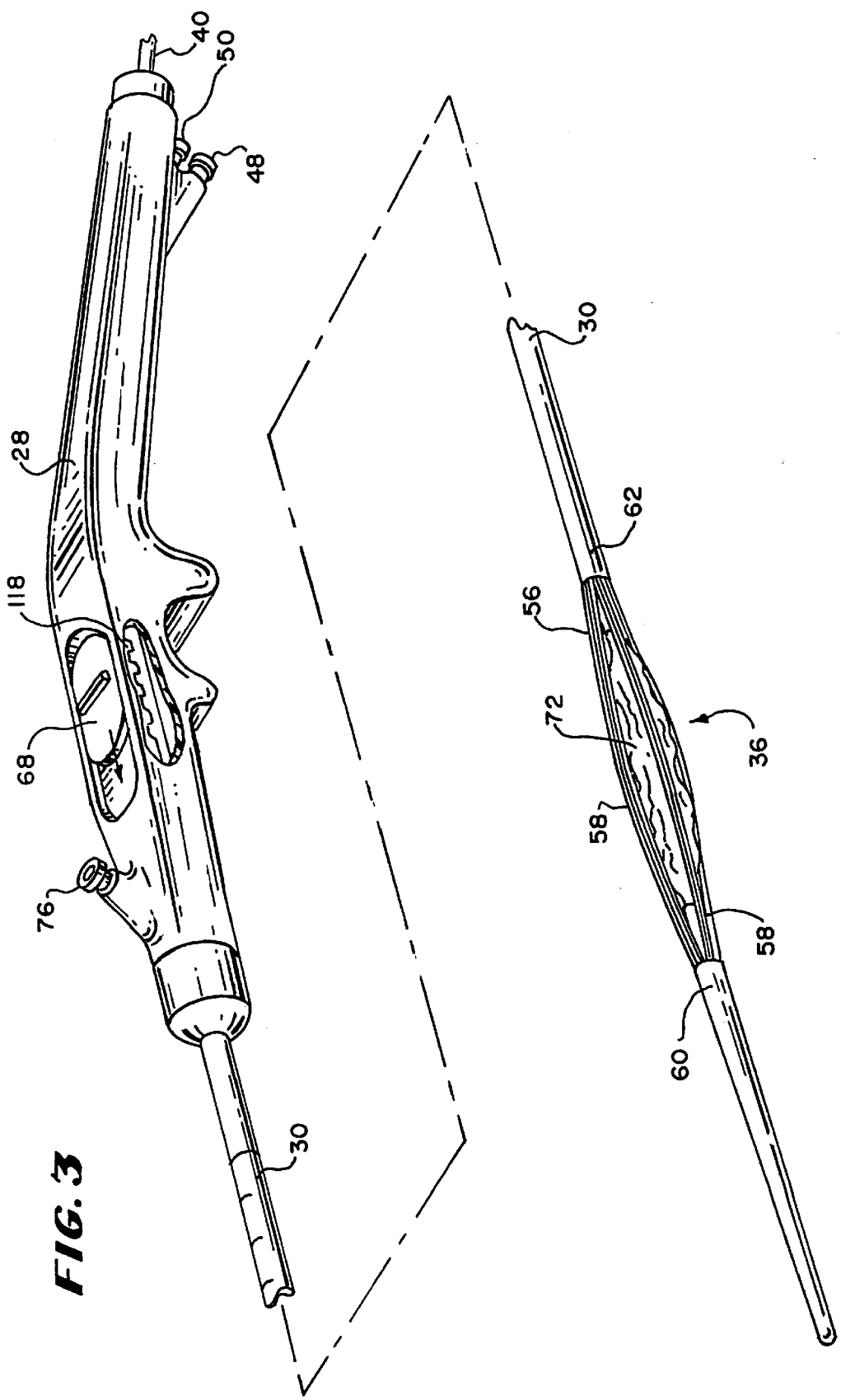
FIG. 3 is a perspective view, with portions broken away, of a device usable in association with the system shown in FIG. 1 having an operative element for contacting tissue shown in a collapsed condition.

In the embodiment shown in FIGS. 3 to 7, the operative element 36 comprises a three-dimensional basket 56. The basket 56 includes one or more spines 58, and typically includes from four to eight spines 58, which are assembled together by a distal hub 60 and a proximal base 62. In FIG. 3, the spines 58 are equally circumferentially spaced apart in side-by-side pairs.

Each spine 58 preferably comprises a flexible tubular body made, e.g. from molded plastic, stainless steel, or nickel titanium alloy. The cross sectional shape of the spines 58 can vary, possessing, e.g., a circular, elliptical, square, or rectilinear shape. In the illustrated embodiment, the spines 58 possess a rectilinear shape to resist twisting. Further examples of specific configurations for the spines 58 will be provided later.

Each spine 58 can be surrounded by a sleeve 64 (see FIG. 7) that is preferably textured to impart friction. Candidate materials for the sleeve 64 include knitted Dacron® material and Dacron® velour.

Figure 4:
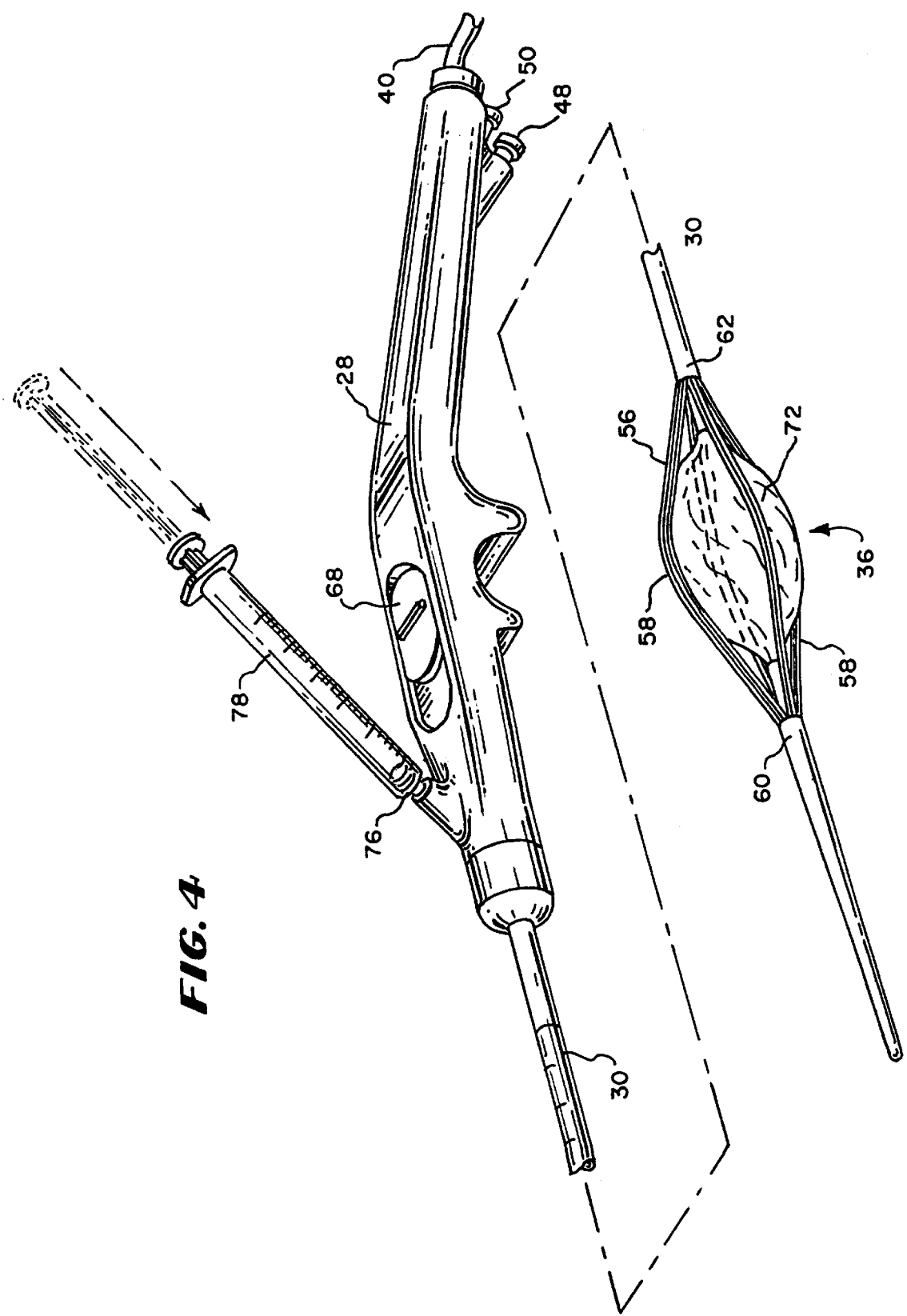
FIG. 4 is a perspective view, with portions broken away, of the device shown in FIG. 3, with the operative element shown in an expanded condition.
Figure 5:
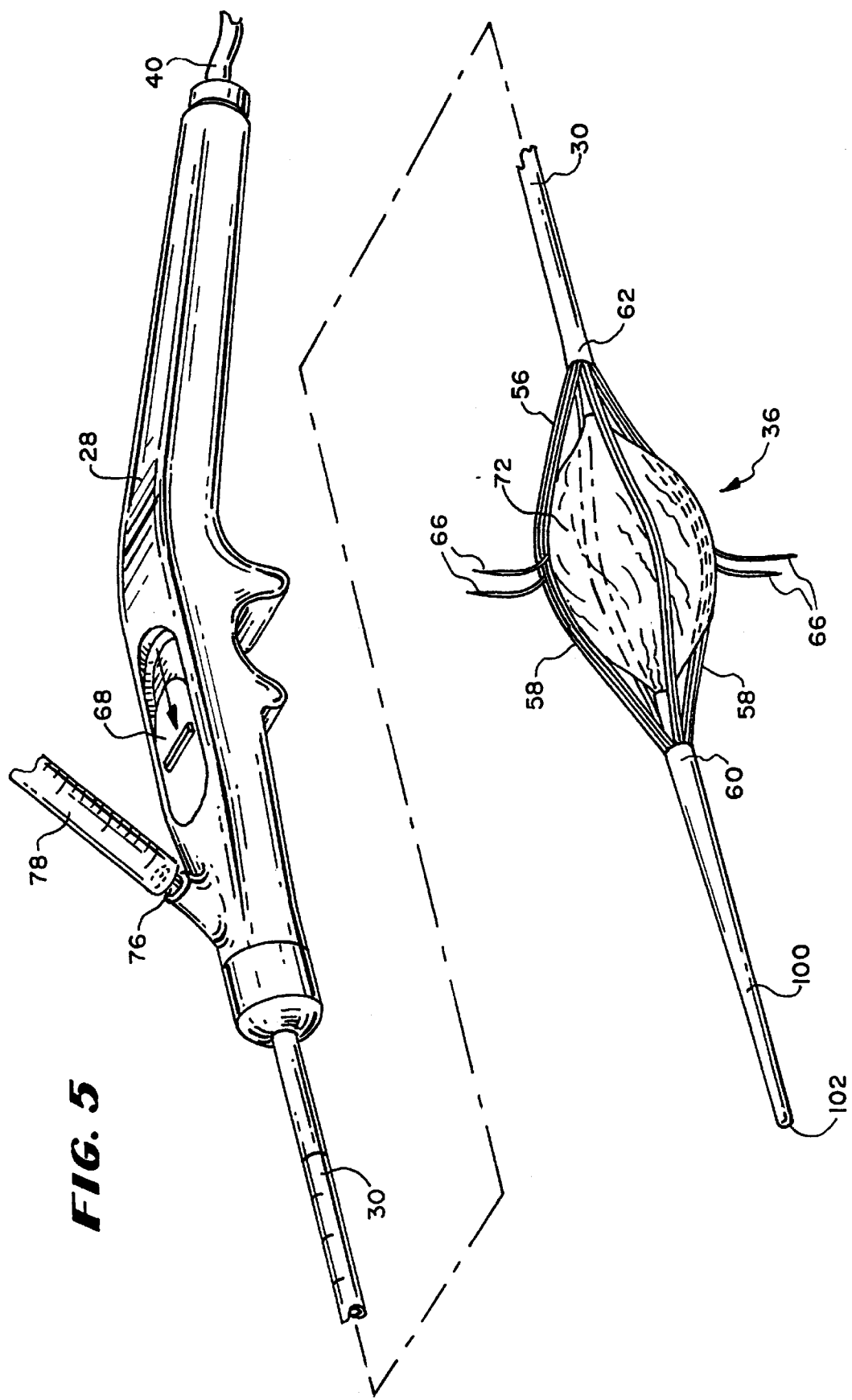
FIG. 5 is a perspective view, with portions broken away, of the device shown in FIG. 3, with the operative element shown in an expanded condition and the electrodes extended for use.

Each spine 58 carries an electrode 66 (see FIGS. 5 and 7). In the illustrated embodiment, each electrode 66 is carried within the tubular spine 58 for sliding movement. Each electrode 66 slides from a retracted position, withdrawn in the spine 58 (shown in FIGS. 3, 4, and 6), and an extended position, extending outward from the spine 58 (see FIGS. 5 and 7) through a hole in the spine 58 and sleeve 64.

A push-pull lever 68 on the handle 28 is coupled by one or more interior wires to the sliding electrodes 66. The lever 68 controls movement electrodes between the retracted position (by pulling rearward on the lever 68) and the extended position (by pushing forward on the lever 68).

The electrodes 66 can be formed from various energy transmitting materials. In the illustrated embodiment, for deployment in the esophagus 10 or cardia 20, the electrodes 66 are formed from nickel titanium. The electrodes 66 can also be formed from stainless steel, e.g., 304 stainless steel, or, as will be described later, a combination of nickel titanium and stainless steel. The electrodes 66 have sufficient distal sharpness and strength to penetrate a desired depth into the smooth muscle of the esophageal or cardia 20 wall. The desired depth can range from about 4 mm to about 5 mm.

To further facilitate penetration and anchoring in the esophagus 10 or cardia 20, each electrode 66 is preferably biased with a bend. Movement of the electrode 66 into the spine 58 overcomes the bias and straightens the electrode 66.

In the illustrated embodiment (see FIG. 5), each electrode 66 is normally biased with an antegrade bend (i.e., bending toward the proximal base 62 of the basket 56). Alternatively, each electrode 66 can be normally biased toward an opposite retrograde bend (i.e., bending toward the distal hub 60 of the basket 58).

As FIG. 7 shows, an electrical insulating material 70 is coated about the proximal end of each electrode 66. For deployment in the esophagus 10 or cardia 20, the length of the material 70 ranges from about 80 to about 120 mm. The insulating material 70 can comprise, e.g., a Polyethylene Terephthalate (PET) material, or a polyimide or polyamide material. For deployment in the esophagus 10 or cardia 20, each electrode 66 preferably presents an exposed, non-insulated conductive length of about 8 mm, providing an exposed surface area at the distal end of each electrode 66 of preferably about 0.1 $mm^2$ to 100 $cm^2$.

When the distal end of the electrode 66 penetrating the smooth muscle of the esophageal sphincter 18 or cardia 20 transmits radio frequency energy, the material 70 insulates the mucosal surface of the esophagus 10 or cardia 20 from direct exposure to the radio frequency energy. Thermal damage to the mucosal surface is thereby avoided. As will be described later, the mucosal surface can also be actively cooled during application of radio frequency energy, to further protect the mucosal surface from thermal damage.

The ratio between exposed and insulated regions on the electrodes 66 affects the impedance of the electrodes 66 during use. Generally speaking, the larger the exposed region is compared to the insulated region, a lower impedance value can be expected, leading to a fewer incidences of power shut-offs due to high impedance.

Of course, a greater or lesser number of spines 58 and/or electrodes 66 can be present, and the geometric array of the spines 58 and electrodes 66 can vary.

In the embodiment shown in FIG. 3, an expandable structure 72 comprising a balloon is located within the basket 56. The balloon structure 72 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material. Non-compliant materials offer the advantages of a predictable size and pressure feedback when inflated in contact with tissue. Compliant materials offer the advantages of variable sizes and shape conformance to adjacent tissue geometries.

The balloon structure 72 presents a normally, generally collapsed condition, as FIGS. 3 and 6 show). In this condition, the basket 56 is also normally collapsed about the balloon structure 72, presenting a low profile for deployment into the esophagus 10.

Figure 8:
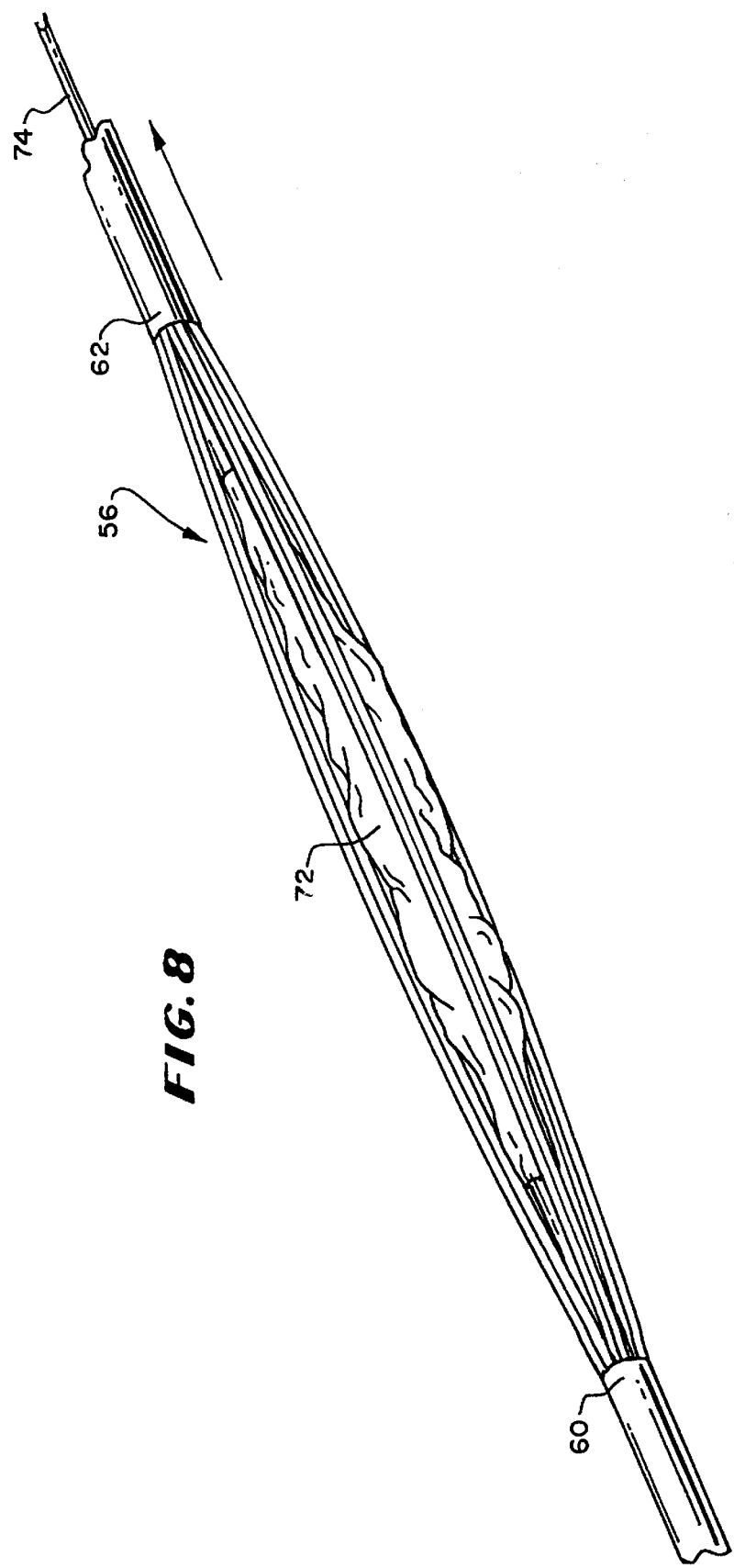
FIG. 8 is an enlarged perspective view of an embodiment the operative element, when fully collapsed.

To aid in the collapse of the basket 56 (see FIG. 8), one end (hub 60 or base 62) of the basket 56 can be arranged to slide longitudinally relative to the other end of the basket 56, which is accordingly kept stationary. A stylet 74 attached to the slidable end of the basket 56 (which, in FIG. 8, is the base 62) is controlled, e.g., by a push-pull mechanism on the handle 28. The stylet 74, when pulled, serves to move the ends 58 and 60 of the basket 56 apart when the balloon structure 72 is collapsed. A full collapse of the basket 56 is thereby possible (as FIG. 8 shows) to minimize the overall profile of the basket 56 for passage through the esophagus 10. The push-pull mechanism can include a lock to hold the stylet 74 stationary, to maintain the basket 56 in the fully collapsed condition during deployment.

The catheter tube 30 includes an interior lumen, which communicates with the interior of the balloon structure 72. A fitting 76 (e.g., a syringe-activated check valve) is carried by the handle 28. The fitting 76 communicates with the lumen. The fitting 76 couples the lumen to a syringe 78 (see FIGS. 4 and 5). The syringe 78 injects fluid under pressure through the lumen into the balloon structure 72, causing its expansion.

Expansion of the balloon structure 72 urges the basket 56 to open and expand (as FIGS. 4, 5, and 7 show). The force exerted by the balloon structure 72, when expanded, is sufficient to exert an opening force upon the tissue surrounding the basket 56. Preferably, for deployment in the esophagus 10 or cardia 20, the magnitude of the force exerted by the balloon structure 72 is between about 0.01 to 0.5 lbs.

For deployment in the lower esophageal sphincter 18, the diameter of the balloon structure 72, when expanded, can be optimized at about 2 cm to 3 cm. For deployment in the cardia 20, the diameter of the balloon structure 72, when expanded, can be optimized at about 4 cm to about 6 cm.

In the illustrated embodiment, the controller 52 conditions selected pairs of electrodes 66 to operate in a bipolar mode. In this mode, one of the electrodes comprises the transmitter and the other electrode comprises the return for the transmitted energy. The bipolar electrode pairs can comprise adjacent side-by-side electrodes 66 on a given spine, or electrodes 66 spaced more widely apart on different spines.

In the illustrated embodiment (see FIG. 7), each electrode 66 carries at least one temperature sensor 80. Each electrode can carry two temperature sensors 80, one to sense temperature conditions near the exposed distal end of the electrode 66, and the other to sense temperature conditions in the insulated material 70. Preferably, the second temperature sensor 80 is located on the corresponding spine 58, which rests against the muscosal surface when the balloon structure 72 is inflated.

In use (see FIGS. 9 to 19), the patient lies awake in a reclined or semi-reclined position. If used, the physician inserts the esophageal introducer 32 through the throat and partially into the esophagus 10. The introducer 32 is pre-curved to follow the path from the mouth, through the pharynx, and into the esophagus 10. The introducer 32 also includes a mouth piece 82, on which the patient bites to hold the introducer 32 in position. The introducer 32 provides an open, unobstructed path into the esophagus 10 and prevents spontaneous gag reflexes during the procedure.

As before explained, the physician need not use the introducer 32. In this instance, a simple mouth piece 82, upon which the patient bites, is used.

Figures 9, 10:
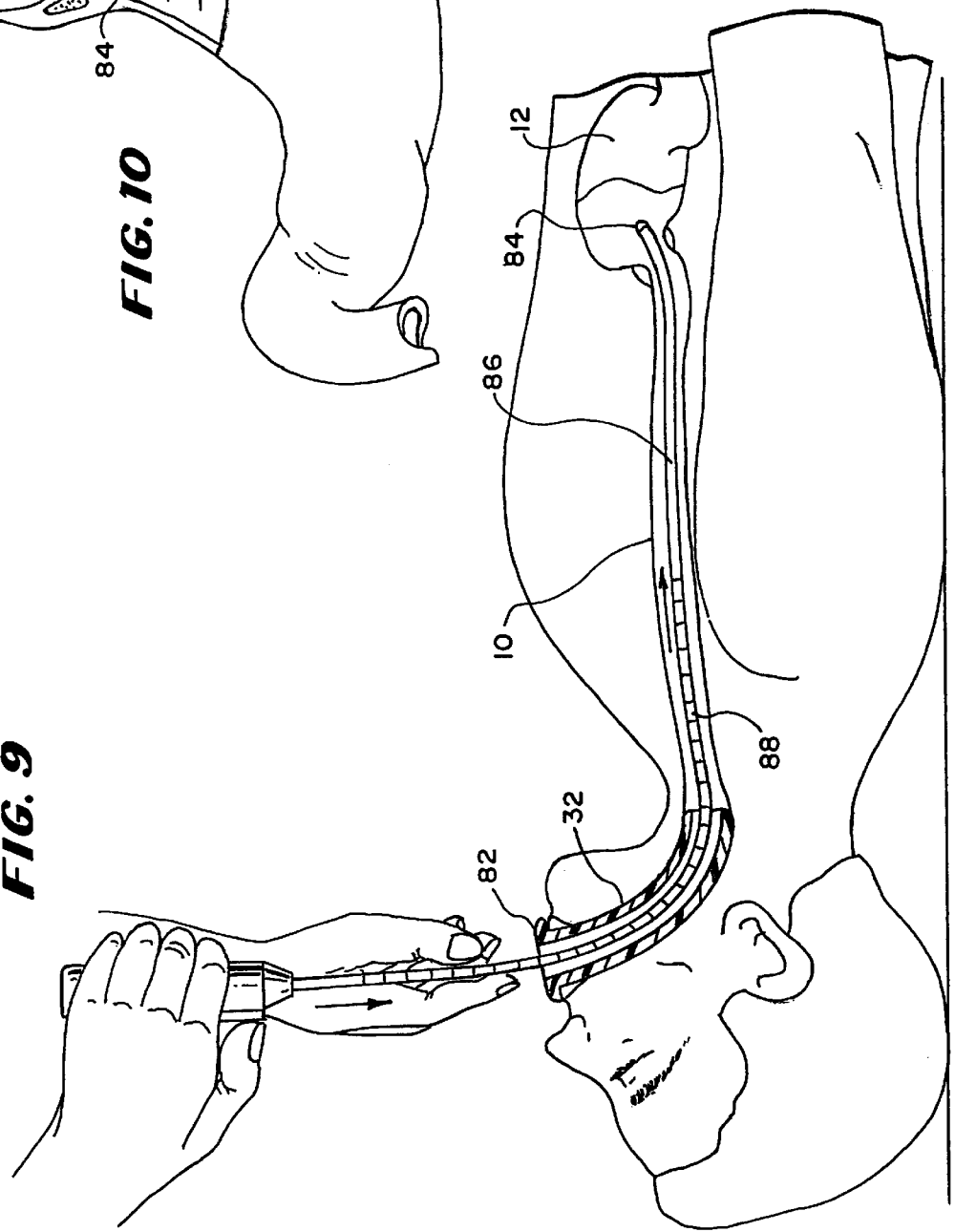
FIG. 9 is a side view of the deployment of a flexible endoscope through an esophageal introducer into the stomach.
FIG. 10 is an enlarged view of the endoscope shown in FIG. 9, retroflexed for viewing the cardia and lower esophageal sphincter.
Figure 13:
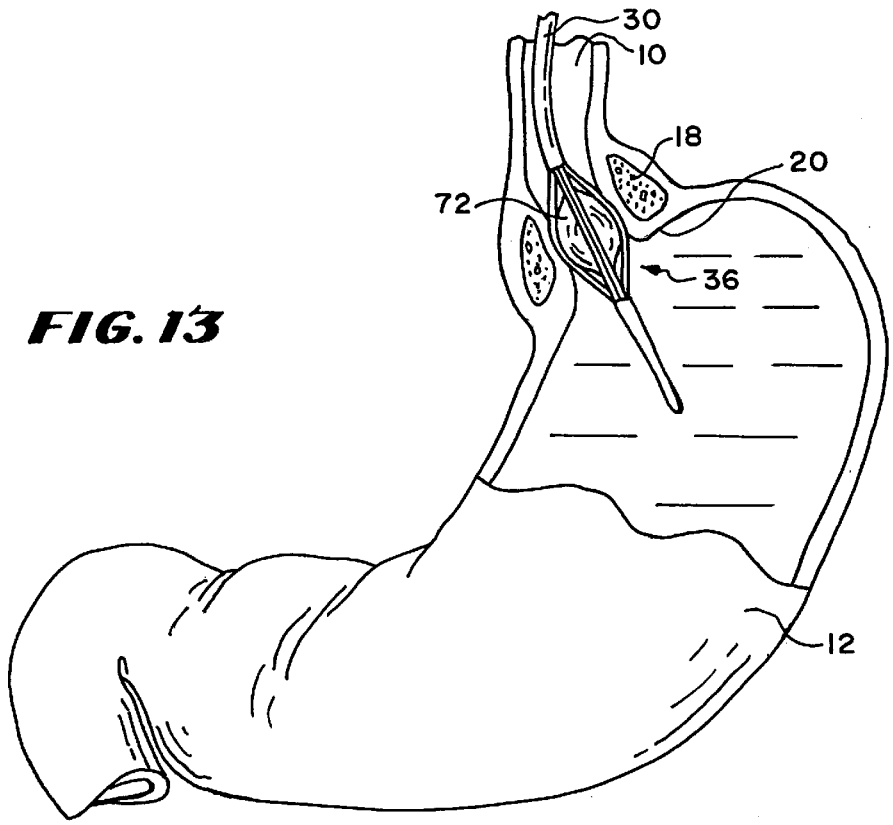
FIG. 13 is an enlarged view of the operative element shown in FIG. 11, when expanded into contact with mucosal tissue in the region of the lower esophageal sphincter.
Figure 14:
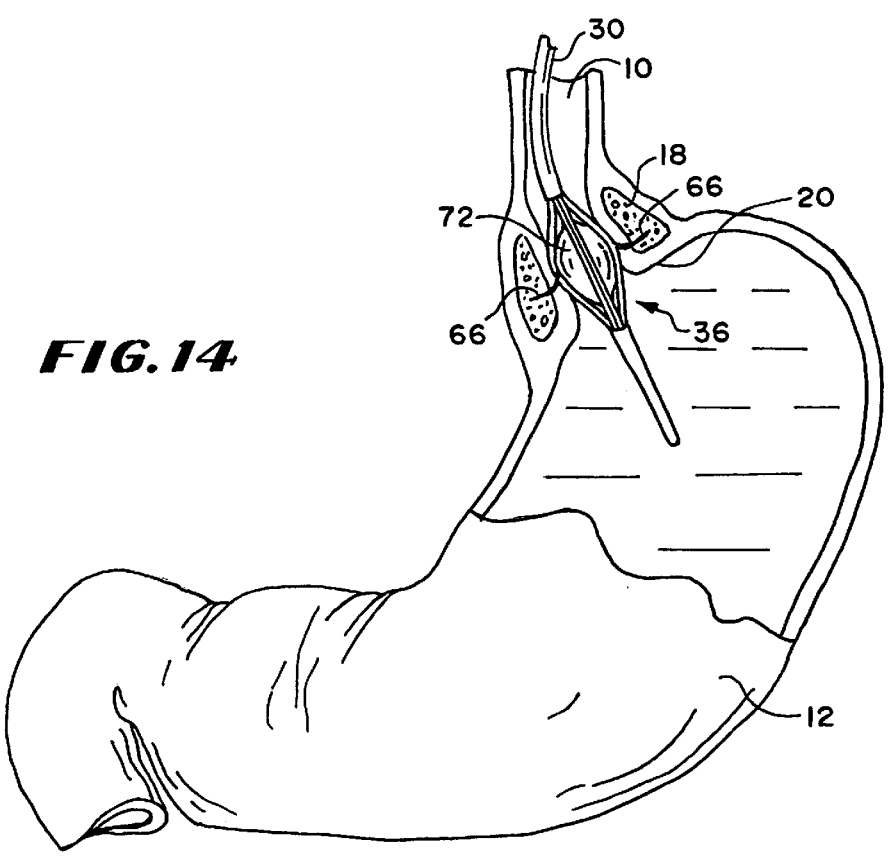
FIG. 14 is an enlarged view of the operative element shown in FIG. 11, when expanded into contact with mucosal tissue in the region of the lower esophageal sphincter and with the electrodes extended to create lesions in the smooth muscle ring of the lower esophageal sphincter.

The physician preferably first conducts a diagnostic phase of the procedure, to localize the site to be treated. As FIGS. 9 and 10 show, a visualization device can be used for this purpose. The visualization device can comprise an endoscope 84, or other suitable visualizing mechanism, carried at the end of a flexible catheter tube 86. The catheter tube 86 for the endoscope 84 includes measured markings 88 along its length. The markings 88 indicate the distance between a given location along the catheter tube 86 and the endoscope 84.

As FIGS. 9 and 10 show, the physician passes the catheter tube 86 through the patient's mouth and pharynx, and into the esophagus 10, while visualizing through the endoscope 84. Relating the alignment of the markings 88 to the mouth piece 82, the physician can gauge, in either relative or absolute terms, the distance between the patient's mouth and the endoscope 84 in the esophagus 10. When the physician visualizes the desired treatment site (lower esophageal sphincter 18 or cardia 20) with the endoscope 84, the physician records the markings 88 that align with the mouth piece 82.

The physician next begins the treatment phase of the procedure. As FIGS. 11 and 12 show, the physician passes the catheter tube 30 carrying the operative element 36 through the introducer 32. For the passage, the expandable balloon structure 72 is in its collapsed condition, and the electrodes 66 are in their retracted position. The physician can keep the endoscope 84 deployed for viewing the deployment of the operative element 36, either separately deployed in a side-by-side relationship with the catheter tube 30, or (as will be described later) by deployment through a lumen in the catheter tube 30 or deployment of the structure 72 through a lumen in the endoscope 84 itself. If there is not enough space for side-by-side deployment of the endoscope 84, the physician deploys the endoscope 84 before and after deployment of the structure 72.

In the illustrated embodiment, the catheter tube 30 includes measured markings 90 along its length. The measured markings 90 indicate the distance between a given location along the catheter tube 30 and the operative element 36. The markings 90 on the catheter tube 30 correspond in spacing and scale with the measured markings along the endoscope catheter tube 86. The physician can thereby relate the markings 90 on the catheter tube 30 to gauge, in either relative or absolute terms, the location of the operative element 36 inside the esophagus 10. When the markings 90 indicate that the operative element 36 is at the desired location (earlier visualized by the endoscope 84), the physician stops passage of the operative element 36. The operative element 36 is now located at the site targeted for treatment.

Figure 15:
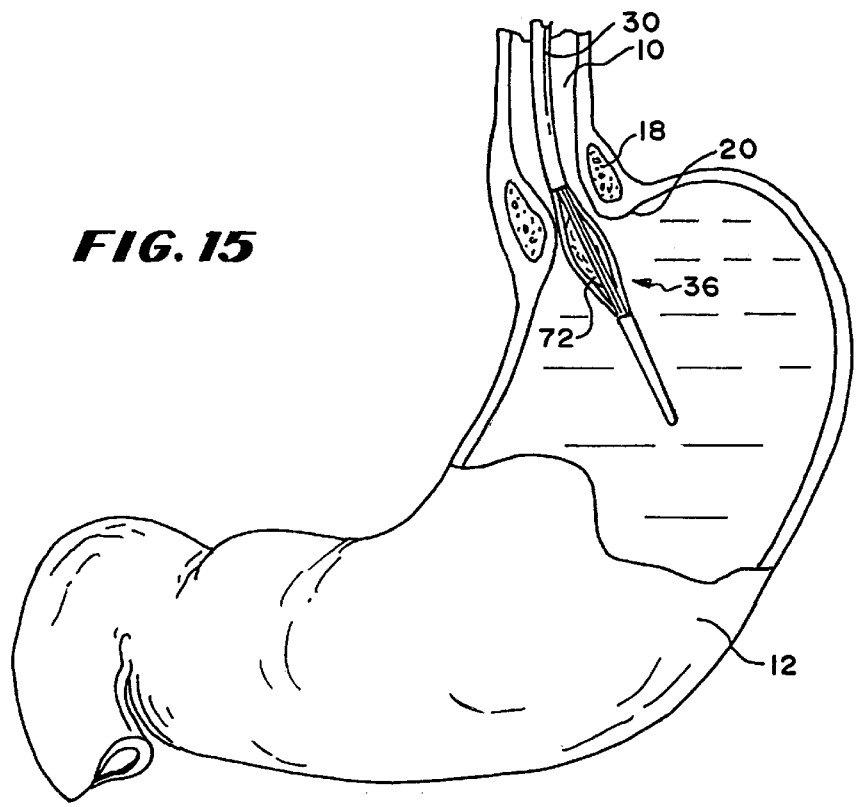
FIG. 15 is an enlarged view of the operative element shown in FIG. 11, when placed in the region of the cardia.

In FIG. 12, the targeted site is shown to be the lower esophageal sphincter 18. In FIG. 15, the targeted site is shown to be the cardia 20 of the stomach 12.

Figure 16:
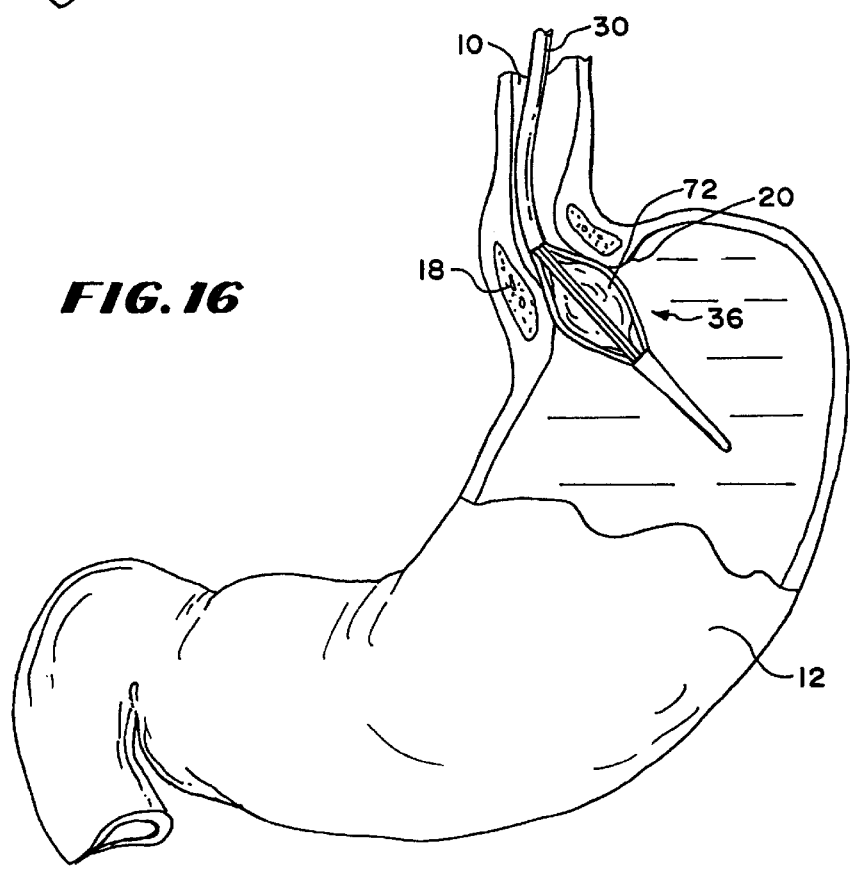
FIG. 16 is an enlarged view of the operative element shown in FIG. 11, when expanded into contact with muscosal tissue in the cardia.

Once located at the targeted site, the physician operates the syringe 78 to convey fluid or air into the expandable balloon structure 72. The structure 72, and with it, the basket 56, expand, to make intimate contact with the mucosal surface, either with the sphincter (see FIG. 13) or the cardia 20 (FIG. 16). The expanded balloon structure 72 serves to temporarily dilate the lower esophageal sphincter 18 or cardia 20, to remove some or all the folds normally present in the mucosal surface. The expanded balloon structure 72 also places the spines 58 in intimate contact with the mucosal surface.

Figure 17:
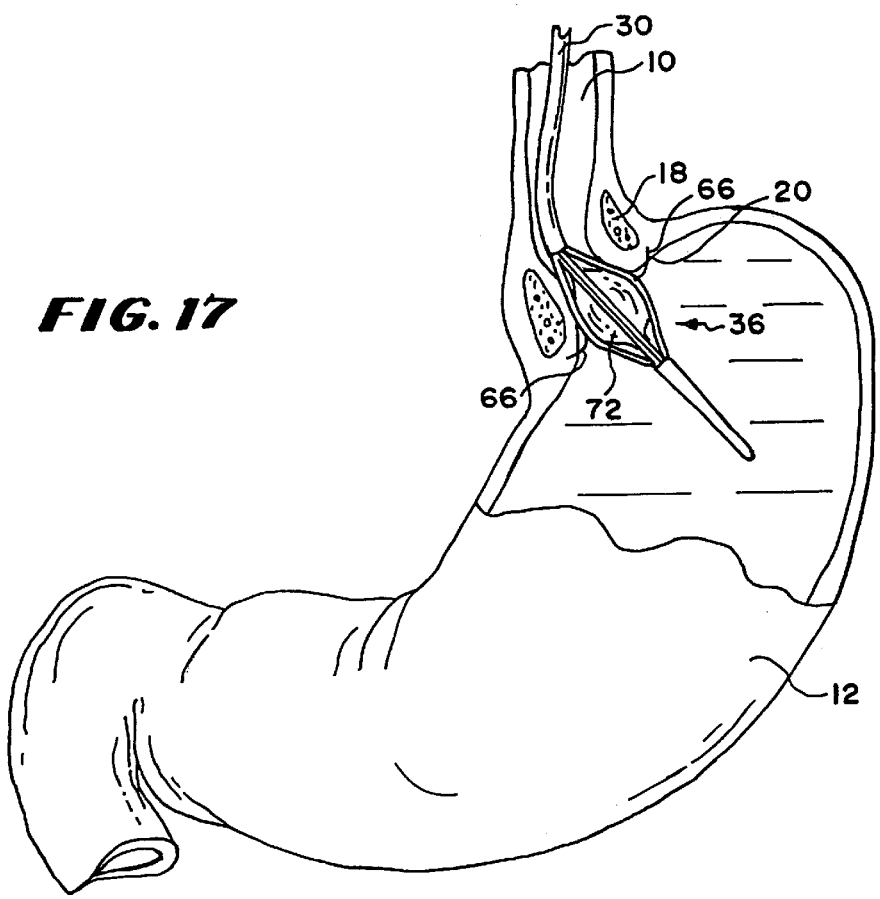
FIG. 17 is an enlarged view of the operative element shown in FIG. 11, when expanded into contact with muscosal tissue in the cardia and with the electrodes extended to create lesions in the smooth muscle of the cardia.
Figure 18:
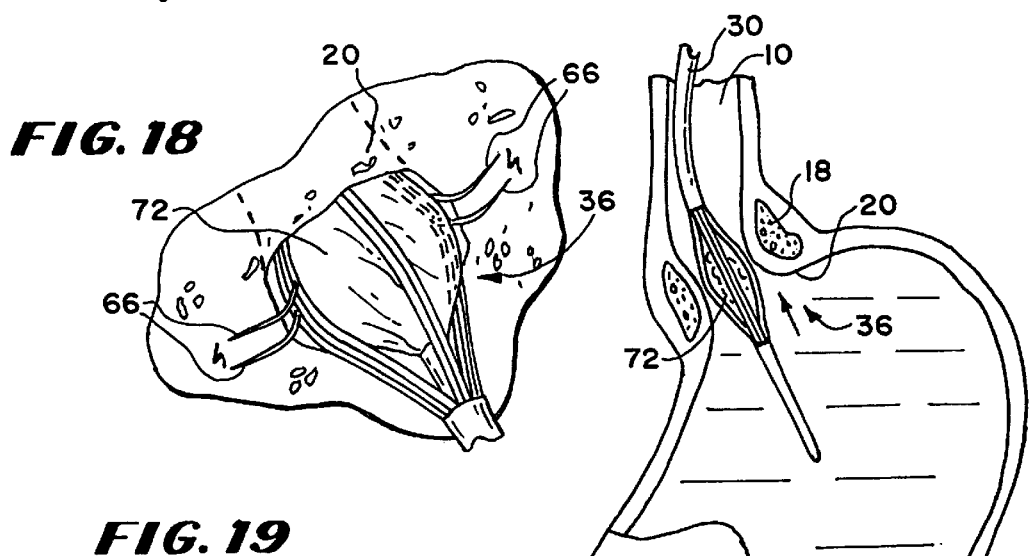
FIG. 18 is an enlarged view of the operative element shown in FIG. 17, when fully deployed for creating lesions in the cardia.
Figure 19:
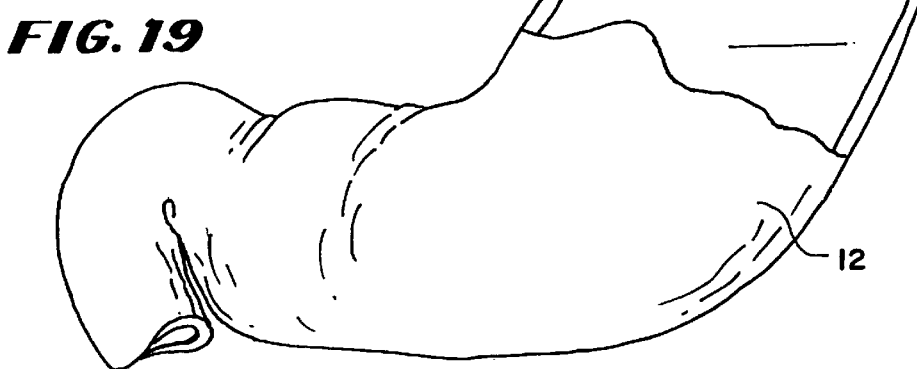
FIG. 19 is an enlarged view of the operative element shown in FIG. 14 or FIG. 17, after being used to form lesions and in the process of being removed from the targeted tissue site.

The physician pushes forward on the lever 68 to move the electrodes 66 into their extended position. The electrodes 66 pierce and pass through the mucosal tissue into the smooth muscle tissue of the lower esophageal sphincter 18 (FIG. 14) or cardia 20 (FIGS. 17 and 18).

The physician commands the controller 52 to apply radio frequency energy between the transmitting and receiving electrodes 66 in each pair. The energy can be applied simultaneously by all pairs of electrodes 66, or in any desired sequence.

The energy ohmically heats the smooth muscle tissue between the transmitting and return electrodes 66. The controller 52 samples temperatures sensed by the sensors 80 to control the application of energy. When each electrode 66 in a given pair carries at least one temperature sensor 80, the controller 52 can average the sensed temperature conditions or select the maximum temperature condition sensed for control purposes.

The controller 52 processes the sensed temperatures in a feedback loop to control the application of energy. The GUI can also display the sensed temperatures and the applied energy levels. Alternatively, the physician can manually control the energy levels based upon the temperature conditions displayed on the GUI.

Preferably, for a region of the lower esophageal sphincter 18 or cardia 20, energy is applied to achieve tissue temperatures in the smooth muscle tissue in the range of 55° C. to 95° C. In this way, lesions can typically be created at depths ranging from one to four millimeters below the muscosal surface. Typical energies range, e.g., between 100 and 1000 joules per electrode pair.

It is desirable that the lesions possess sufficient volume to evoke tissue healing processes accompanied by intervention of fibroblasts, myofibroblasts, macrophages, and other cells. The healing processes results in a contraction of tissue about the lesion, to decrease its volume or otherwise alter its biomechanical properties. The healing processes naturally tighten the smooth muscle tissue in the sphincter 18 or cardia 20. The bipolar nature of the energy path between the electrodes 66 creates, for a given amount of energy, lesions of greater volume than is typically created in a monopolar fashion.

To create greater lesion density in a given targeted tissue area, it is also desirable to create a pattern of multiple lesions, e.g., in rings along the targeted treatment site in the lower esophageal sphincter 18 or cardia 20.

Various lesion patterns 92 can be achieved. A preferred pattern (shown in FIG. 20 for the cardia 20) comprises several rings 94 of lesions 96 about one centimeter apart, each ring 94 comprising at least eight lesions 96. For example, a preferred pattern 92 comprise six rings 94, each with eight lesions 96. In the cardia 20, as FIG. 20 shows, the rings 94 are concentrically spaced about the opening funnel of the cardia 20. In the lower esophageal sphincter 18, the rings 94 are axially spaced along the esophagus 10.

The physician can create a given ring pattern 92 by expanding the balloon structure 72 and extending the electrodes 66 at the targeted treatment site, to form a first set of four lesions. The physician then withdraws the electrodes 66, collapses the balloon structure 72, and rotates the catheter tube 30 by a desired amount. The physician then again expands the structure 72 and again extends the electrodes 66, to achieve a second set of four lesions. The physician repeats this sequence until a desired ring 94 of lesions 96 is formed. Additional rings 94 of lesions 96 can be created by advancing the operative element axially, gauging the ring separation by the markings 90 on the catheter tube 30.

Other, more random or eccentric patterns of lesions can be formed to achieve the desired density of lesions within a given targeted site.

The bipolar operative element 36 can be used in the manner described to treat both the cardia 20 and the lower esophageal sphincter 18 in a single procedure. Alternatively, the operative element 36 can be used in the manner described to treat either the cardia 20 or the lower esophageal sphincter 18 individually.

In one embodiment, at least one spine 58 (and preferably all spines) includes an interior lumen 98 (see FIG. 7). The fluid delivery apparatus 44 conveys processing fluid F through the lumen 98 for discharge at the treatment site. The processing fluid F can comprise, e.g., saline or sterile water, to cool the mucosal surface while energy is being applied by the electrode 66 to ohmically heat muscle beneath the surface.

In this arrangement (see FIG. 5), the catheter tube 30 includes a distal tail 100, which extends beyond the hub 60 of the basket 56. An interior lumen 102 extends through the tail 100 and the interior of the balloon structure 72 to connect to the fitting 48. The aspirating apparatus 46 draws aspirated material and the processing fluid through this lumen 102 for discharge. This arrangement provides self-contained aspiration for the operative element 36.

In an alternative embodiment suited for treatment of the lower esophageal sphincter 18 outside the stomach 12 (see FIG. 11), the mouth piece 82 of the esophageal introducer 32, if used, includes an aspiration port 104. The aspiration apparatus 46 is coupled to this port 104. In this arrangement, processing fluid introduced at the treatment site is drawn through the introducer 32 surrounding the catheter tube 30 and into the aspiration apparatus 46 for discharge. In this embodiment, the operative element 36 need not include the self contained, interior aspiration lumen 102.

(ii) Structures Shaped for the Cardia

As FIG. 1 shows, the cardia 20 presents a significantly different topology than the lower esophageal sphincter 18. First, the surface area of the cardia 20 is larger than the lower esophageal sphincter 18. Second, the surface area of the cardia 20 expands with distance from the lower esophageal sphincter 18. The cardia 20 is therefore "funnel" shaped, compared to the more tubular shape of the lower esophageal sphincter 18.

The different topologies can be accommodated by using a family of operative elements having different shapes. One such operative element has a size and geometry better suited for deployment in the lower esophageal sphincter 18 than the cardia 20, if desired). Another such operative element has a larger size and different geometry better suited for deployment in the cardia 20 than the lower esophageal sphincter. However, it is preferred to provide a single operative element that can be effectively deployed in both regions.

The location and the orientation of optimal, intimate contact between an operative element: and the targeted tissue also differ in the cardia 20, compared to the lower esophageal sphincter 18. In the lower esophageal sphincter 18, optimal, intimate contact occurs generally about the mid-region of the operative element, to thereby conform to the generally tubular shape of the sphincter 18. In the cardia 20, optimal, intimate contact occurs generally more about the proximal end of operative device, to thereby conform to the funnel shape of the cardia 20.

(a) Proximally Enlarged, Shaped Structures

FIGS. 21 to 23 show an operative element 106 having a shaped geometry and electrode configuration well suited for use in the cardia 20. The operative element 106 shares many features of the operative element 36 shown in FIG. 5, and common reference numbers are thus assigned.

Like the previously described element 36, the operative element 106 comprises an array of spines 58 forming a basket 56, which is carried at the distal end of a catheter tube 30. Like the previously described element 36, the operative element 106 includes electrodes 66 on the spines 58 that can be retracted (FIG. 21) or extended (FIG. 22). As illustrated, the electrodes 66 are likewise bent in an antegrade direction.

Like the previously described element 36, the operative element 106 includes an inner balloon structure 72 that expands to open the basket 56 and place it in intimate contact with the cardia 20 for extension of the electrodes 66.

The balloon structure 72, when expanded, as shown in FIG. 22, possesses a preformed shape achieved e.g., through the use of conventional thermoforming or blow molding techniques. The structure 72 possesses a "pear" shape, being more enlarged at its proximal end than at its distal end. This preformed pear shape presents an enlarged proximal surface for contacting the cardia 20 (see FIG. 23). The preformed pear shape better conforms to the funnel shaped topography of the cardia 20 than a circular shape. The pear shape, when in intimate contact with the cardia 20, establishes a secure anchor point for the deployment of the electrodes 66.

Figure 24:
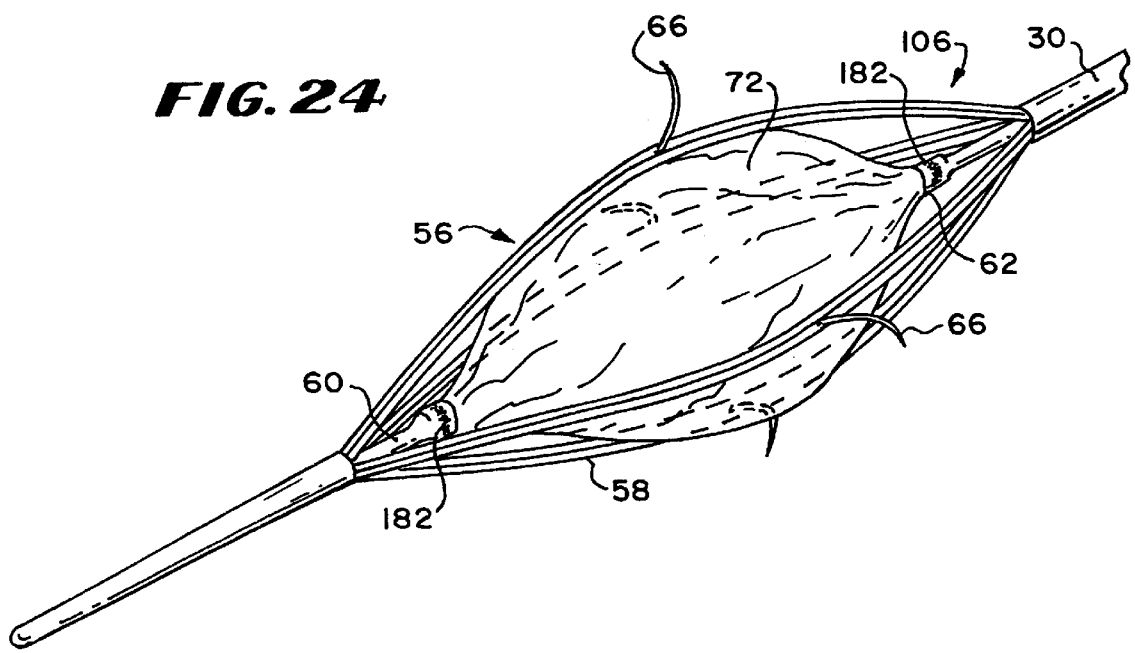
FIG. 24 is a perspective view of the "pear-shaped" shown in FIG. 21, shown in an expanded condition with the electrodes extended for use in a retrograde orientation.

As also shown in FIGS. 22 and 23, the electrodes 66 themselves are repositioned to take advantage of the pear shape of the underlying balloon structure 72. The electrodes 66 are positioned proximally closer to the enlarged proximal base of the structure 72 than to its distal end. As FIGS. 24 and 25 show, the proximally located electrodes 66 can also be bent in a retrograde bent direction on the pear-shaped element 106.

Figure 25:
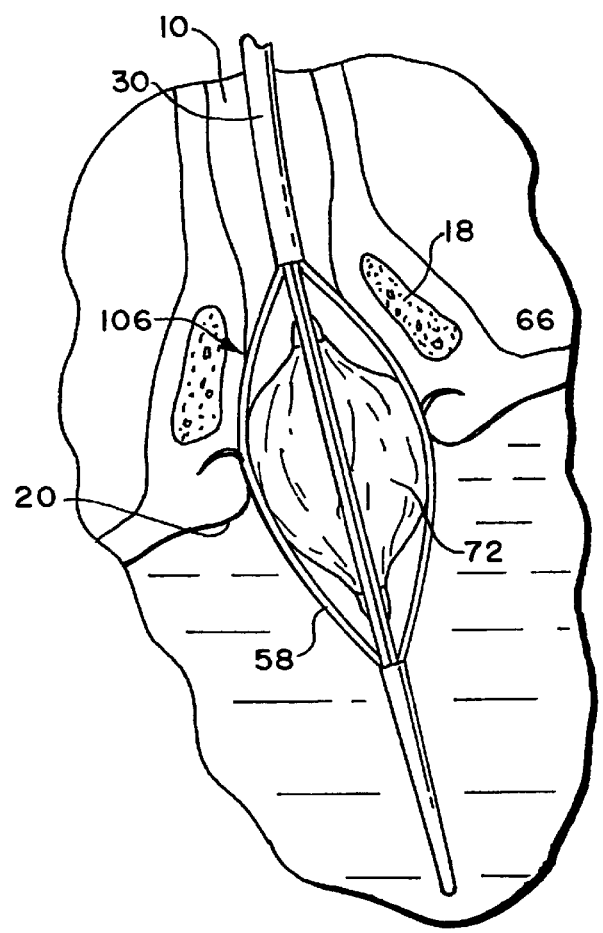
FIG. 25 is an enlarged view of the operative element shown in FIG. 24, when expanded into contact with muscosal tissue in the cardia and with the electrodes extended to create lesions in the smooth muscle of the cardia.

In use (as FIGS. 23 and 25 show), the physician deploys the operative element 106 into the stomach 12. The physician expands the element 106 and then pulls rearward on the catheter tube 30. This places the enlarged proximal base of the structure 106 in contact with the cardia 20. The physician next extends the electrodes 66 into the cardia 20 and proceeds with the ablation process. Multiple lesion patterns can be created by successive extension and retraction of the electrodes, accompanied by rotation and axial movement of the catheter tube 30 to reposition the structure 106.

If enough space is present, the physician can retroflex an endoscope, also deployed in the stomach 12, to image the cardia 20 as deployment of the electrodes 66 and lesion formation occur. Typically, however, there is not enough space for side-by-side deployment of the endoscope, and the physician views the cardia 20 before and after the lesion groups are formed.

As FIGS. 23 and 25 show, the purposeful proximal shaping of the operative element 106 and the proximal location of the antegrade or retrograde electrodes 66 make the operative element 106 well suited for use in the cardia 20.

In FIGS. 22 and 24, the electrodes 66 are not arranged in bipolar pairs. Instead, for purposes of illustration, the electrodes 66 are shown arranged in singular, spaced apart relation. In this arrangement, the electrodes 66 are intended for monopolar operation. Each electrode 66 serves as a transmitter of energy, and an indifferent patch electrode (not shown) serves as a common return for all electrodes 66. It should be appreciated, however, the operative element 106 could include bipolar pairs of electrodes 66 as shown in FIG. 5, if desired.

(b) Disk Shaped Expandable Structures

Figure 26:
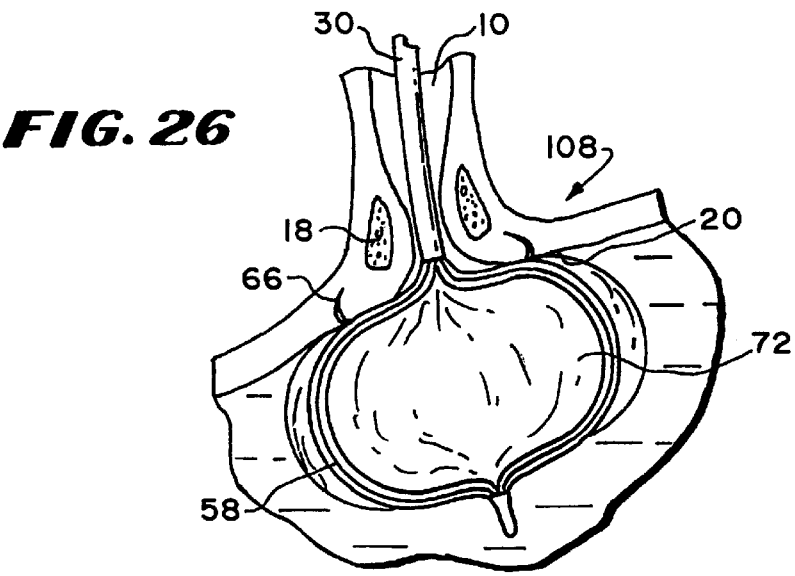
FIG. 26 is an enlarged side view a "disk-shaped" operative element intended for deployment in the cardia, when expanded into contact with muscosal tissue in the cardia and with the electrodes extended to create lesions in the smooth muscle of the cardia.

FIG. 26 shows another operative element 108 shaped for deployment in the cardia 20. This element 108 shares many features with the element 36 shown in FIG. 5, and common reference numbers have also been assigned.

In FIG. 26, the expandable balloon structure 72 within the element 108 has been preformed, e.g., through the use of conventional thermoforming or blow molding techniques, to present a disk or donut shape. The disk shape also provides an enlarged proximal surface for contacting the cardia 20, to create a secure anchor for the deployment of the electrodes 66.

The physician deploys the operative element 108 into the stomach 12, preferably imaging the cardia 20 as deployment occurs. The physician expands the disk-shaped element 108 and pulls rearward on the catheter tube 30, to place the element 108 in contact with the cardia 20. The physician extends the electrodes into the cardia 20 and proceeds with the ablation process. Lesion patterns are formed by successive extension and retraction of the electrodes 66, accompanied by rotation and axial movement of the catheter tube 30.

As FIG. 26 shows, antegrade bent electrodes 66 are proximally mounted about the disk-shaped expandable element 108. Retrograde bent electrodes could also be deployed.

(c) Complex Shaped Structures Providing Multiple Anchor Points

Figure 27:
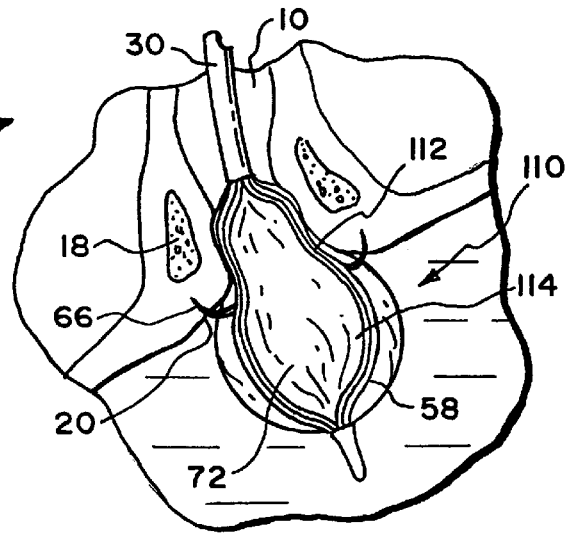
FIGS. 27 and 28 are an enlarged side views operative elements having different "peanut" shapes intended for deployment in the cardia, when expanded into contact with muscosal tissue in the cardia and with the electrodes extended to create lesions in the smooth muscle of the cardia.
Figure 28:
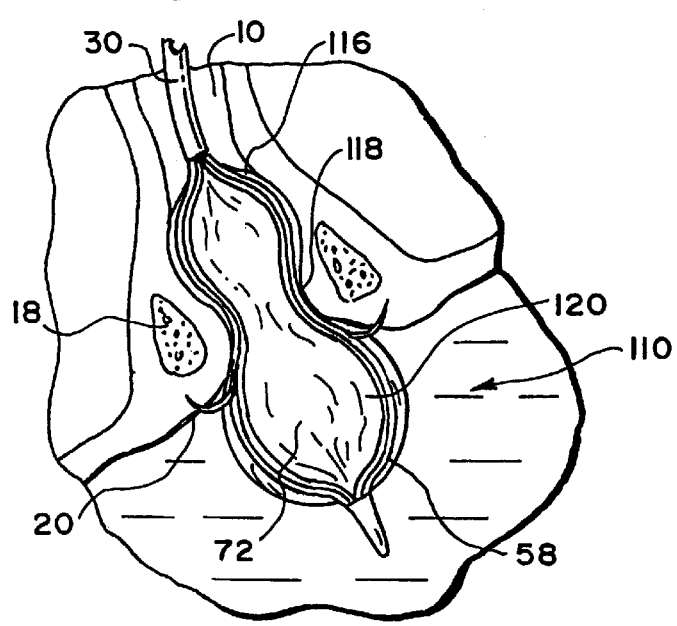

FIGS. 27 and 28 show another operative element 110 having a geometry well suited for deployment in the cardia 20. The balloon structure 72 within the element 110 is preformed, e.g., through the use of conventional thermoforming or blow molding techniques, to possesses a complex peanut shape. The complex shape provides multiple surface contact regions, both inside and outside the cardia 20, to anchor the element 110 for deployment of the electrodes 66.

In FIG. 27, a reduced diameter portion 112 of the expanded structure 72 contacts the lower esophageal sphincter region. A larger diameter main portion 114 of the expanded structure 72 rests in intimate contact against the cardia 20 of the stomach 12.

In an alternative peanut shaped configuration (see FIG. 28), the structure 72 includes a first reduced diameter portion 116 to contact the esophagus 10 above the lower esophageal sphincter 18. The structure 72 includes a second reduced portion 118 to contact the lower esophageal sphincter 18 region of the esophagus 10. The structure includes a third, larger diameter main portion 120 to rest in intimate contact against the cardia 20 of the stomach 12.

The peanut shaped configurations shown in FIGS. 27 and 28 provide multiple points of support for operative element 110 both inside and outside the stomach 12, to thereby stabilize the electrodes.

In FIGS. 27 and 28, antegrade bent electrodes 66 are shown deployed in the cardia 20. Retrograde bent electrodes could also be deployed.

C. The Electrodes

(i) Electrode Shapes

Regardless of the shape of the operative element and its region of deployment in the body, the electrodes 66 can be formed in various sizes and shapes. As FIG. 30 shows, the electrodes 66 can possess a circular cross sectional shape. However, the electrodes 66 preferably possess a cross section that provides increased resistance to twisting or bending as the electrodes penetrate tissue. For example, the electrodes 66 can possess a rectangular cross section, as FIG. 32 shows. Alternatively, the electrodes 66 can possess an elliptical cross section, as FIG. 31 shows. Other cross sections, e.g., conical or pyramidal, can also be used to resist twisting.

The surface of the electrode 66 can, e.g., be smooth, or textured, or concave, or convex. The preceding description describes electrodes 66 bent in either an antegrade or retrograde direction over an arc of ninety degrees or less. The bend provides a secure anchorage in tissue. Retraction of the electrodes 66 into the spines 58 overcomes the bias and straightens the electrode 66 when not in use.

In FIG. 29, the electrode 66 is biased toward a "pig-tail" bend, which spans an arc of greater than ninety degrees. The increased arc of the bend enhances the tissue-gripping force, thereby providing a more secure anchorage in tissue. As before, retraction of the electrodes 66 into the spines 58 overcomes the bias and straightens the electrode 66 when not in use.

A given electrode 66 can comprise a hybrid of materials, e.g., stainless steel for the proximal portion and nickel titanium alloy for the distal portion. The nickel titanium alloy performs best in a curved region of the electrode 66, due to its super-elastic properties. The use of stainless steel in the proximal portion can reduce cost, by minimizing the amount of nickel titanium alloy required.

The different materials may be joined, e.g., by crimping, swaging, soldering, welding, or adhesive bonding, which provide electrical continuity between or among the various materials.

One or both of the materials may be flattened to an oval geometry and keyed together to prevent mutual twisting. In a preferred embodiment, the proximal portion comprises an oval stainless steel tube, into which a distal curved region having a round cross section and made of nickel titanium is slipped and keyed to prevent mutual twisting.

(ii) Electrode Penetration Depth

The depth of electrode penetration can also be controlled, to prevent puncture through the targeted tissue region.

In one embodiment, the push-pull lever 68 on the handle 28, which controls movement electrodes 66, can include a rachet 118 or detent mechanism (see FIG. 3) that provides a tactile indication of electrode advancement. For each click of the rachet mechamism 118 as the lever 68 is moved forward or rearward, the physician knows that the electrodes have traveled a set distance, e.g., 1 mm.

Alternatively, or in combination, the electrode 66 can carry a limit collar 121 (see FIG. 33). The limit collar 121 contacts surface tissue when a set maximum desired depth of electrode penetration has been reached. The contact between the collar 121 and surface tissue resists further advancement of the electrode 66. The physician senses the contact between the collar 121 and surface tissue by the increased resistance to movement of the lever 68. The physician thereby knows that the maximum desired depth of tissue penetration has been reached and to extend the electrodes 66 no further.

An electrical measurement can also be made to determine penetration of an electrode 66 in tissue. For example, by applying electrical energy at a frequency (e.g., 5 kHz) less than that applied for lesion formation, impedance of a given electrode 66 can be assessed. The magnitude of the impedance varies with the existence of tissue penetration and the depth of tissue penetration. A high impedance value indicates the lack of tissue penetration. The impedance value is lowered to the extent the electrode penetrates the tissue.

(iii) Movement of Electrodes

As before described, it is desirable to be able to create a pattern of multiple lesions to create greater lesion density. The previous discussions in this regard were directed to achieving these patterns by successive extension and retraction of the electrodes 66, accompanied by rotation and axial movement of the catheter tube 30.

Figure 34:
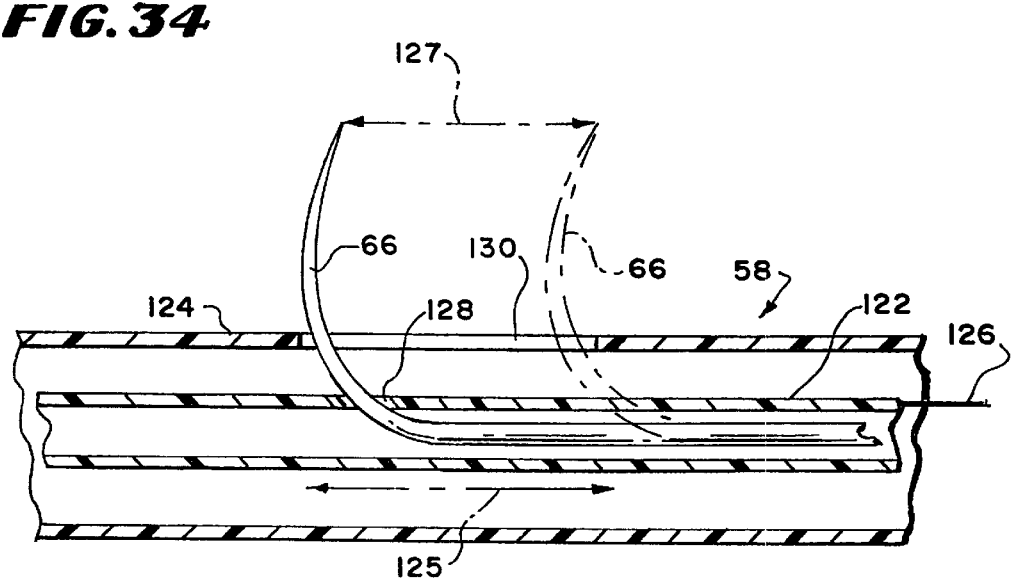
FIG. 34 is a side section view of a stationary spine which comprises a portion of an operative element and which carries a movable electrode for creating lesion patterns.

An alternative embodiment is shown in FIG. 34, which achieves creation of lesion patterns movement without axial and, if desired, rotational movement of the catheter tube 30. In this embodiment, the basket 56 has an array of spines 58, as generally shown, e.g., in FIG. 22 or 24. As FIG. 34 shows, each spine 58 in the alternative embodiment includes an inner carrier 122 mounted for axial sliding movement within a concentric outer sleeve 124. In this arrangement, a push-pull stylet 126 controlled by another lever on the handle (not shown) axially moves the carrier 122 within the outer sleeve 124 (as shown by arrows 125 in FIG. 34).

A tissue penetrating electrode 66 of the type already described is supported by the carrier 122. The electrode 66 can be moved by the operator (using the handle-mounted lever 68, as shown in FIG. 5) from a retracted position within the carrier 122 and an extended position, projecting from a guide hole 128 in the carrier 122 (which FIG. 34 shows). When in the extended position, the electrode 66 also projects through a window 130 in the outer sleeve 124 for tissue penetration. The window 130 has a greater axial length than the guide hole 128. The extended electrode 66 can thereby be moved by moving the carrier 122 (as shown by arrows 127 in FIG. 34) and thereby positioned in a range of positions within the window 130.

For example, in use, the physician moves the carrier 122 so that the guide hole 128 is aligned with the leading edge of the window 130. The push-pull stylet 126 can be controlled, e.g., with a detent mechanism that stops forward advancement or otherwise gives a tactile indication when this alignment occurs. External markings on the handle can also visually provide this information. The physician moves the electrodes 66 into their respective extended position, to penetrate tissue. After energy sufficient to form a first ring pattern of lesions is applied, the physician withdraws the electrodes 66 into the carriers 122.

The physician now moves the electrodes 66 axially rearward, without moving the catheter tube 30, by pulling the push-pull stylet 126 rearward. If desired, the physician can rotate the catheter tube 30 to achieve a different circumferential alignment of electrodes 66. The detent mechanism or the like can click or provide another tactile indication that the guide hole 128 in each spine is aligned with a mid portion of the respective window 130. Markings on the handle can also provide a visual indication of this alignment. The physician extends the electrodes 66 through the window 130. This time, the electrode 66 penetrate tissue in a position axially spaced from the first ring of penetration. Energy is applied sufficient to form a second ring pattern of lesions, which likewise are axially spaced from the first ring. The physician withdraws the electrodes 66 into the carriers.

The physician can now move the carriers 122 to move the guide holes 128 to a third position at the trailing edge of each window 130, still without axially moving the catheter tube 30. The catheter tube 30 can be rotated, if desired, to achieve a different circumferential orientation. The physician repeats the above-described electrode deployment steps to form a third ring pattern of lesions. The physician withdraws the electrodes 66 into the carriers 122 and withdraws the basket 56, completing the procedure.

Figure 35:
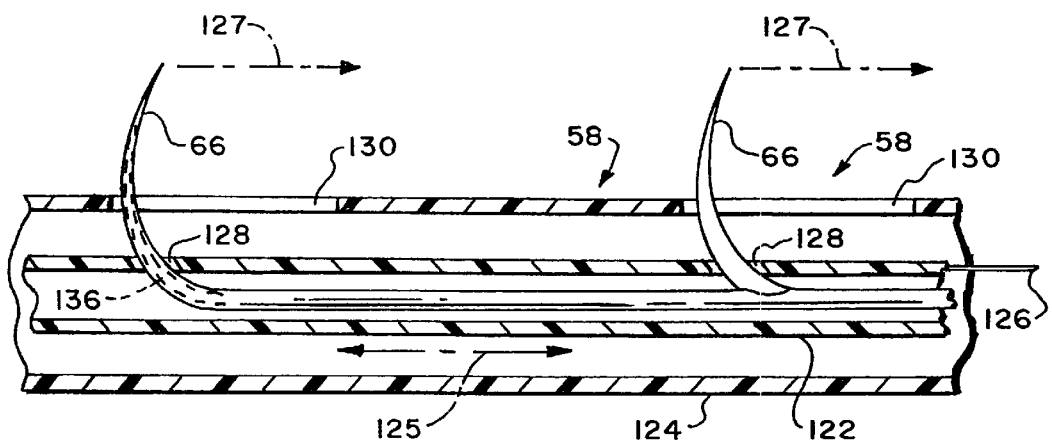
FIG. 35 is a side section view of a stationary spine which comprises a portion of an operative element and which carries a pair of movable electrodes for creating lesion patterns.

As FIG. 35 shows, each carrier 122 can hold more than one electrode 66. In this arrangement, the electrodes 66 on each carrier 122 are extendable and retractable through axially spaced-apart guide holes 128 in the carrier 122. In this arrangement, the outer sleeve 124 includes multiple windows 130 registering with the electrode guide holes 128. In this arrangement, the physician is able to simultaneously create multiple ring patterns. Further, the physician can axially shift the electrodes 66 and create additional ring patterns by shifting the carrier 122, and without axial movement of the catheter tube 30.

Figure 36:
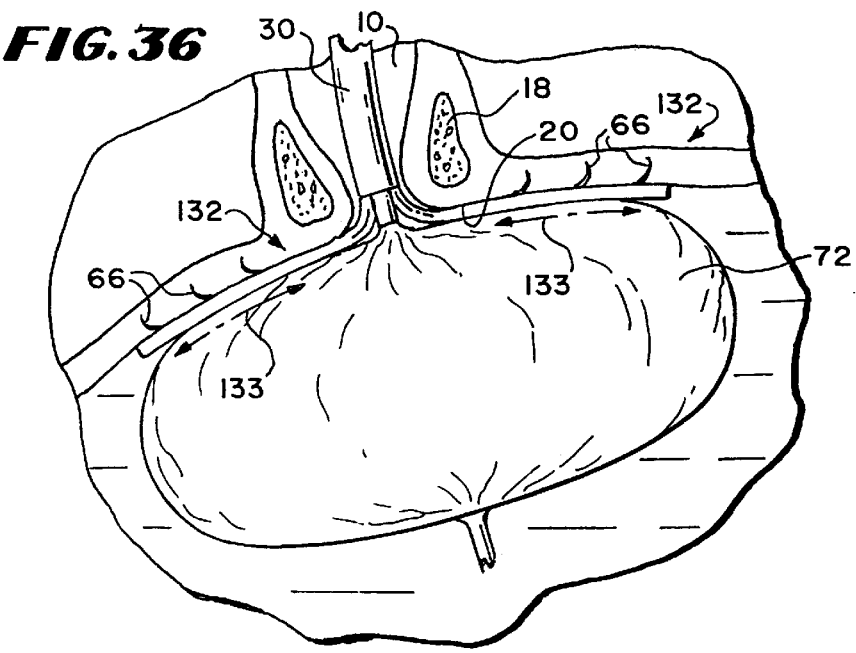
FIGS. 36 and 37 are enlarged side views of operative elements deployed in the cardia and having movable spines for positioning either multiple electrodes or a single electrode in different positions for creating lesion patterns.
Figure 37:
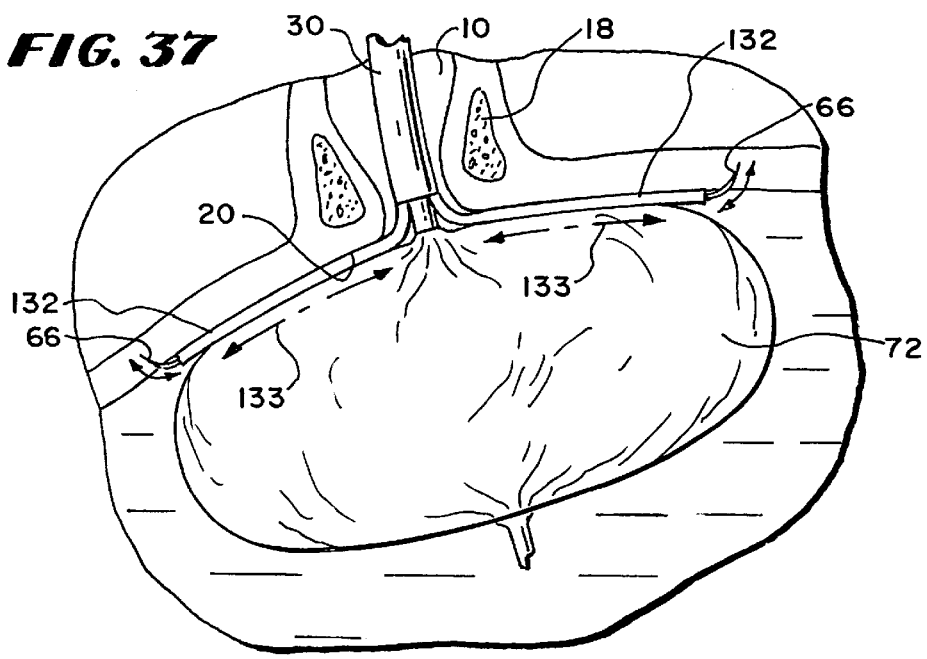

In the foregoing descriptions, each spine 58 comprises a stationary part of the basket 56. As FIGS. 36 and 37 show, an array of movable spines 132, not joined to a common distal hub, can be deployed along the expandable balloon structure 72. In FIGS. 36 and 37, the expandable structure 72 is shown to have a disk-shaped geometry and is deployed in the cardia 20 of the stomach 12. Two movable spines 132 are shown for the purpose of illustration, but it should be appreciated that fewer or greater number of movable spines 132 could be deployed.

In this embodiment, the proximal ends of the spines 132 are coupled, e.g., to a push-pull stylet on the handle (not shown). Under control of the physician, the spines 132 are advanced to a desired position along the structure 72 in the tissue contact region, as shown by arrows 133 in FIGS. 36 and 37. Each movable spine 132 can carry a single electrode 66 (as FIG. 37 shows) or multiple electrodes 66 (as shown in FIG. 36). Regardless, each electrode 66 can be extended and retracted relative to the movable spine 132.

In use, the physician positions the movable spines 132 and deploys the electrode 66 or electrodes to create a first lesion pattern in the contact region. By retracting the electrode 66 or electrodes, the physician can relocate the movable spines 132 to one or more other positions (with or without rotating the catheter tube 30). By deploying the electrode 66 or electrodes in the different positions by moving the spines 132, the physician can form complex lesion patterns in the tissue contact region without axial movement of the catheter tube 30.

Figure 38:
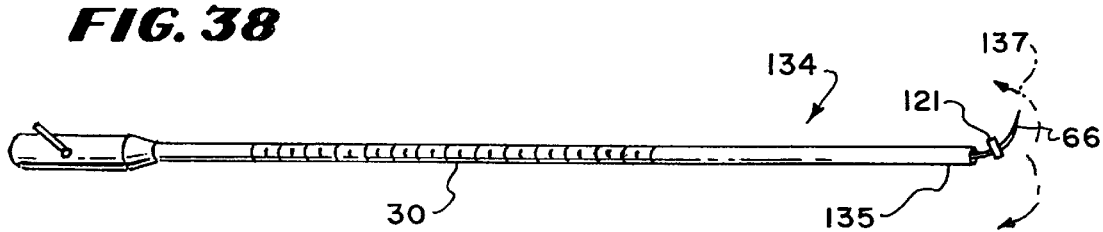
FIG. 38 is an enlarged side view of an operative element that carries a steerable electrode for creating lesions in body sphincters and adjoining tissue.

In yet another alternative embodiment (see FIG. 38), an operative element 134 can comprise a catheter tube 30 that carries at its distal end a single mono-polar electrode 66 (or a bipolar pair of electrodes), absent an associated expandable structure. The distal end of the catheter tube 30 includes a conventional catheter steering mechanism 135 to move the electrode 66 (or electrodes) into penetrating contact with a desired tissue region, as arrows 137 in FIG. 38 show). The electrode 66 can carry a limit collar 121 (as also shown in FIG. 33) to resist advancement of the electrode 66 beyond a desired penetration depth. Using the operative element 134 shown in FIG. 38, the physician forms a desired pattern of lesions by making a succession of individual mono-polar or bipolar lesions.

(iv) Drug Delivery Through Electrodes

A given electrode 66 deployed by an operative device in a sphincter or other body region can also be used to deliver drugs independent of or as an adjunct to lesion formation. In this arrangement, the electrode 66 includes an interior lumen 136 (as FIG. 35 demonstrates for the purpose of illustration).

As before explained, a submucosal lesion can be formed by injecting an ablation chemical through the lumen 136, instead of or in combination with the application of ablation energy by the electrode.

Any electrode 66 possessing the lumen 136 can also be used to deliver drugs to the targeted tissue site. For example, tissue growth factors, fibrosis inducers, fibroblast growth factors, or sclerosants can be injected through the electrode lumen 136, either without or as an adjunct to the application of energy to ablate the tissue. Tissue bulking of a sphincter region can also be achieved by the injection of collagen, dermis, cadaver allograft material, or PTFE pellets through the electrode lumen 136. If desired, radio frequency energy can be applied to the injected bulking material to change its physical characteristics, e.g., to expand or harden the bulking material, to achieve a desired effect.

As another example, the failure of a ring of muscle, e.g., the anal sphincter or the lower esophageal sphincter 18, called achalasia, can also be treated using an electrode 66 having an interior lumen 136, carried by an operative device previously described. In this arrangement, the electrode 66 is deployed and extended into the dysfunctional sphincter muscle. A selected exotoxin, e.g., serotype A of the Botulinum toxin, can be injected through the electrode lumen 136 to produce a flaccid paralysis of the dysfunctional sphincter muscle.

For the treatment of achalasia of a given sphincter, the electrode 66 carried by an operative device can also be conditioned to apply stimulant energy to nerve tissue coupled to the dysfunctional muscle. The stimulant energy provides an observable positive result (e.g., a relaxation of the sphincter) when targeted nerve tissue is in the tissue region occupied by the electrode 66. the observable positive result indicates that position of the electrode 66 should be maintained while applying ablation energy to the nerve tissue. Application of the nerve ablation energy can permanently eliminate the function of a targeted nerve branch, to thereby inactivate a selected sphincter muscle. Further details of the application of ablation energy to nerve tissue can be found in co-pending application entitled "Systems And Methods For Ablating Discrete Motor Nerve Regions."

(v) Surface Electrodes

Figure 39:
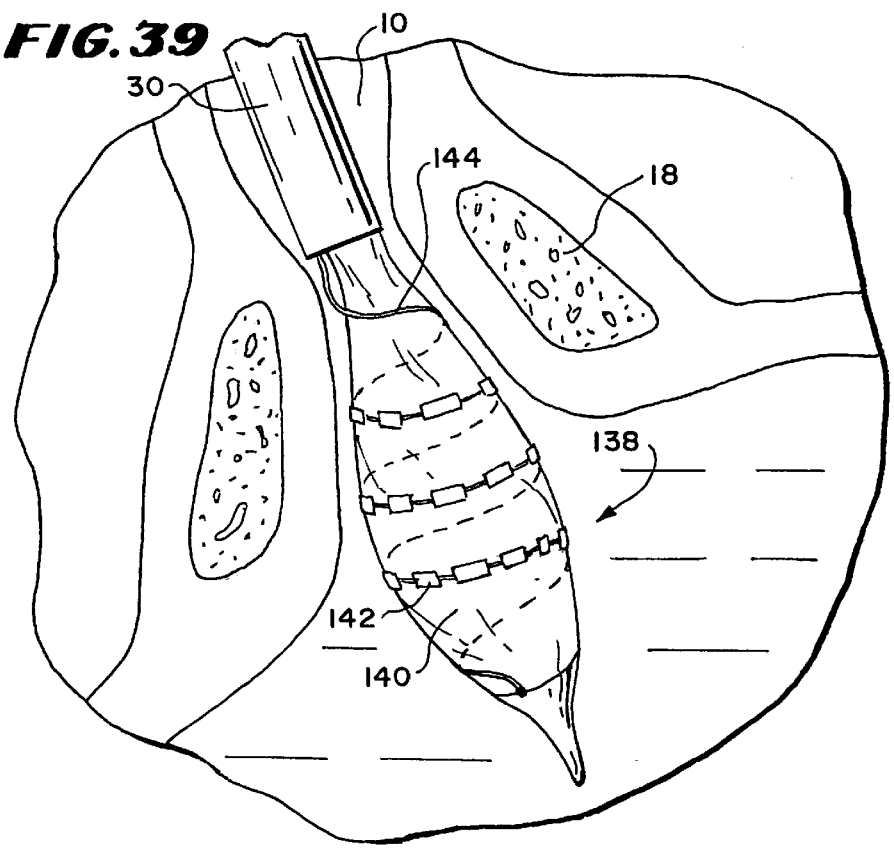
FIG. 39 is an enlarged side view of an operative element carrying surface electrodes for treating abnormal epithelial tissue in the gastrointestinal tract, the operative element being shown in a collapsed condition and deployed in the region of the lower esophageal sphincter.
Figure 40:
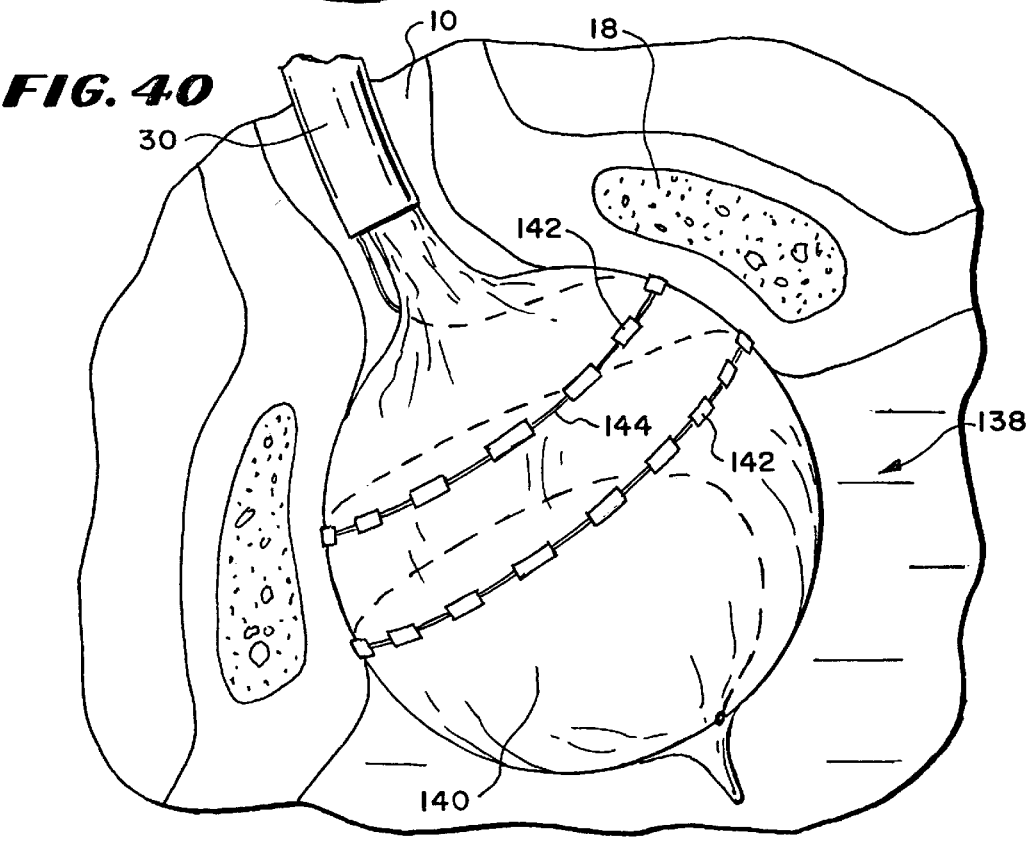
FIG. 40 is an enlarged side view of the operative element shown in FIG. 39 and in an expanded condition contacting the abnormal epithelial tissue for applying ablation energy.

As earlier mentioned, one of the complications of GERD is the replacement of normal esophageal epithelium with abnormal (Barrett's) epithelium. FIGS. 39 and 40 show an operative element 138 for the treatment of this condition.

The operative element 138 includes an expandable balloon structure 140 carried at the distal end of a catheter tube 30. FIG. 39 shows the structure 140 deployed in a collapsed condition in the lower esophageal sphincter 18, where the abnormal epithelium tissue condition forms. FIG. 40 shows the structure 140 in an expanded condition, contacting the abnormal epithelium tissue.

The structure 140 carries an array of surface electrodes 142. In the illustrated embodiment, the surface electrodes 142 are carried by an electrically conductive wire 144, e.g., made from nickel-titanium alloy material. The wire 144 extends from the distal end of the catheter tube 30 and wraps about the structure 140 in a helical pattern. The electrodes 142 are electrically coupled to the wire 144, e.g., by solder or adhesive. Alternatively, the balloon structure 140 can have painted, coated, or otherwise deposited on it solid state circuitry to provide the electrical path and electrodes.

Expansion of the balloon structure 140 places the surface electrodes 142 in contact with the abnormal epithelium. The application of radio frequency energy ohmically heats the tissue surface, causing necrosis of the abnormal epithelium. The desired effect is the ablation of the mucosal surface layer (about 1 mm to 1.5 mm), without substantial ablation of underlying tissue. The structure 140 is then collapsed, and the operative element 138 is removed.

Absent chronic exposure to stomach 12 acid due to continued spontaneous relaxation of the lower esophageal sphincter 18, subsequent healing of the necrosed surface tissue will restore a normal esophageal epithelium.

D. Electrode Structures to Minimize Lesion Overlap

As before described, it is desirable to create one or more symmetric rings of lesions with enough total volume to sufficiently shrink the lower esophageal sphincter or cardia.

Figure 83:
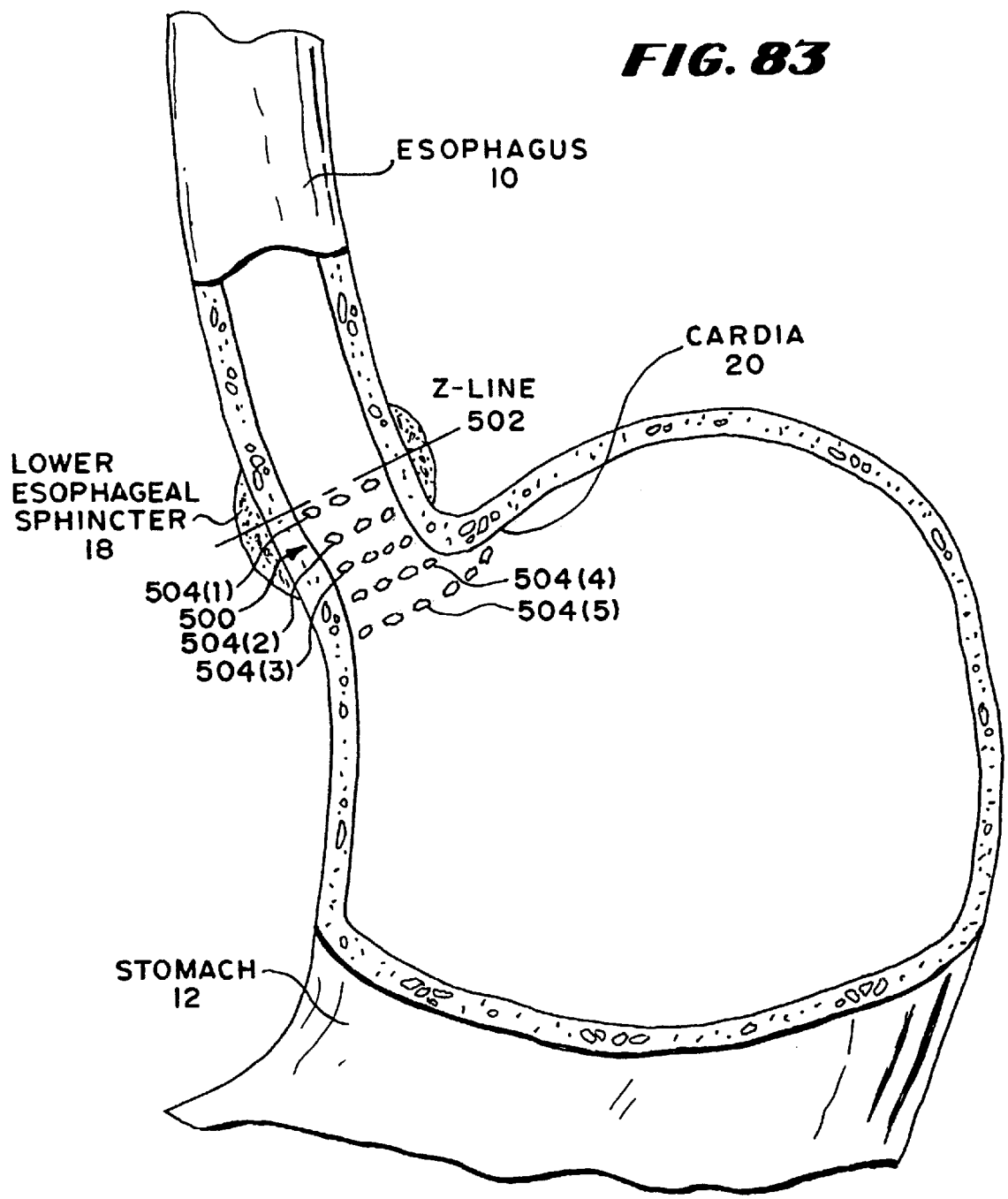
FIG. 83 is an anatomic view of the esophagus and stomach, with portions broken away and in section, showing the location of a composite lesion pattern effective in treating GERD.

FIG. 83 shows a lesion pattern 500 that has demonstrated efficacy in treating GERD. The lesion pattern 500 begins at the Z-line 502, which marks the transition between esophageal tissue (which is generally white in color) and stomach tissue (which is generally pink in color). The tissue color change at or near the Z-line 502 can be readily visualized using an endoscope.

The lower esophageal sphincter 18 (which is about 4 cm to 5 cm in length) extends above and below the Z-line 502. The Z-line 502 marks the high pressure zone of the lower esophageal sphincter 18. In the region of the Z-line 502, the physician may encounter an overlap of sphincter muscle and cardia muscle.

As FIG. 83 shows, the lesion pattern 500 extends about 2 cm to 3 cm from the Z-line 502 into the cardia 20. The pattern 500 comprises a high density of lesion rings 504, spaced apart by about 5 mm, with from four to sixteen lesions in each ring 504. Five rings 504(1) to 504 (5) are shown in FIG. 83. The uppermost ring 504(1) (at or near the Z-line 502) contains eight lesions. The next three rings 504(2) to 504 (4) each contains twelve lesions. The lower most ring 504(5) contains eight lesions.

The lesion pattern 500 formed in this transition region below the Z-line 502 creates, upon healing, an overall desired tightening of the sphincter 18 and adjoining cardia 20 muscle, restoring a normal closure function.

It is also believed that the pattern 500 formed in this transition region may also create a neurophysiologic effect, as well. The lesion pattern 500 may interrupt infra- and supra-sphincter nerve conduction. The nerve pathway block formed by the lesion pattern 500 may mediate pain due to high pH conditions that accompany GERD and may in other ways contribute to the overall reduction of spontaneous sphincter relaxation that the procedure provides.

As before described, rotation or sequential movement of electrodes 66 can achieve the desired complex lesion pattern 500. However, in sequentially placing the lesions, overlapping lesions can occur.

There are various ways to minimize the incidence of lesion overlap.

(i) Full Ring Electrode Structures

To prevent overlapping lesions, the operative element 36 can, e.g., carry a number of electrodes 66 sufficient to form all the desired lesions in a given circumferential ring with a single deployment. For example, as FIG. 53 illustrates, when the desired number of lesions for a given ring is eight, the operative element 36 carries eight electrodes 66. In this arrangement, the electrodes 66 are equally spaced about the circumference of the balloon structure 72 on eight spines 58. As before described, each spine 58 preferably includes an interior lumen with a port 98 to convey a cooling liquid like sterile water into contact with the mucosal surface of the the targeted tissue site.

The generator 38 can include eight channels to supply treatment energy simultaneously to the eight electrodes 66. However, the generator 38 that supplies treatment energy simultaneously in four channels to four electrodes 66 shown, e.g., in FIG. 22, can be readily configured by the controller 52 to supply treatment energy to the eight electrodes 66 shown in FIG. 53.

(1) Monopolar/Hottest Temperature Control

In one configuration, pairs of electrodes 66 are shorted together, so that each channel simultaneously powers two electrodes in a monopolar mode. For simplicity, the shorted electrodes 66 are preferably located on adjacent spines 58, but an adjacent relationship for shorted electrodes is not essential.

Each electrode 66 carries a temperature sensor 80, coupled to the I/O device 54 of the controller 52, as previously described. The controller 52 alternatively samples the temperature sensed by the sensors 80 for each shorted pair of electrodes 66. The controller 52 selects the hottest sensed temperature to serve as the input to control the magnitude of power to both electrodes. Both electrodes receive the same magnitude of power, as they are shorted together.

(2) Monopolar/Average Temperature Control

In one configuration, pairs of electrodes 66 are shorted together, as described in the previous configuration, so that each channel simultaneously powers two electrodes in a monopolar mode.

Each electrode 66 carries a temperature sensor 80 and are coupled to the I/O device 54 of the controller 52. In this configuration, the temperature sensors 80 for each shorted pair of electrodes 66 are connected in parallel. The controller 52 thus receives as input a temperature that is approximately the average of the temperatures sensed by the sensors 80 for each shorted pair of electrodes 66. The controller 52 can include an algorithm to process the input to achieve a weighted average. The controller 52 uses this approximate average to control the magnitude of power to both electrodes. As previously stated, both electrodes receive the same magnitude of power, as they are shorted together.

(3) Monopolar/Switched Control

In this configuration, the controller 52 includes a switch element, which is coupled to each electrode 66 and its associated temperature sensor 80 independently. In one position, the switch element couples the four channels of the generator 38 to four of the electrodes (Electrode Group A). In another position, the switch element couples the four channels of the generator 38 to another four of the electrodes (Electrode Group B).

The electrodes of Group A could be located on one side of the element 36, and the electrodes of Group B could be located on the opposite side of the element 36. Alternatively, the electrodes 66 of Groups A and B can be intermingled about the element 36.

The switch element can switch between Electrode Group A and Electrode Group B, either manually or automatically. The switching can occur sequentially or in a rapidly interspersed fashion.

In a sequential mode, Electrode Group A is selected, and the controller samples the temperatures sensed by each sensor 80 and individually controls power to the associated electrode 66 based upon the sensed temperature. As tissue heating effects occur as a result of the application of energy by Electrode Group A, the other Electrode Group B is selected. The controller samples the temperatures sensed by each sensor 80 and individually controls power to the associated electrode 66 based upon the sensed temperature. As tissue heating effects occur as a result of the application of energy by Electrode Group B, the other Electrode Group A is selected, and so on. This mode may minimize overheating effects for a given electrode group.

In an interspersed fashion, the switching between Electrode Groups A and B occurs at greater time intervals between the application of energy, allowing tissue moisture to return to dessicated tissue between applications of energy.

(4) Bipolar Control

In this configuration, the controller 52 conditions four electrodes 66 to be transmitters (i.e., coupled to the four channels of the generator 38) and conditions the other four electrodes to be returns (i.e., coupled to the energy return of the generator 38). For simplicity, the transmitter and return electrodes are preferably located on adjacent spines 58, but this is not essential.

In one arrangement, the four returns can be independent, with no common ground, so that each channel is a true, independent bipolar circuit. In another arrangement, the four returns are shorted to provide a single, common return.

For each bipolar channel, the controller 52 samples temperatures sensed by the sensors 80 carried by each electrode 66. The controller 52 can average the sensed temperature conditions by each electrode pair. The controller 52 can include an algorithm to process the input to achieve a weighted average. Alternatively, the controller 52 can select the maximum temperature condition sensed by each electrode pair for control purposes.

The electrodes 66 used as return electrodes can be larger than the electrodes 66 used to transmit the energy. In this arrangement, the return electrodes need not carry temperature sensors, as the hottest temperature will occur at the smaller energy transmitting electrode.

(ii) Partial Ring Electrode Structures

To prevent overlapping lesions, the operative element 36 can, e.g., carry a number of electrodes 66 sufficient to form, in a single deployment, a partial arcuate segment of the full circumferential ring. For example, as FIG. 54 illustrates, when the desired number of lesions for a given ring is eight, the operative element 36 carries four electrodes 66 in a closely spaced pattern spanning 135 degrees on four spines 58.

In use, the physician deploys the element 36 and creates four lesions in a partial arcuate segment comprising half of the full circumferential ring. The physician then rotates the element 36 one-hundred and eighty degrees and creates four lesions in a partial arcuate segment that comprises the other half of the full circumferential ring.

The physician may find that there is less chance of overlapping lesions by sequentially placing four lesions at 180 intervals, than placing four lesions at 90 degree intervals, as previously described.

E. Mechanically Expandable Electrode Structures

FIGS. 41 and 42 show an operative element 146 suited for deployment in the lower esophageal sphincter 18, cardia 20, and other areas of the body.

In this embodiment, the operative element 146 comprises an expandable, three-dimensional, mechanical basket 148. As illustrated, the basket 148 includes eight jointed spines 150, although the number of spines 158 can, of course, vary. The jointed spines 150 are pivotally carried between a distal hub 152 and a proximal base 154.

Each jointed spine 150 comprises a body made from inert wire or plastic material. Elastic memory material such as nickel titanium (commercially available as NITINOL™ material) can be used, as can resilient injection molded plastic or stainless steel. In the illustrated embodiment, the jointed spines 150 possess a rectilinear cross sectional shape. However, the cross sectional shape of the spines 150 can vary.

Each jointed spine 150 includes a distal portion 158 and a proximal portion 160 joined by a flexible joint 156. The distal and proximal portions 158 and 160 flex about the joint 156. In the illustrated embodiment, the spine portions 158 and 160 and joint 156 are integrally formed by molding. In this arrangement, the joint 156 comprises a living hinge. Of course, the spine portions 158 and 160 can be separately manufactured and joined by a mechanical hinge.

In the illustrated embodiment, a pull wire 162 is attached to the distal hub 152 of the basket 148. Pulling on the wire 162 (e.g., by means of a suitable push-pull control on a handle at the proximal end of the catheter tube 30) draws the hub 152 toward the base 154. Alternatively, a push wire joined to the base 154 can advance the base 154 toward the hub 152. In either case, movement of the base 154 and hub 152 toward each other causes the spines 150 to flex outward about the joints 156 (as FIG. 42 shows). The basket 148 opens, and its maximum diameter expands.

Conversely, movement of the base 154 and hub 152 away from each other causes the spines 150 to flex inward about the joints 156. The basket 148 closes (as FIG. 41 shows), and its maximum diameter decreases until it assumes a fully collapsed condition.

Each joint 156 carries an electrode 166. The electrode 166 can comprise an integrally molded part of the spine 150, or it can comprise a separate component that is attached, e.g. by solder or adhesive, to the spine 150. The electrode material can also be deposited or coated upon the spine 150.

Figure 43:
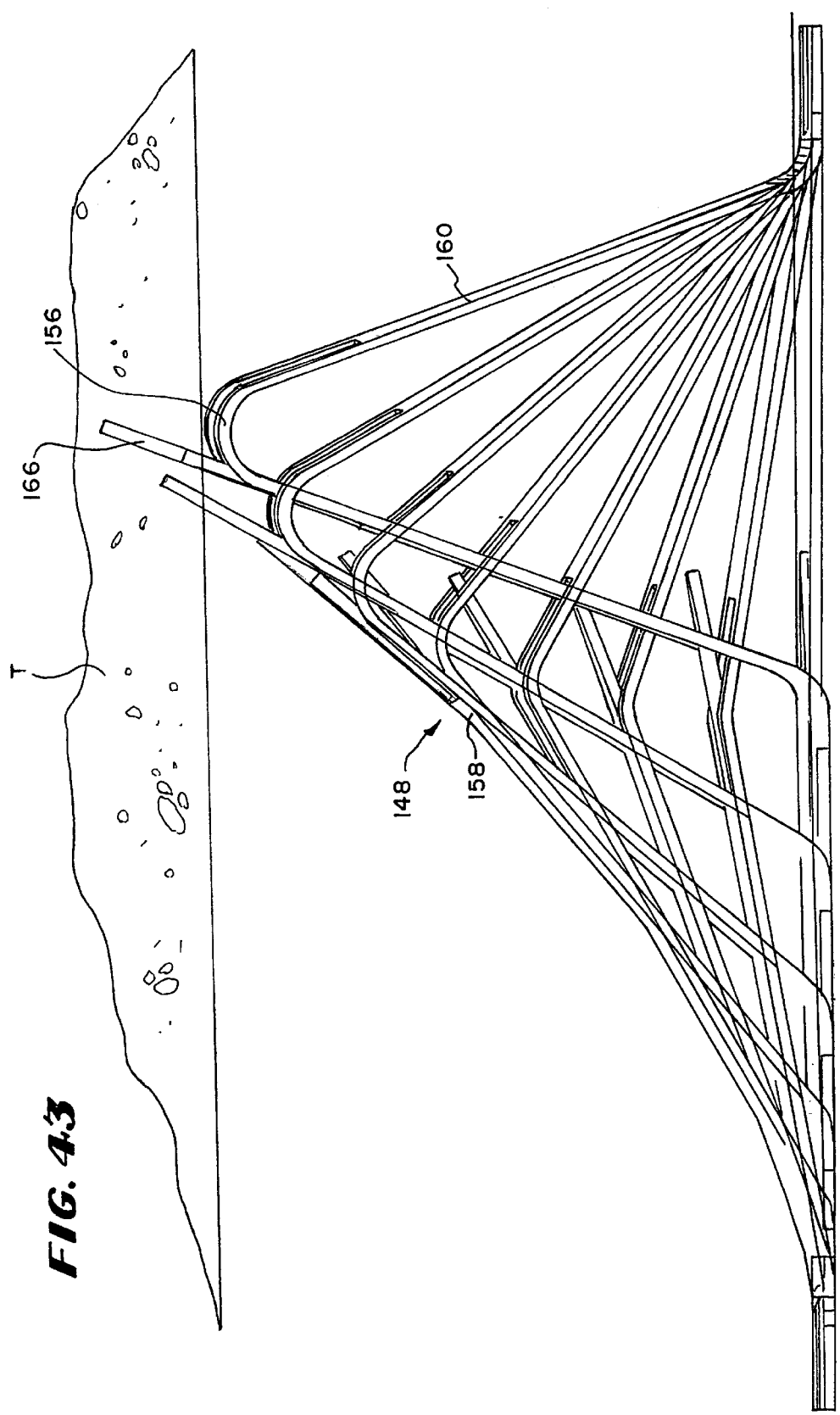
FIG. 43 is a side view showing a spine of the basket shown in FIG. 41 as it is mechanically flexed for penetrating tissue.
Figure 46:
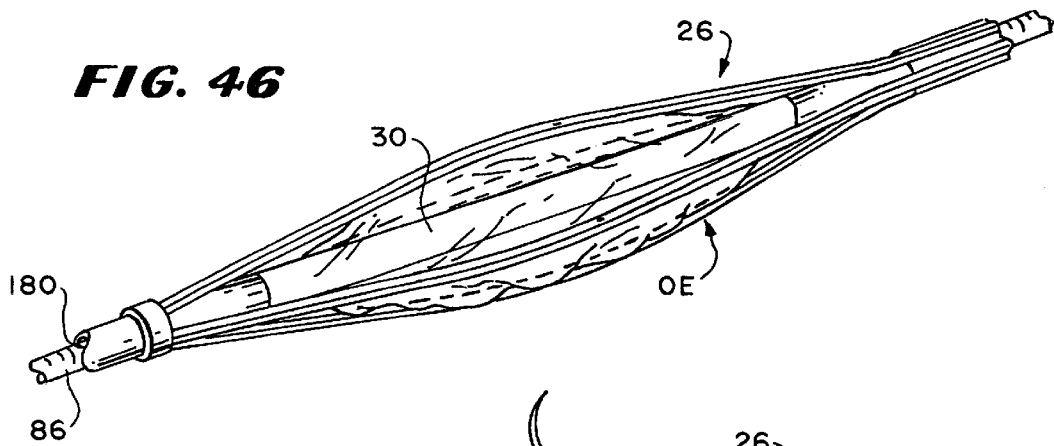
FIG. 46 is a perspective view of an operative element that is deployed for use over a flexible endoscope, shown in a collapsed condition.

When the basket 148 is closed, the electrodes 166 nest within the joints 156 in a lay flat condition (as FIG. 41 shows), essentially coplanar with the distal and proximal portions 158 and 160 of the spines 150. As best shown in FIG. 43, as the basket 148 opens, flexure of the spines 150 about the joints 156 progressively swings the electrodes 166 outward into a position for penetrating tissue (designated T in FIG. 43).

As FIG. 43 shows, flexure of a given spine 150 about the associated joint 156 swings the electrode 166 in a path, in which the angle of orientation of the electrode 166 relative to the spine progressively increases. As the basket 148 opens, the electrode 166 and the distal portion 158 of the spine 150 become generally aligned in the same plane.

Further expansion increases the radial distance between the basket axis 164 and distal tip of the electrode 166 (thereby causing tissue penetration), without significantly increasing the swing angle between the basket axis 164 and the electrode 166 (thereby preventing tissue tear). During the final stages of basket expansion, the electrode 166 moves in virtually a linear path into tissue. It is thus possible to deploy the electrode in tissue simultaneously with opening the basket 148.

FIGS. 44 and 45 show an operative element 168 comprising a spring biased basket 170. In the illustrated embodiment, the distal end of the catheter tube 30 carries two electrodes 172. A single electrode, or more than two electrodes, can be carried in the same fashion on the distal end of the catheter tube 30.

The electrodes 172 are formed from a suitable energy transmitting materials, e.g stainless steel. The electrodes 172 have sufficient distal sharpness and strength to penetrate a desired depth into the smooth muscle of the esophageal or cardia 20 wall.

The proximal end of each electrode 172 is coupled to the leaf spring 174. The leaf spring 174 normally biases the electrodes 172 in an outwardly flexed condition facing the proximal end of the catheter tube 30 (as FIG. 44 shows).

An electrode cover 176 is slidably mounted on the distal end of the catheter tube 30. A stylet 178 is coupled to the electrode cover 176. The stylet 178 is movable axially along the catheter tube 30, e.g., by a lever on the handle at the proximal end of the catheter tube 30.

Pulling on the stylet 178 moves the electrode cover 176 over the electrodes 172 into the position shown in FIG. 45. On this position, the cover 176 encloses the electrodes 172, pulling them inward against the distal end of the catheter tube 30. Enclosed within the cover 176, the electrodes 172 are maintained in a low profile condition for passage through the esophagus, e.g., through Lower esophageal sphincter 18 and into a position slightly beyond the surface of the cardia 20.

Pushing on the stylet 178 moves the electrode cover 176 toward a distal-most position beyond the electrodes 172, as shown in FIG. 44. Progressively unconstrained by the cover 176, the electrodes 172 spring outward. The outward spring distance of electrodes 172 depends upon the position of the cover 176. The electrodes 172 reach their maximum spring distance when the cover 176 reaches its distal-most position, as FIG. 44 shows. The distal ends of the electrodes 172 are oriented proximally, to point, e.,g. toward the cardia 20.

With the electrodes 172 sprung outward, the physician pulls rearward on the catheter tube 30. The electrodes 172 penetrate the cardia 20. The electrodes apply energy, forming subsurface lesions in the cardia 20 in the same fashion earlier described. As FIG. 44 shows, the proximal region of each electrode 172 is preferably enclosed by an electrical insulating material 70, to prevent ohmic heated of the mucosal surface of the cardia 20.

Upon formation of the lesions, the physician can move the catheter tube 30 forward, to advance the electrodes 172 out of contact with the cardia 20. By rotating the catheter tube 30, the physician can reorient the electrodes 172. The physician can also adjust the position of the cover 176 to increase or decrease the diameter of the outwardly flexed electrodes 172. Pulling rearward on the catheter tube 30 causes the electrodes to penetrate the cardia 20 in their reoriented and/or resized position. In this way, the physician can form desired ring or rings of lesion patterns, as already described.

Upon forming the desired lesion pattern, the physician advances the electrodes 172 out of contact with the cardia 20. The physician moves the cover 176 back over the electrodes 172 (as FIG. 45 shows). In this condition, the physician can withdraw the catheter tube 30 and operative element 168 from the cardia 20 and esophagus 10, completing the procedure.

F. Extruded Electrode Support Structures

Figure 63:
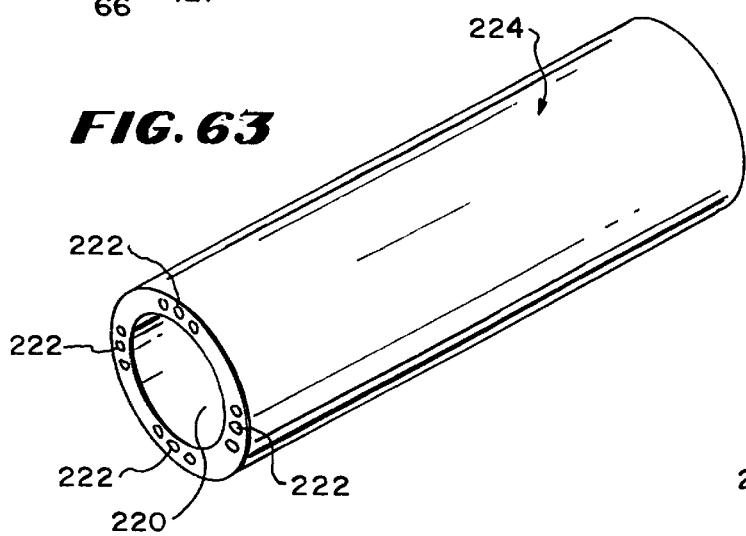
FIG. 63 is a perspective view of an extruded tube that, upon further processing, will form an expandable basket structure.
Figure 64:
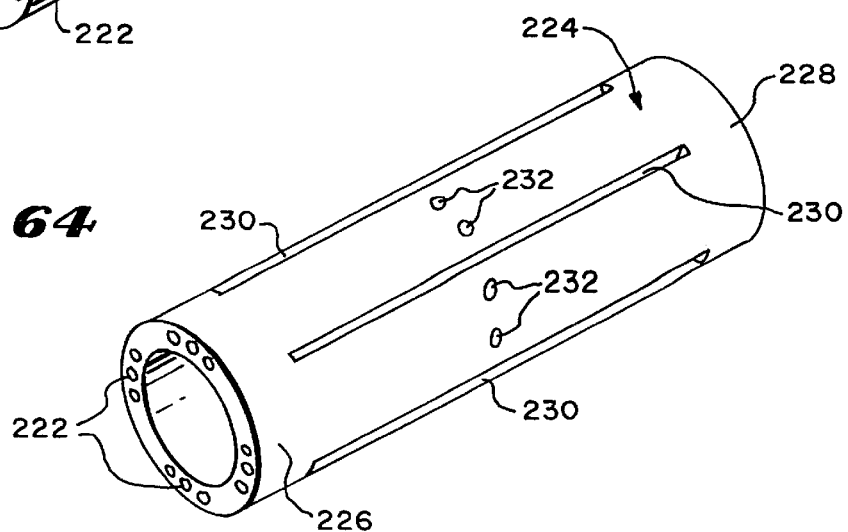
FIG. 64 is a perspective view of the extruded tube shown in FIG. 62 with slits formed to create an expandable basket structure.
Figure 65:
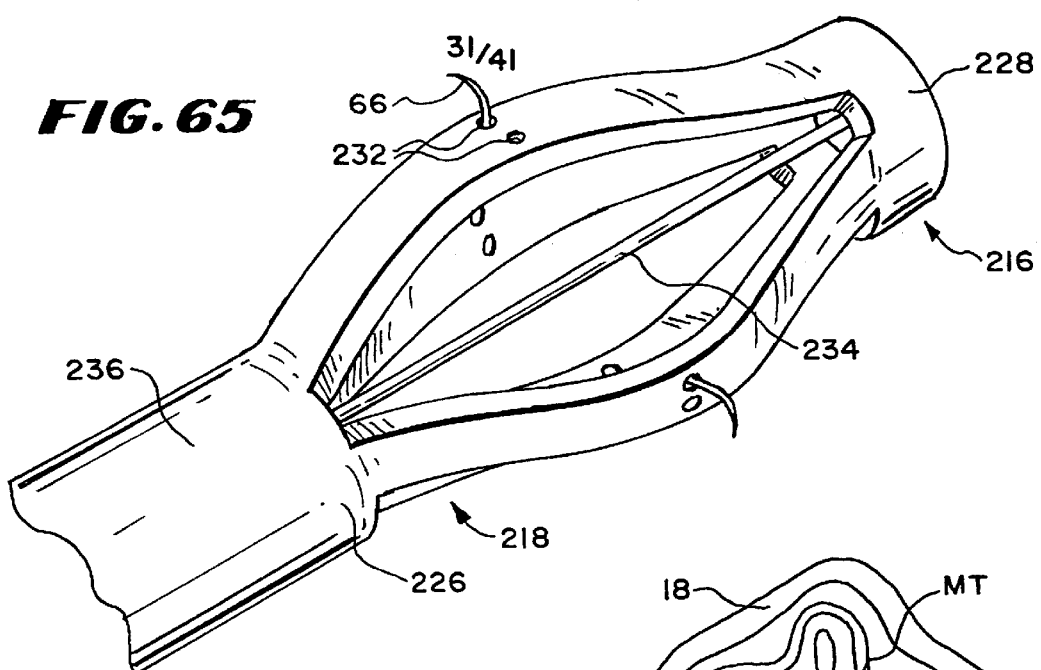
FIG. 65 is the expandable basket structure formed after slitting the tube shown in FIG. 63.

FIGS. 63 to 65 show another embodiment of an operative element 216 suited for deployment in the lower esophageal sphincter 18, cardia 20, and other areas of the body. In this embodiment, the operative element 216 comprises an expandable, extruded basket structure 218 (as FIG. 65 shows).

The structure 218 is first extruded (see FIG. 63) as a tube 224 with a co-extruded central interior lumen 220. The tube 224 also includes circumferentially spaced arrays 222 of co-extruded interior wall lumens. Each array 222 is intended to accommodate an electrode 66 and the fluid passages associated with the electrode 66.

In each array 222, one wall lumen accommodates passage of an electrode 66 and related wires. Another lumen in the array 222 is capable of passing fluids used, e.g. to cool the mucosal surface. Another lumen in the array 222 is capable of passing fluids aspirated from the targeted tissue region, if required.

Once extruded (see FIG. 64), the tube wall is cut to form slits 230 between the lumen arrays 222. Proximal and distal ends of the tube are left without slits 230, forming a proximal base 226 and a distal hub 228. Appropriate ports 232 are cut in the tube wall between the slits 230 to accommodate passage of the electrodes 66 and fluids through the wall lumens. The base 226 is coupled to the distal end of a catheter tube 236.

In the illustrated embodiment (see FIG. 65), a pull wire 234 passing through the interior lumen 220 is attached to the distal hub 228. Pulling on the wire 234 (e.g., by means of a suitable push-pull control on a handle at the proximal end of the catheter tube 236) draws the hub 228 toward the base 226 (as FIG. 65 shows). Alternatively, a push wire joined to the base 226 can advance the base 226 toward the hub 228.

In either case, movement of the base 226 and hub 228 toward each other causes the tube 224 to flex outward between the slits 230, forming, in effect, a spined basket. The extruded basket structure 218 opens, and its maximum diameter expands.

Conversely, movement of the base 226 and hub 228 apart causes the tube 224 to flex inward between the slits 230. The extruded basket structure 218 closes and assumes a collapsed condition.

The central co-extruded lumen 220 is sized to accommodate passage of a guide wire or an endoscope, as will be described in greater detail later.

G. Cooling and Aspiration

As previously described with respect to the operative element 36 shown, e.g., in FIGS. 5, 7, and 11, it is desirable to cool the mucosal surface while applying energy to ohmically heat muscle beneath the surface. To accomplish this objective, the operative element 36 includes a means for applying a cooling liquid like sterile water to mucosal tissue at the targeted tissue region and for aspirating or removing the cooling liquid from the targeted tissue region.

Various constructions are possible.

(i) Aspiration Through the Spines

Figure 55:
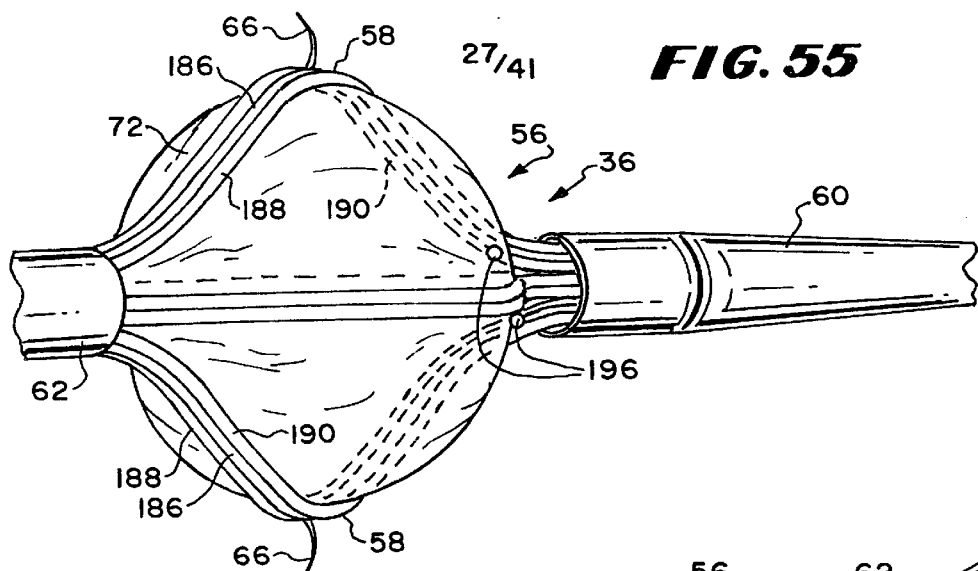
FIG. 55 a perspective distal facing view of an operative element for treating body sphincters and adjoining tissue regions, shown a spine structure with cooling and aspiration ports located in the spines.
Figure 56:
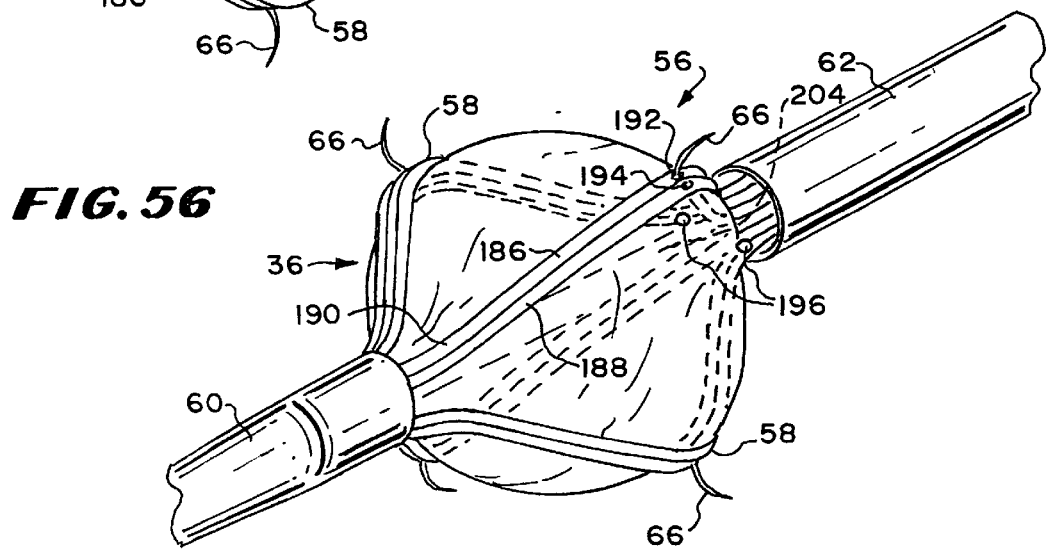
FIG. 56 a perspective proximal facing view of an operative element shown in FIG. 56.

In the embodiment shown in FIGS. 55 and 56, the spines 58 extend between distal and proximal ends 60 and 62 of the element 36, forming a basket 56. Four spines 58 are shown for purpose of illustration. An expandable balloon structure 72 is located within the basket 56, as already described. An inflation tube 204 (see FIG. 56) conveys a media to expand the structure 72 during use.

As FIGS. 55 and 56 show, each spine 58 comprises three tubes 186, 188, and 190. Each tube 186, 188, and 190 has an interior lumen.

The first tube 186 includes an electrode exit port 192 (see FIG. 56). The electrode 66 passes through the exit port 192 for deployment in the manner previously described.

The second tube 188 includes a cooling port 194. The cooling liquid passes through the cooling port 194 into contact with mucosal tissue. The cooling port 194 is preferably situated on the outside (i.e., tissue facing) surface of the spine 58, adjacent the electrode exit port 192 (see FIG. 56).

The third tube 190 includes an aspiration port 196. Cooling liquid is aspirated through the port 196. The port 196 is preferably situated on the inside (i.e. facing away from the tissue) surface of the spine 58.

Preferable, at least one of the aspiration ports 196 is located near the distal end 60 of the element 36, and at least one the aspiration ports 196 is located near the proximal end 62 of the element 36. In the illustrated embodiment, two aspiration ports are located near the distal end 60, on opposite spines 58 (see FIG. 55). Likewise, two aspiration ports are located near the proximal end 62, on opposite spines 58 (see FIG. 56). This arrangement provides for efficient removal of liquid from the tissue region.

The electrodes 66 are commonly coupled to the control lever 198 on the handle 28 (see FIG. 57), to which the catheter tube 30 carrying the element 36 is connected. The lumen of the second tube 188 communicates with a port 200 on the handle 28. In use, the port 200 is coupled to a source of cooling fluid. The lumen of the third tube 190 communicates with a port 202 on the handle 28. In use, the port 202 is coupled to a vacuum source. The inflation tube 204 communicates with a port 206 on the handle 28. The port 206 connects to a source of inflation media, e.g., air in a syringe.

(ii) Interior Aspiration Through An Inner Member

Figure 58A:
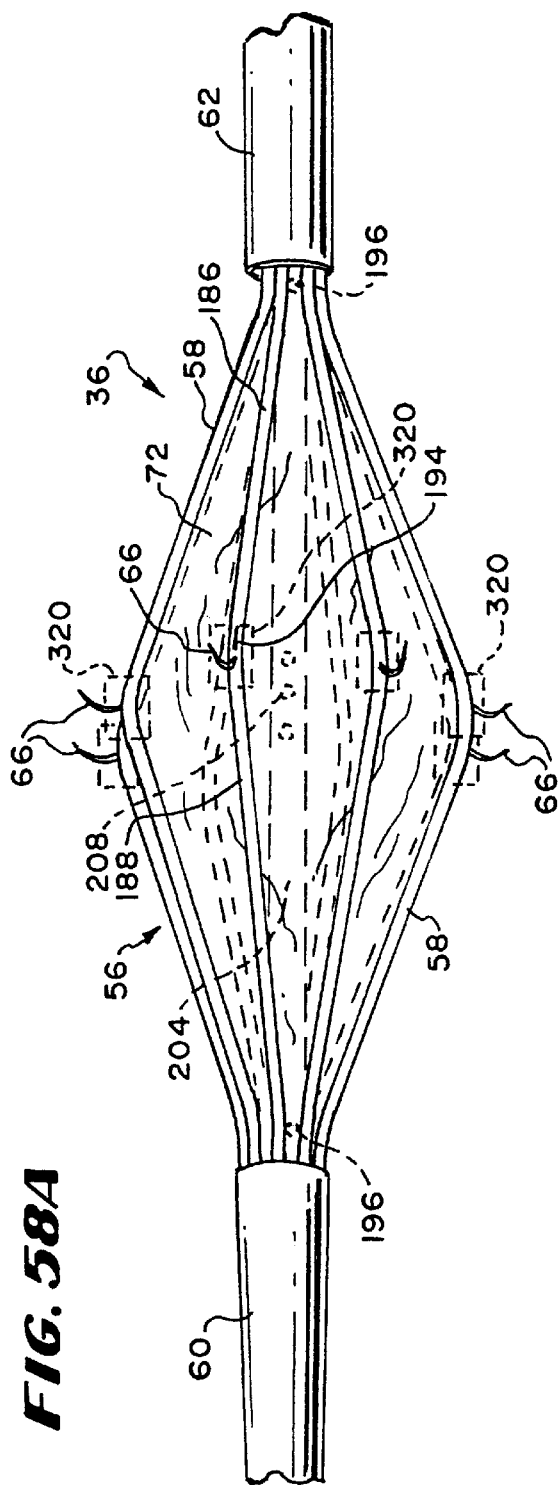
FIG. 58A a perspective view of an operative element for treating body sphincters and adjoining tissue regions, shown a spine structure with cooling ports located in the spines and aspiration ports located in an interior lumen.

In the alternative embodiment shown in FIG. 58A, the spines 58 (eight are shown for purpose of illustration) each comprises at least two tubes 186 and 188. In FIG. 58A, the inflation tube 204 extends through the expandable balloon structure 72, between the distal and proximal ends 60 and 62 of the element 36. Inflation ports 208 communicate with a lumen within the tube 204 to convey the expansion media into the structure 72.

The first tube 186 includes the electrode exit port 192, through which the electrode 66 passes. The second tube 188 includes the outside facing cooling port 194, for passing cooling liquid into contact with mucosal tissue.

At least one aspiration port 196 communicates with a second lumen in the inflation tube 204. In the illustrated embodiment, two aspiration ports 196 are provided, one near the distal end 60 of the element 36, and the other near the proximal end 62 of the element 36.

Figure 57:
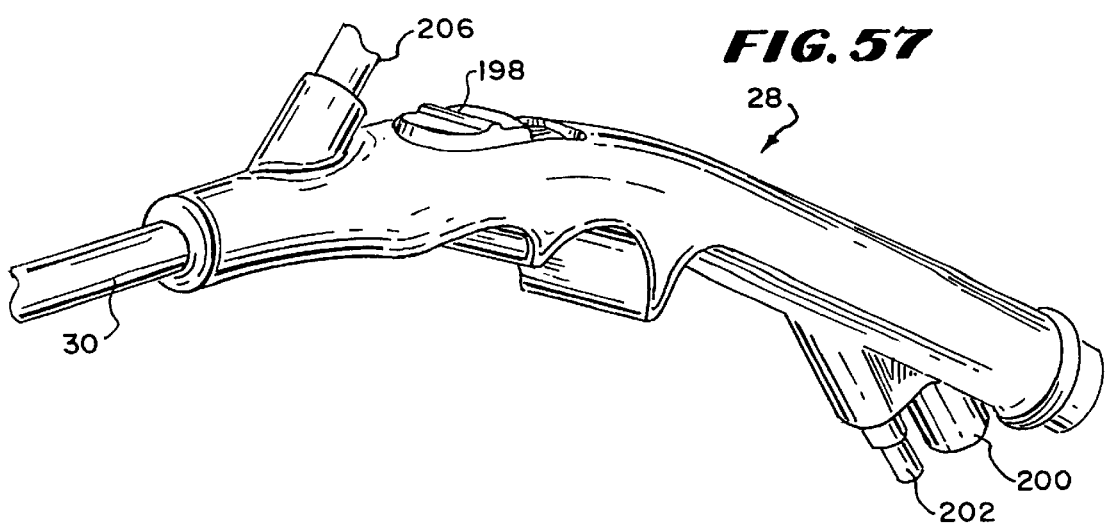
FIG. 57 is a perspective view of a handle for manipulating the operative element shown in FIGS. 55 and 56.

The element 36 shown in FIG. 58A can be coupled to the handle 28 shown in the FIG. 57 to establish communication between the tubes 188 and 204 in the manner already described.

In an alternative embodiment (shown in phantom lines in FIG. 58A), a sponge-like, liquid retaining material 320 can be applied about each spine 58 over the electrode exit port 192 the cooling port 194. The electrode 66 passes through the spongy material 320. Cooling liquid passing through the cooling port 194 is absorbed and retained by the spongy material 320. The spongy material 320 keeps the cooling liquid in contact with mucosal tissue at a localized position surrounding the electrode 66. By absorbing and retaining the flow of cooling liquid, the spongy material 320 also minimizes the aspiration requirements. The presence of the spongy material 320 to absorb and retain cooling liquid also reduces the flow rate and volume of cooling liquid required to cool mucosal tissue, and could eliminate the need for aspiration altogether.

Figure 58B:
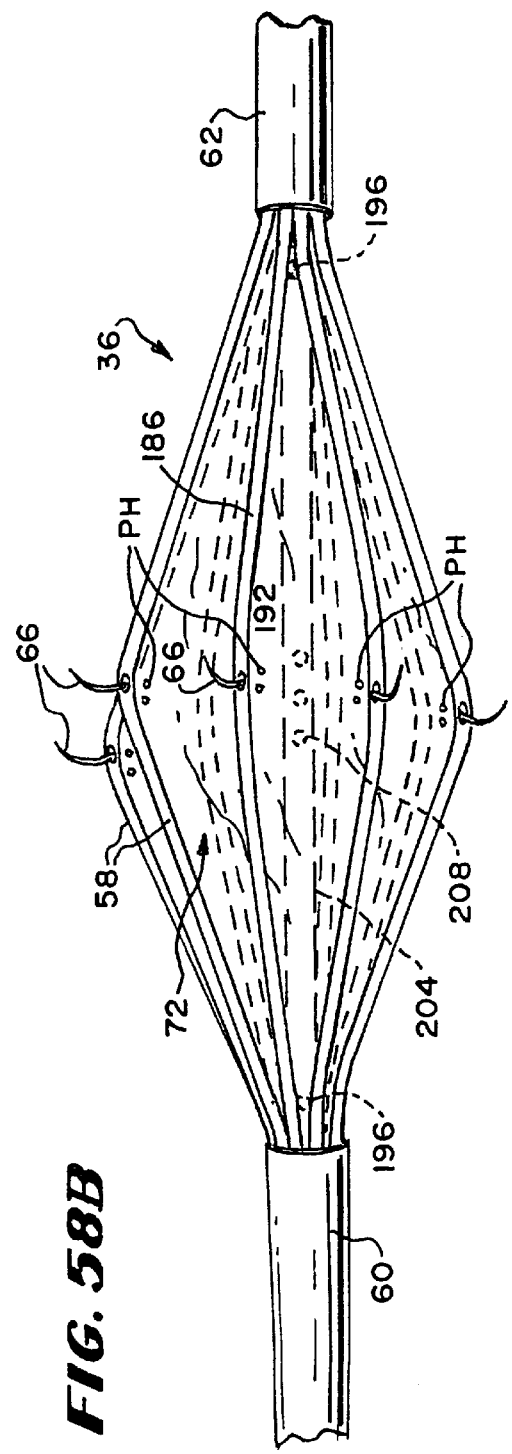
FIG. 58B a perspective view of an operative element for treating body sphincters and adjoining tissue regions, shown a spine structure with an underlying expandable balloon structure having pin hole ports which weep cooling liquid about the electrodes.

In another alternative embodiment, as shown in FIG. 58B, the spines 58 (eight are shown for purpose of illustration) each comprises a single tube 186, which includes the electrode exit port 192, through which includes the electrode exit port 192, through which the electrode 66 passes. As in FIG. 58A, the inflation tube 204 in FIG. 58B extends through the expandable balloon structure 72. Inflation ports 208 communicate with a lumen within the tube 204 to convey the expansion media into the structure 72.

In this embodiment, the expansion medium comprises the cooling liquid. A pump conveys the cooling liquid into the structure 72. Filling the structure 72, the cooling liquid causes expansion. The structure 72 further includes one or more small pin holes PH near each electrode 66. The cooling liquid "weeps" through the pin holes PH, as the pump continuously conveys cooling liquid into the structure 72. The cooling liquid contacts and cools tissue in the manner previously described.

As in FIG. 58A, at least one aspiration port 196 communicates with a second lumen in the inflation tube 204 to convey the cooling liquid from the treatment site. In FIG. 58B, two aspiration ports 196 are provided, one near the distal end 60 of the element 36, and the other near the proximal end 62 of the element 36.

(iii) Tip Aspiration/Guide Wire

In the alternative embodiment shown in FIG. 59, the spines 58 (four are shown for purpose of illustration) each comprises at least two tubes 186 and 188. Like the embodiment shown in FIG. 58, the inflation tube 204 in FIG. 59 extends through the expandable balloon structure 72, between the distal and proximal ends 60 and 62 of the element 36. Inflation ports 208 communicate with a lumen within the tube 204 to convey the expansion media into the structure 72.

The first tube 186 includes the electrode exit port 192, through which the electrode 66 passes. The second tube 188 includes the outside facing cooling port 194, for passing cooling liquid into contact with mucosal tissue.

In the embodiment shown in FIG. 59, the distal end 60 of the element 36 includes an aspiration port 196, which communicates with a second lumen in the inflation tube 204.

The element 36 shown in FIG. 58 can be coupled to the handle 28 shown in the FIG. 57 to establish communication between the tubes 188 and 204 in the manner already described.

Figure 61:
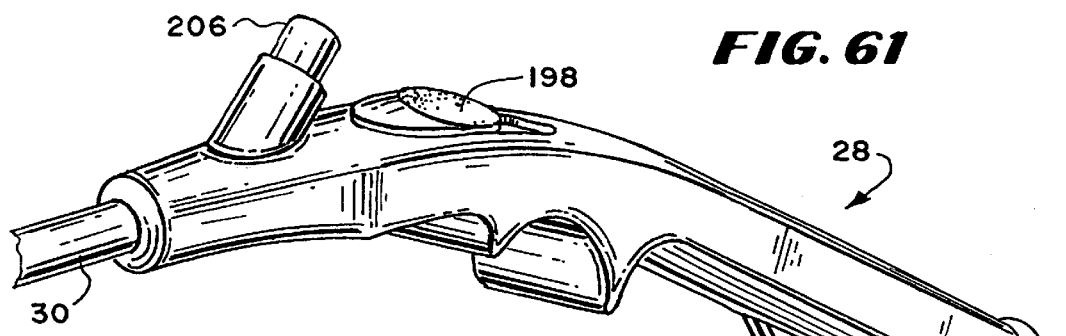
FIG. 61 is a perspective view of a handle for manipulating the operative element over the guide wire, as shown in FIG. 60.

In the embodiment shown in FIG. 59, the lumen in the inflation tube 204 used for aspiration can be alternatively used to pass a guide wire 210, as FIG. 60 shows. The guide wire 210 is introduced through the aspiration port 202 on the handle 28 (as FIG. 61 shows).

Use of a guide wire 210 can obviate the need for the introducer 32 previously described and shown in FIG. 9, which may in certain individuals cause discomfort. In use, the physician passes the small diameter guide wire 210 through the patient's mouth and pharynx, and into the esophagus 10 to the targeted site of the lower esophageal sphincter or cardia. The physician can next pass the operative element 36 (see FIG. 60) over the guide wire 210 into position. The physician can also deploy an endoscope next to the guide wire 210 for viewing the targeted site and operative element 36.

Use of the guide wire 210 also makes possible quick exchanges of endoscope and operative element 36 over the same guide wire 210. In this arrangement, the guide wire 210 can serve to guide the endoscope and operative element 36 to the targeted site in quick succession.

G. Vacuum-Assisted Stabilization of Mucosal Tissue

Figure 66:
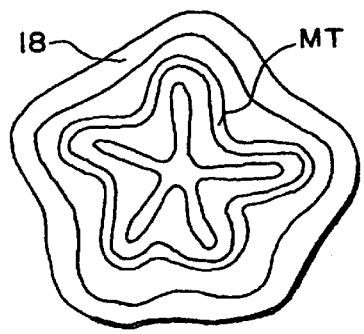
FIG. 66 is a side section view of the esophagus, showing the folds of mucosal tissue.

As FIG. 66 shows, mucosal tissue MT normally lays in folds in the area of the lower esophageal sphincter 18 and cardia 20, presenting a fully or at least partially closed closed path. In the preceding embodiments, various expandable structures are deployed to dilate the mucosal tissue MT for treatment. When dilated, the mucosal tissue folds expand and become smooth, to present a more uniform surface for submucosal penetration of the electrodes 66. The dilation mediates against the possibility that an electrode 66, when deployed, might slide into a mucosal tissue fold and not penetrate the underlying sphincter muscle.

(i) Rotational Deployment of Electrodes

Figure 67:
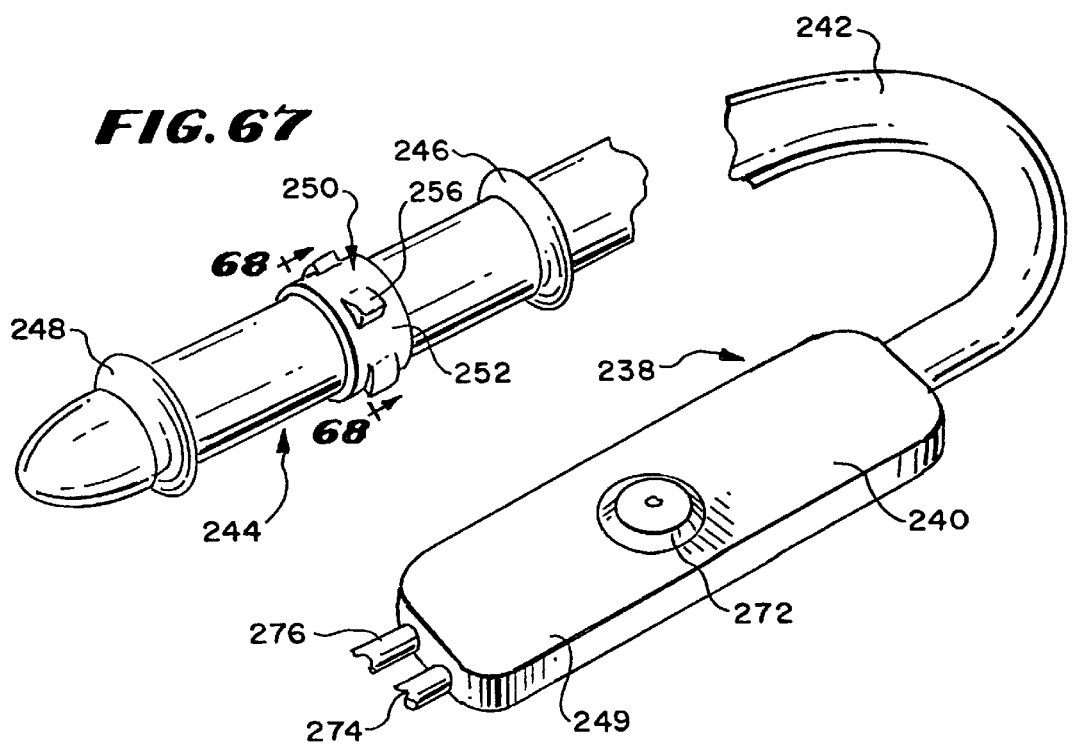
FIG. 67 is a perspective view of a device for treating body sphincters and adjoining tissue regions, which applies a vacuum to mucosal tissue to stabilize and present the tissue for the deployment of electrodes delivered by a rotating mechanism.
Figure 68:
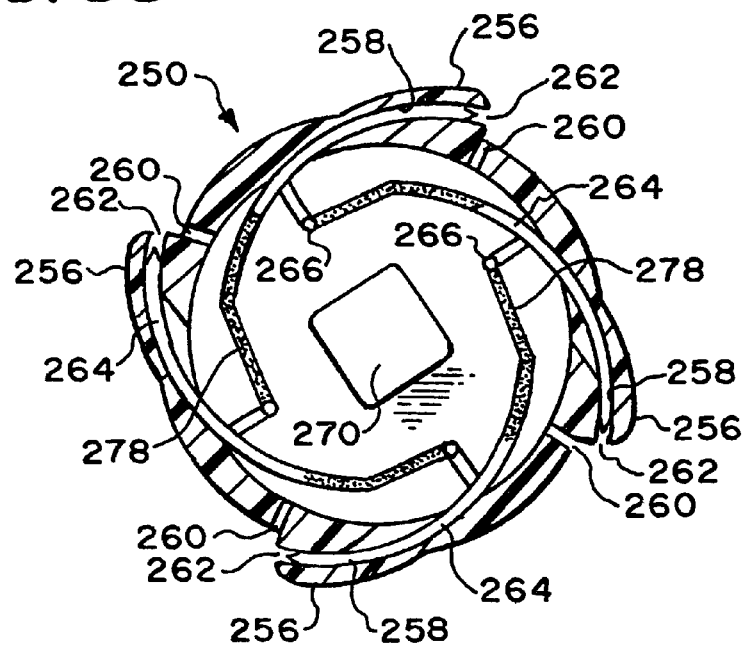
FIG. 68 is a section view of the rotating mechanism for deploying electrodes, taken generally along line 68—68 in FIG. 67 with the electrodes withdrawn.
Figure 69:
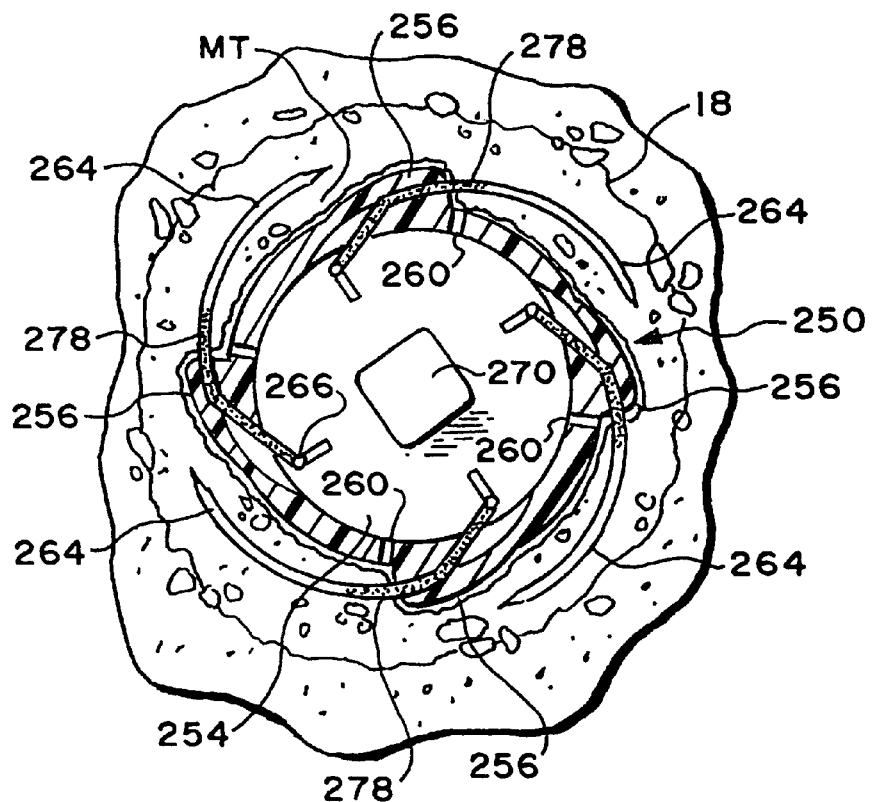
FIG. 69 is a view of the rotating mechanism shown in FIG. 68, with a vacuum applied to muscosal tissue and the electrodes extended.

FIGS. 67 to 69 show an alternative treatment device 238 suited for deployment in the lower esophageal sphincter 18, cardia 20, and other regions of the body to direct electrodes 66 into targeted submucosal tissue regions.

The device 238 includes a handle 248 (see FIG. 67) that carries a flexible catheter tube 242. The distal end of the catheter tube 242 carries an operative element 244.

The operative element 244 includes a proximal balloon 246 and a distal balloon 248. The balloons 246 and 248 are coupled to an expansion media by a port 276 on the handle 240.

An electrode carrier 250 is located between the balloons 246 and 248. As FIGS. 67 and 68 show, the carrier 250 includes a generally cylindrical housing 252 with an exterior wall 268. The housing 252 includes a series of circumferentially spaced electrode pods 256. Each pod 256 extends radially outward of the wall 268 of housing 252.

As FIGS. 68 and 69 show, each pod 256 includes an interior electrode guide bore 258. The guide bore 258 extends in a curved path through the pod 256 and terminates with an electrode port 262 spaced outward from the wall of the housing.

The housing 252 also includes a series of suction ports 260 (see FIGS. 68 and 69). Each suction port 260 is located flush with the housing wall 268 close to an electrode port 262. The suction ports 260 are coupled to a source of negative pressure through a port 274 on the handle 240.

A driver disk 254 is mounted for rotation within the housing 252. Electrodes 264 are pivotally coupled to the driver disk 254 on pins 266 arranged in an equally circumferentially spaced pattern.

The electrodes 264 can be formed from various energy transmitting materials, e.g., 304 stainless steel. The electrodes 264 are coupled to the generator 38, preferable through the controller 52.

The electrodes 264 have sufficient distal sharpness and strength to penetrate a desired depth into the smooth muscle of the esophageal or cardia 20 apply energy from the generator 38.

As previously described with respect to other embodiments, an electrical insulating material 278 (see FIGS. 68 and 69) is coated about the proximal end of each electrode 264. When the distal end of the electrode 264 penetrating the smooth muscle of the esophageal sphincter 18 or cardia 20 transmits radio frequency energy, the material 278 insulates the mucosal surface of the esophagus 10 or cardia 20 from direct exposure to the radio frequency energy to prevent thermal damage to the mucosal surface. As previously described, the mucosal surface can also be actively cooled during application of radio frequency energy, to further protect the mucosal surface from thermal damage.

Each electrode 264 is biased with a bend, to pass from the pin 266 in an arcuate path through the electrode guide bore 258 in the associated pod 256. Rotation of the driver disk 254 in one direction (which is clockwise in FIG. 68) moves the electrodes 264 through the bores 258 outward of the carrier 250 (as FIG. 69 shows). Opposite rotation of the driver disk 254 (which is counterclockwise in FIG. 68) moves the electrodes 264 through the bores 258 inward into the carrier 250 (as FIGS. 67 and 68 show).

A drive shaft 270 is coupled to the driver disk 254 to affect clockwise and counterclockwise rotation of the disk 254. A control knob 272 on the handle 240 (see FIG. 67) is coupled to the drive shaft 254 to extend and retract the electrodes 264.

In use, the carrier 250 is located at the desired treatment site, e.g., in the region of the lower esophageal sphincter 18. The balloons 246 and 248 are expanded to seal the esophagus in the region between the balloons 246 and 248.

A vacuum is then applied through the suction ports 260. The vacuum evacuates air and fluid from the area of the esophageal lumen surrounding the carrier 250. This will cause the surrounding mucosal tissue to be drawn inward against the wall 268 of the housing 252 (see FIG. 69), to conform and be pulled tightly against the pods 256.

Applying a vacuum to draw mucosal tissue inward against the pods 256 causes the tissue to present a surface nearly perpendicular to the electrode ports 262 (see FIG. 69). Operation of the driver disk 254 moves the electrodes 264 through the ports 262, in a direct path through mucosal tissue and into the underlying sphincter muscle. Due to the direct, essentially perpendicular angle of pentration, the electrode 264 reaches the desired depth in a short distance (e.g., less than 3 mm), minimizing the amount of insulating material 278 required.

The application of vacuum to draw mucosal tissue against the pods 256 also prevents movement of the esophagus while the electrodes 264 penetrate tissue. The counter force of the vacuum resists tissue movement in the direction of electrode penetration. The vacuum anchors the surrounding tissue and mediates against the "tenting" of tissue during electrode penetration. Without tenting, the electrode 264 penetrates mucosal tissue fully, to obtain a desired depth of penetration.

(ii) Straight Deployment of Electrodes

Figure 70:
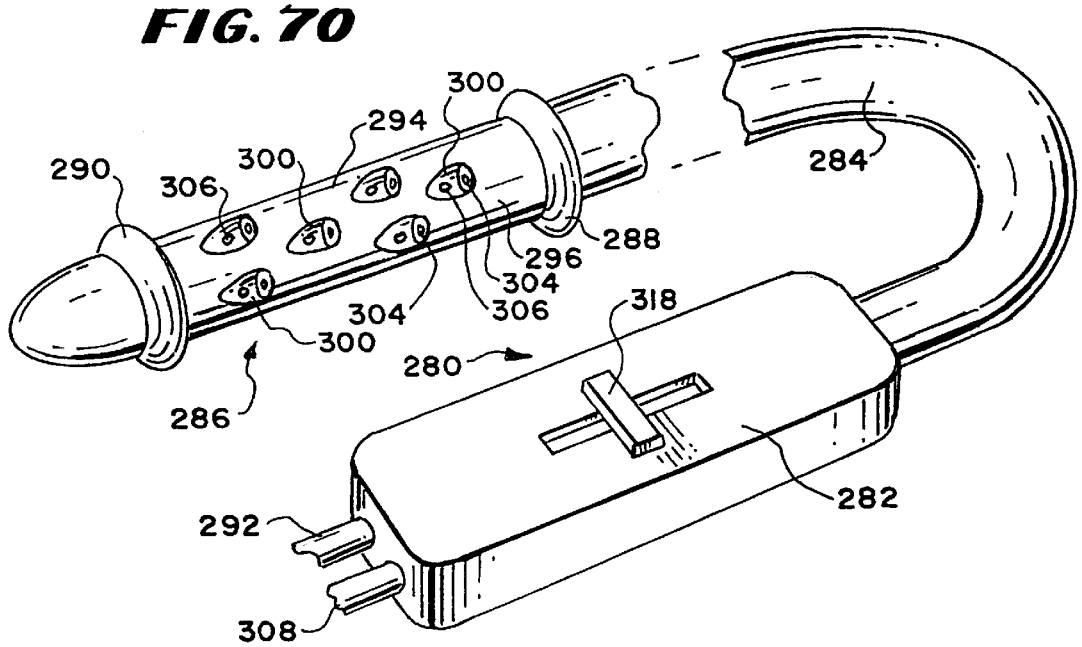
FIG. 70 is a perspective view of a device for treating body sphincters and adjoining tissue regions, which applies a vacuum to mucosal tissue to stabilize and present the tissue for the deployment of straight electrodes.
Figure 71:
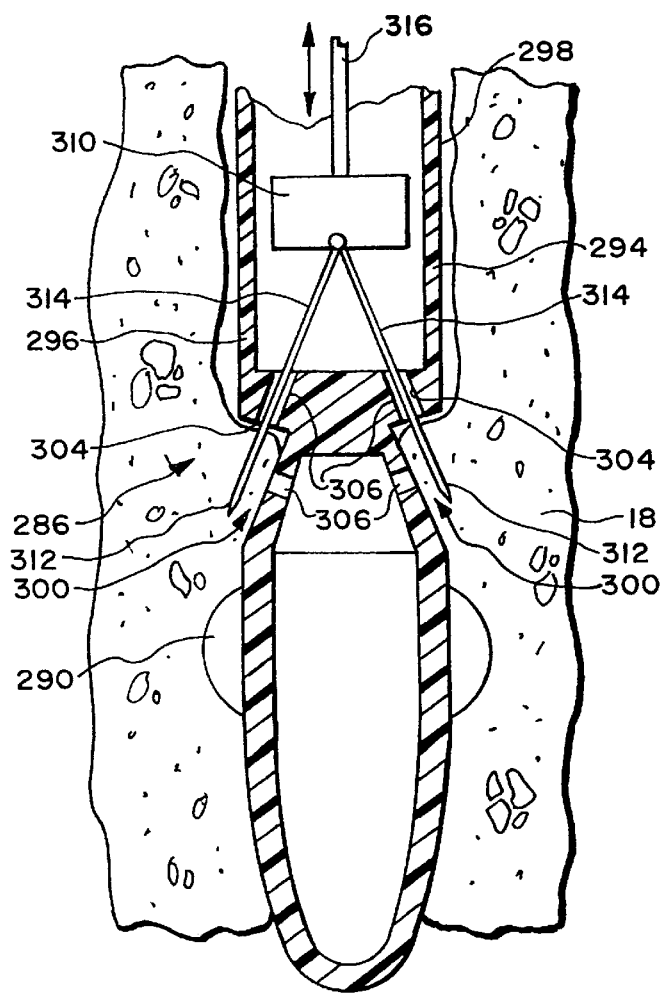
FIG. 71 is a side section view of the electrode deployment mechanism of the device shown in FIG. 70.

FIGS. 70 and 71 show another alternative treatment device 280 suited for deployment in the lower esophageal sphincter 18, cardia 20, and other regions of the body to direct electrodes 66 into targeted submucosal tissue regions.

The device 280 includes a handle 282 (see FIG. 70) that carries a flexible catheter tube 284. The distal end of the catheter tube 284 carries an operative element 286.

The operative element 286 includes a proximal balloon 288 and a distal balloon 290. The balloons 288 and 290 are coupled to an expansion media by a port 292 on the handle 284.

An electrode carrier 294 is located between the balloons 246 and 248. The carrier 294 includes a generally cylindrical housing 296 with an exterior wall 298 (see FIG. 71). The housing 296 includes a series of circumferentially and axially spaced recesses 300 in the wall 298 (best shown in FIG. 70).

As FIG. 71 shows, an electrode guide bore 302 extends through the wall 298 and terminates with an electrode port 304 in each recess 300. The axis of each guide bore 302 is generally parallel to the plane of the corresponding recess 300.

The housing 296 also includes a series of suction ports 306, one in each recess 300. The suction ports 306 are coupled to a source of negative pressure through a port 308 on the handle 282.

An electrode mount 310 (see FIG. 71) is mounted for axial movement within the housing 296. Electrodes 312 are pivotally coupled to the mount 310.

The electrodes 312 can be formed from various energy transmitting materials, e.g., 304 stainless steel. The electrodes 312 are coupled to the generator 38, preferable through the controller 52.

The electrodes 312 have sufficient distal sharpness and strength to penetrate a desired depth into the smooth muscle of the esophageal or cardia 20 apply energy from the generator 38. As previously described with respect to other embodiments, an electrical insulating material 314 (see FIG. 71) is coated about the proximal end of each electrode 312.

Each electrode 312 is generally straight, to pass from the mount 310 through the electrode guide bore 302. Axial movement of the mount 310 toward the guide bores 302 extends the electrodes 312 outward into the recesses 300, as FIG. 71 shows. Opposite axial movement of the mount 310 withdraws the electrodes 312 through the bores 302 inward from recesses 300 (as FIG. 70 shows).

A stylet 316 (see FIG. 71) is coupled to the mount 310 to affect axial movement of the mount 310. A push-pull control knob 318 on the handle 282 is coupled to the stylet 316 to extend and retract the electrodes 264. Alternatively, a spring loaded mechanism can be used to "fire" the mount 310 to deploy the electrodes 312.

In use, the carrier 294 is located at the desired treatment site, e.g., in the region of the lower esophageal sphincter. The balloons 288 and 290 are expanded to seal the esophagus in the region between the balloons 288 and 290.

A vacuum is then applied through the suction ports 292. The vacuum evacuates air and fluid from the area of the esophageal lumen surrounding the carrier 294. This will cause the surrounding mucosal tissue to be drawn inward into the recesses, to conform and be pulled tightly against the recesses 300, as FIG. 71 shows.

Applying a vacuum to draw mucosal tissue inward into the recesses 300 causes the tissue to present a surface nearly perpendicular to the electrode ports 304, as FIG. 71 shows. Operation of the mount 310 moves the electrodes 312 through the ports 304, in a path through mucosal tissue and into the underlying sphincter muscle that is generally parallel to the axis of the esophageal lumen.

In the same manner described with regard to the preceding embodiment, the application of vacuum to draw mucosal tissue into the recesses 300 also anchors the carrier 294 in the esophagus while the electrodes 312 penetrate tissue. Ribs and the like can also be provided in the recesses 300 or along the wall 298 of the housing 296 to enhance the tissue anchoring effect. The counter force of the vacuum resists tissue movement in the direction of electrode penetration. The vacuum anchors the surrounding tissue and mediates against the "tenting" of tissue during electrode penetration. The electrodes 312 penetrates mucosal tissue fully, to obtain a desired depth of penetration.

H. Visualization

Visualization of the targeted tissue site before, during, and after lesion formation is desirable.

(i) Endoscopy

As earlier shown in FIGS. 9 and 10, a separately deployed endoscope 84, carried by a flexible catheter tube 86, is used to visualize the targeted site. In this embodiment, the operative element 36 is deployed separately, by means of a separate catheter tube 30.

In an alternative embodiment (shown in FIGS. 46 to 49), a treatment device 26 is deployed over the same catheter tube 86 that carries the endoscope 84. In effect, this arrangement uses the flexible catheter tube 86 of the endoscope 84 as a guide wire.

Figure 47:
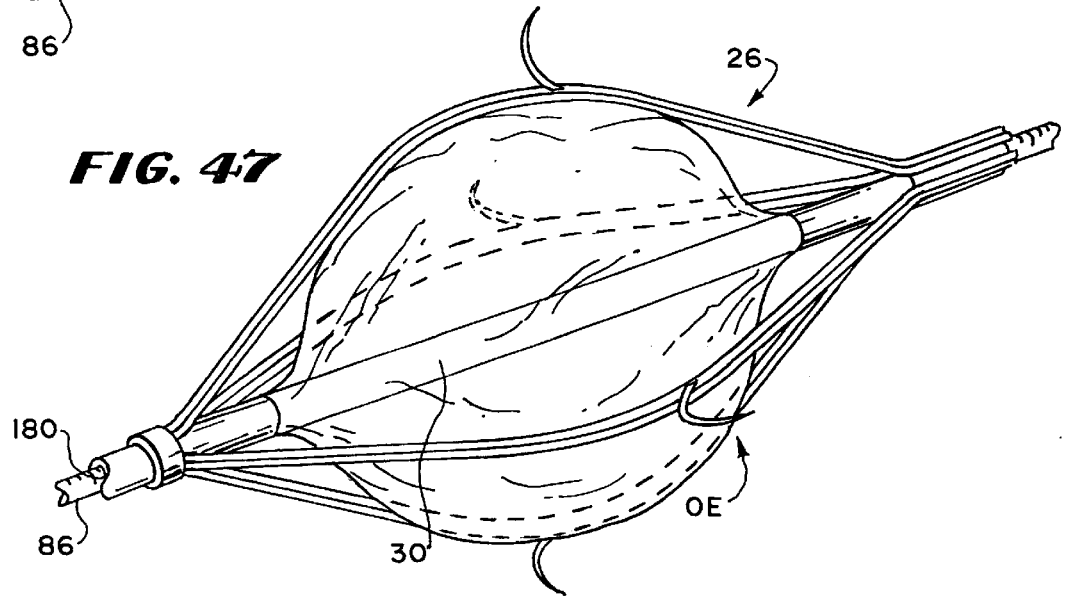
FIG. 47 is a perspective view of the operative element shown in FIG. 48 in an expanded condition and with the electrodes extended for use.

In this embodiment, the treatment device 26 can carry any suitable operative element (which, for this reason, is generically designated OE in FIGS. 46 to 49). As FIGS. 47 and 47 show, the catheter tube 30 passes through and beyond the interior of the operative element OE. The catheter tube 30 further includes a central lumen 180, which is sized to accommodate passage of the flexible catheter tube 86 carrying the endoscope 84.

Figure 48:
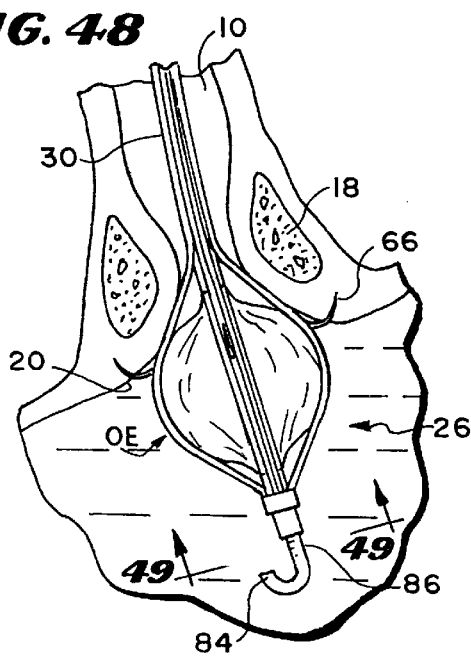
FIG. 48 is an enlarged view of the operative element shown in FIG. 47, when expanded into contact with muscosal tissue in the cardia and with the electrodes extended to create lesions in the smooth muscle of the cardia.

As shown in FIG. 48, once the endoscope 84 is deployed in the manner shown in FIGS. 9 and 10, the operative element OE can be passed over the catheter tube 86 to the targeted tissue region. In FIG. 48, the targeted region is shown to be the cardia 20.

Figure 49:
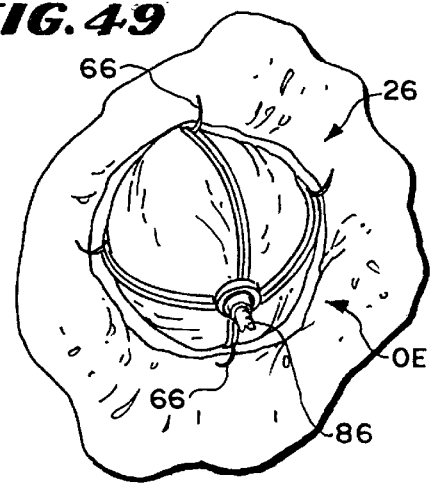
FIG. 49 is an end view of the operative element taken generally along line 49—49 in FIG. 48, as viewed from the retroflex endoscope over which the operative element is deployed for use.

In use, the endoscope 86 extends distally beyond the operative element OE. By retroflexing the endoscope 86, as FIGS. 48 and 49 show, the physician can continuously monitor the placement of the operative element OE, the extension of the electrodes 66, and the other steps of the lesion formation process already described.

Figure 50:
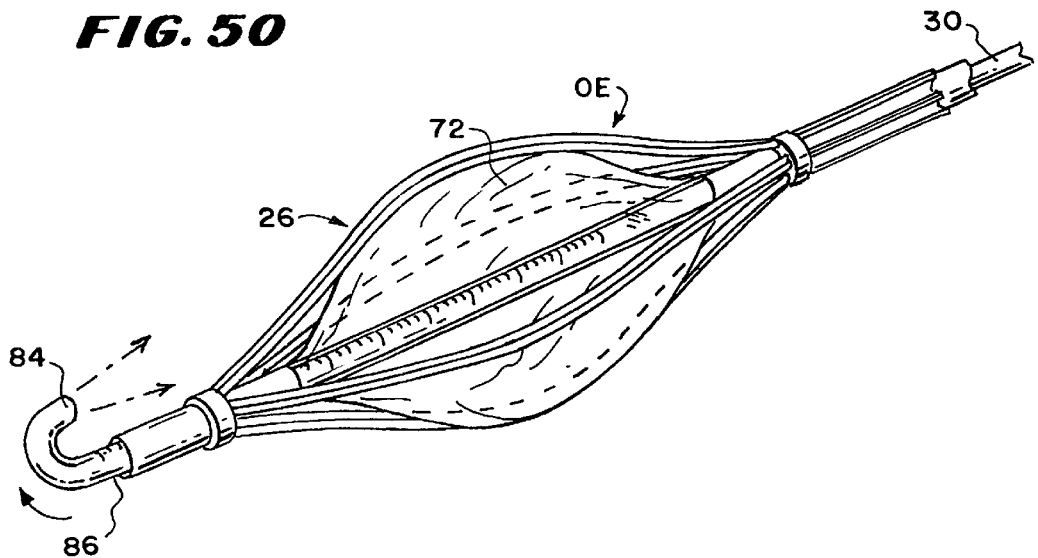
FIG. 50 is a perspective view of the operative element of the type shown in FIG. 47, deployed over a flexible endoscope, and including a transparent region within the operative element to permit endoscopic viewing from within the operative element.
Figure 51:
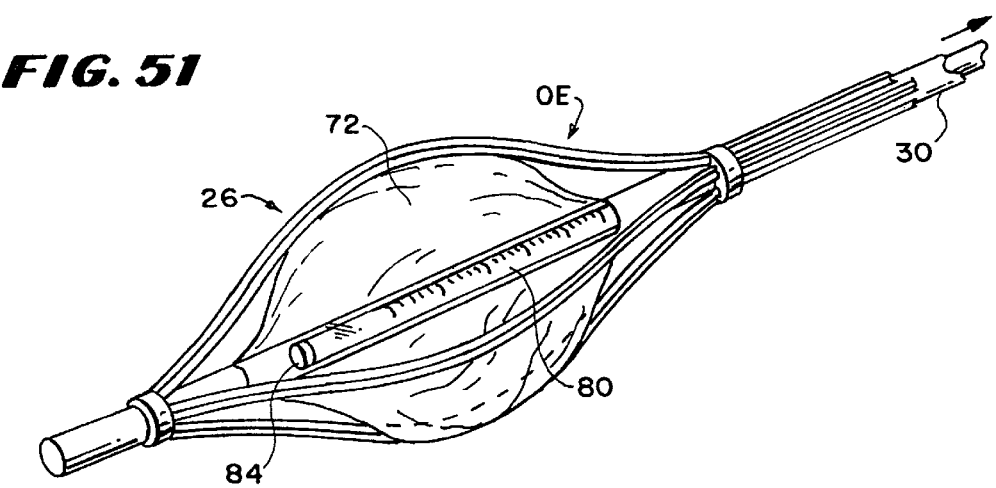
FIG. 51 is a perspective view of the operative element shown in FIG. 50, with the endoscope positioned within the operative element for viewing.

When the operative element OE includes the expandable balloon structure 72 (see FIGS. 50 and 51), the structure 72 and the extent of the catheter tube 30 passing through it, can be formed of a material that is transparent to visible light. In this arrangement, the physician can retract the endoscope 84 into expandable structure 72 (as FIG. 51 shows). The physician can then monitor the manipulation of the operative element OE and other steps in the lesion formation process from within the balloon structure 72. Any portion of the catheter tube 30 can be made from a transparent material, so the physician can visualize at other locations along its length.

Figure 52:
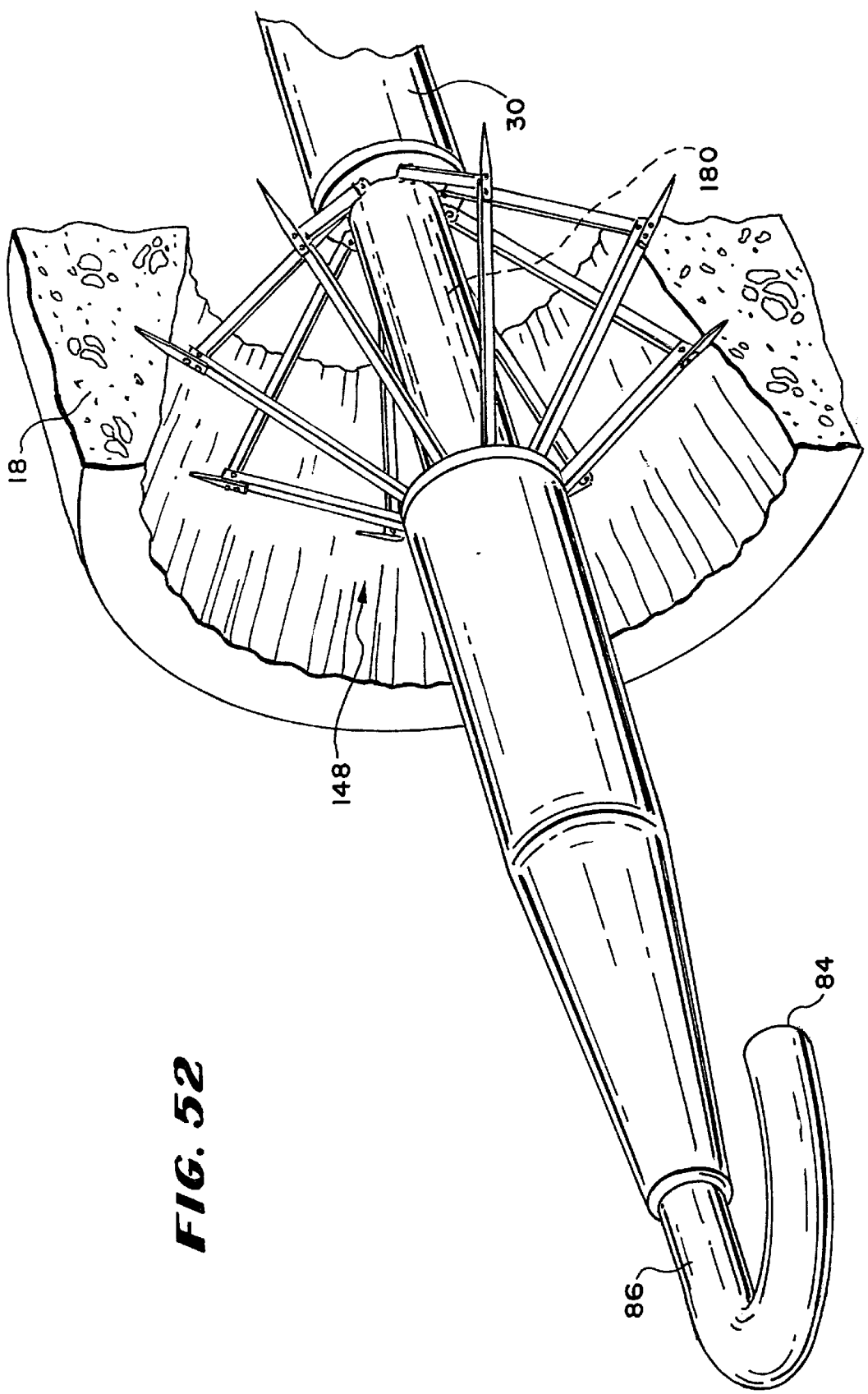
FIG. 52 is an enlarged view of an operative element comprising a mechanically expandable basket deployed over a flexible endoscope and with the electrodes penetrating the lower esophageal sphincter to create lesions.

As FIG. 52 shows, the mechanically expanded basket 148 (shown earlier in FIGS. 41 and 42) can be likewise be modified for deployment over the catheter tube 86 that carries the flexible endoscope 84. In this arrangement, the interior lumen 180 extends through the catheter tube 30, the basket 148, and beyond the basket hub 152. The lumen 180 is sized to accommodate passage of the endoscope 84.

Figure 62:
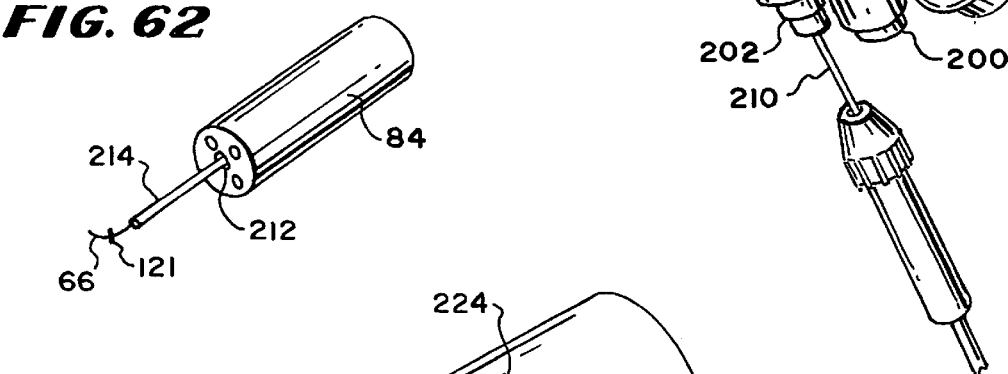
FIG. 62 a perspective view of an operative element for treating body sphincters and adjoining tissue regions, deployed through an endoscope.

In another embodiment (see FIG. 62), the endoscope 84 itself can include an interior lumen 212. A catheter tube 214, like that previously shown in FIG. 38, can be sized to be passed through the interior lumen 212 of the endoscope 84, to deploy a mono-polar electrode 66 (or a bipolar pair of electrodes) into penetrating contact with a desired tissue region. As FIG. 62 shows, the electrode 66 can carry a limit collar 121 to resist advancement of the electrode 66 beyond a desired penetration depth.

In another embodiment, to locate the site of lower esophageal sphincter 18 or cardia 20, a rigid endoscope can be deployed through the esophagus of an anesthetized patient. Any operative element OE can be deployed at the end of a catheter tube to the site identified by rigid endoscopy, to perform the treatment as described. In this arrangement, the catheter tube on which the operative element is deployed need not be flexible. With an anesthetized patient, the catheter tube that carries the operative element OE can be rigid.

With rigid endoscopy, the catheter tube can be deployed separately from the endoscope. Alternatively, the catheter tube can include an interior lumen sized to pass over the rigid endoscope.

(ii) Fluoroscopy

Fluoroscopy can also be used to visual the deployment of the operative element OE. In this arrangement, the operative element OE is modified to carry one or more radiopaque markers 182 (as FIG. 24 shows) at one or more identifiable locations, e.g, at the distal hub 60, or proximal base 62, or both locations.

With a patient lying on her left side upon a fluoroscopy table, the physician can track movement of the radiopaque markers 182 to monitor movement and deployment of the operative element OE. In addition, the physician can use endoscopic visualization, as previously described.

(iii) Ultrasound

The catheter tube can carry an ultrasound transducer 184 (as FIG. 21 shows) adjacent the proximal or distal end of the operative element OE. The physician can observe the transesophageal echo as a real time image, as the operative element OE is advanced toward the lower esophageal sphincter 18. The real time image reflects the thickness of the esophageal wall.

Loss of the transesophageal echo marks the passage of the ultrasound transducer 184 beyond lower esophageal sphincter 18 into the stomach 12. The physician pulls back on the catheter tube 30, until the transesophageal echo is restored, thereby marking the situs of the lower esophageal sphincter 18.

With the position of the sphincter localized, the physician can proceed to expand the structure 72, deploy the electrodes 66, and perform the steps of procedure as already described. Changes in the transesophageal echo as the procedure progresses allows the physician to visualize lesion formation on a real time basis.

I. The Graphical User Interface (GUI)

Figure 72A:
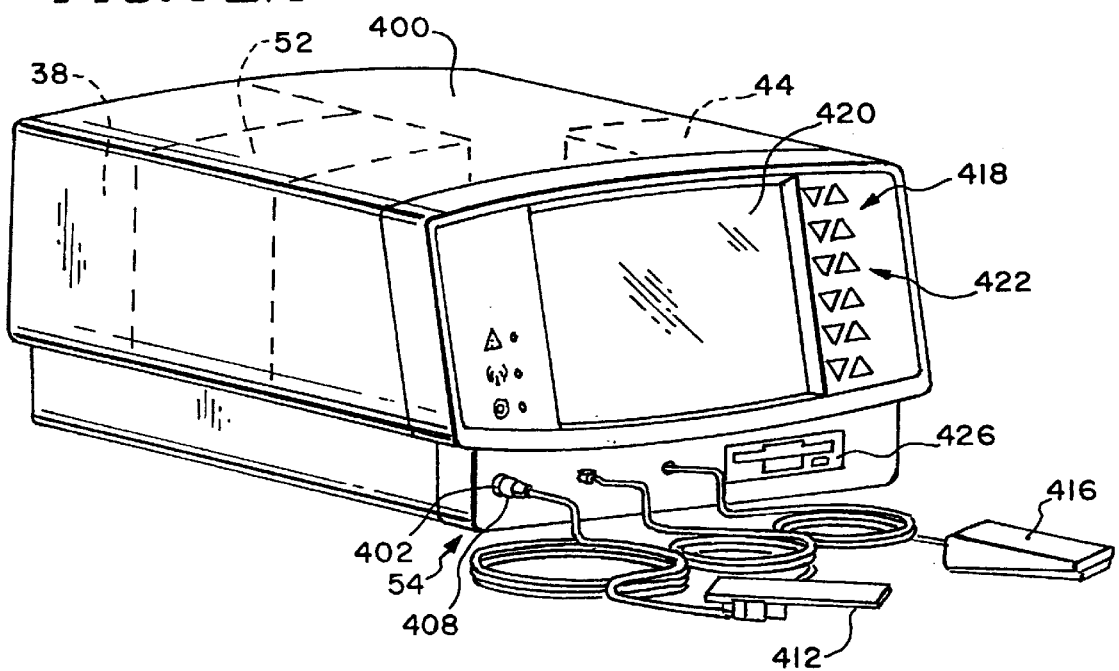
FIGS. 72A and 72B are, respectively, left and right perspective views of an integrated device for treating body sphincters and adjoining tissue regions, and having graphical user interface.
Figure 72B:
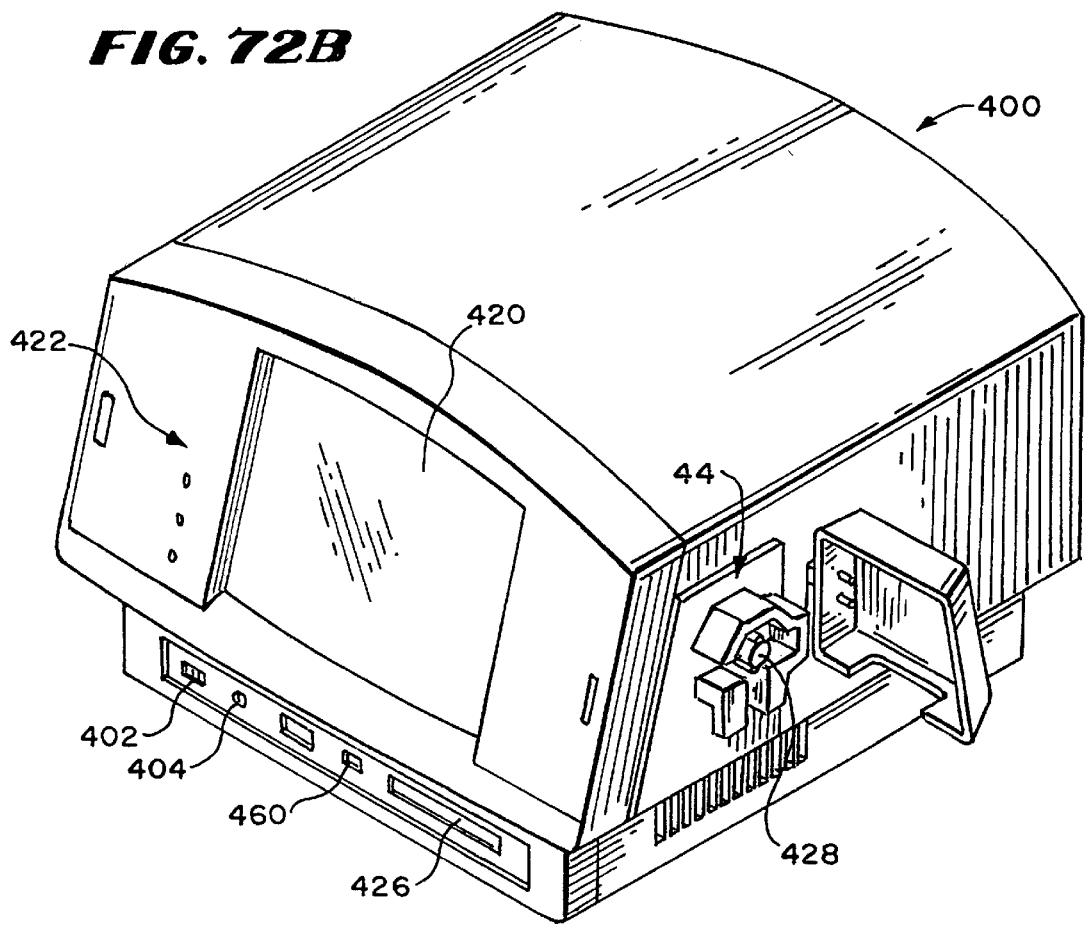

In the illustrated embodiment (see FIGS. 72A and 72B), the radio frequency generator 38, the controller 52 with I/O device 54, and the fluid delivery apparatus 44 (for the delivery of cooling liquid) are integrated within a single housing 400.

The I/O device 54 includes input connectors 402, 404, and 406. The connector 402 accepts an electrical connector 408 coupled to a given treatment device TD. The connector 404 accepts an electrical connector 410 coupled to a patch electrode 412 (for mono-polar operation). The connector 406 accepts an pneumatic connector 414 coupled to a conventional foot pedal 416. These connectors 402, 404, and 406 couple these external devices to the controller 52. The I/O device 54 also couples the controller 54 to an array of membrane keypads 422 and other indicator lights on the housing 400 (see FIG. 73), for entering and indicating parameters governing the operation of the controller 52.

Figure 82:
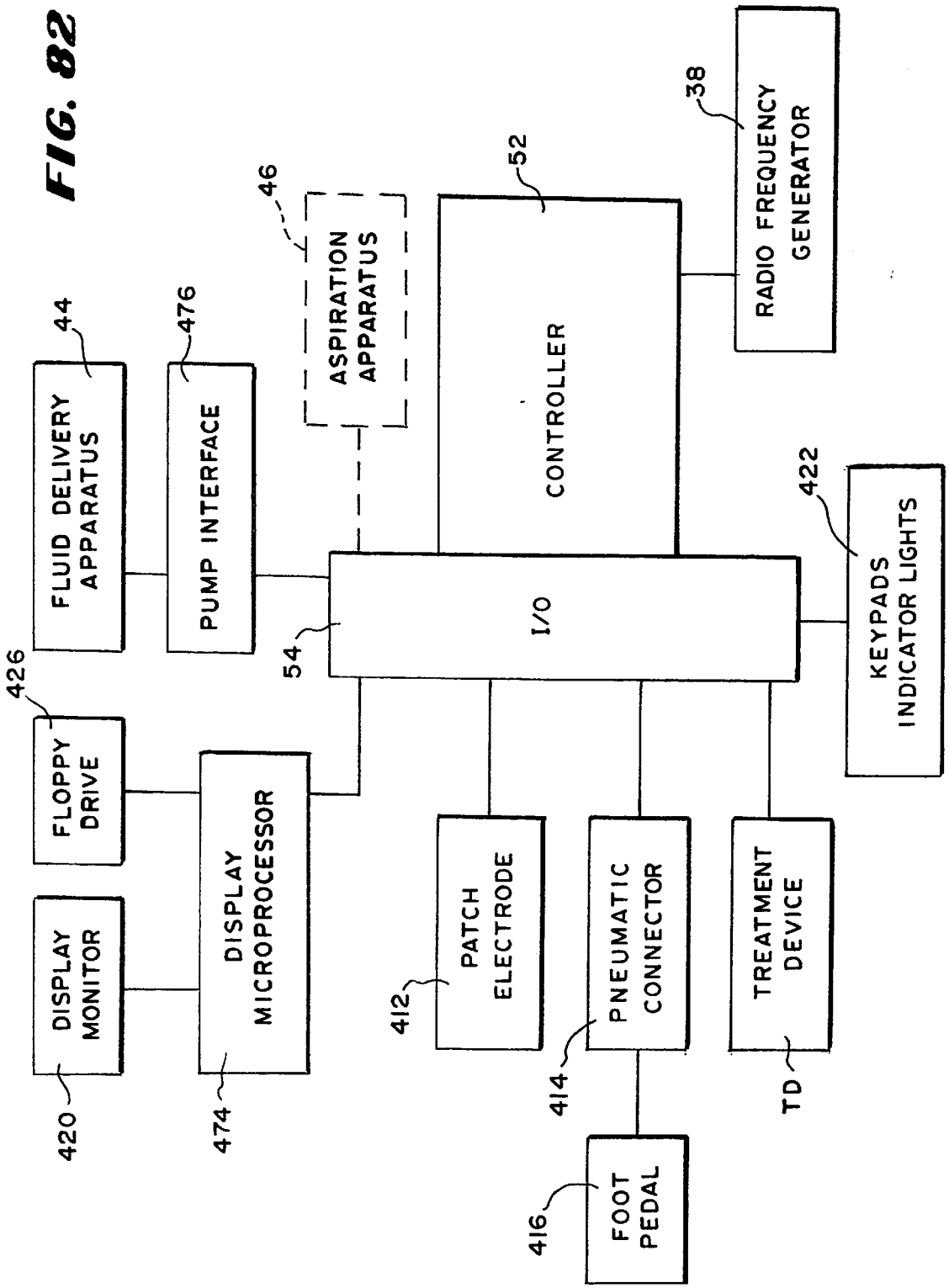
FIG. 82 is a schematic view of the control architecture that the integrated device and associated graphical user interface shown in FIGS. 72A, 72B, and 73 incorporate.

The I/O device 54 also couples the controller 52 to a display microprocessor 474, as FIG. 82 shows. In the illustrated embodiment, the microprocessor 474 comprises, e.g., a dedicated Pentium®-based central processing unit.

The controller 52 transmits data to the microprocessor 474, and the microprocessor 474 acknowledges correct receipt of the data and formats the data for meaningful display to the physician. In the illustrated embodiment, the dedicated display microprocessor 474 exerts no control over the controller 52.

In the illustrated embodiment, the controller 52 comprises an 68HC11 processor having an imbedded operating system. Alternatively, the controller 52 can comprise another style of processor, and the operating system can reside as process software on a hard drive coupled to the CPU, which is down loaded to the CPU during system initialization and startup.

The display microprocessor 474 is coupled to a graphics display monitor 420. The controller 52 implements through the display microprocessor 474 a graphical user interface, or GUI 424, which is displayed on the display monitor 420. The GUI 424 can be realized, e.g., as a "C" language program implemented by the microprocessor 474 using the MS WINDOWS™ or NT application and the standard WINDOWS 32 API controls, e.g., as provided by the WINDOWS™ Development Kit, along with conventional graphics software disclosed in public literature.

The display microprocessor 474 is also itself coupled to a data storage module or floppy disk drive 426. The display microprocessor 474 can also be coupled to a keyboard, printer, and include one or more parallel port links and one or more conventional serial RS-232C port links or Ethernet™ communication links.

The fluid delivery apparatus 44 comprises an integrated, self priming peristaltic pump rotor 428 with a tube loading mechanism, which are carried on a side panel of the housing 400. Other types of non-invasive pumping mechanisms can be used, e.g., a syringe pump, a shuttle pump, or a diaphragm pump.

In the illustrated embodiment, the fluid delivery apparatus 44 is coupled to the I/O device 54 via a pump interface 476. The pump interface 476 includes imbedded control algorithms that monitor operation of the pump rotor 428.

For example, the pump interface 476 can monitor the delivery of electrical current to the pump rotor 428, to assure that the rotor 428 is operating to achieve a desired flow rate or range of flow rates during use, or, upon shut down, the rotor 428 has stopped rotation. An optical encoder or magnetic Halls effect monitor can be used for the same purpose.

Alternatively, a flow rate transducer or pressure transducer, or both, coupled to the pump interface 476, can be placed in line along the pump tubing, or in the treatment device TD itself, to monitor flow rate.

Flow rate information acquired from any one of these monitoring devices can also be applied in a closed loop control algorithm executed by the controller 52, to control operation of the pump rotor 428. The algorithm can apply proportional, integral, or derivative analysis, or a combination thereof, to control operation of the pump rotor 428.

In the illustrated embodiment, it is anticipated that the physician will rely upon the vacuum source typically present in the physician's suite as the aspiration apparatus 46. However, it should be appreciated that the device 400 can readily integrate the aspiration apparatus 46 by selectively reversing the flow direction of the pump rotor 428 (thereby creating a negative pressure) or by including an additional dedicated pump rotor or equivalent pumping mechanism to perform the aspiration function.

In the illustrated embodiment, the integrated generator 38 has four independent radio frequency channels. Each channel is capable of supplying up to 15 watts of radio frequency energy with a sinusoidal waveform at 460 kHz. As before explained, the four channels of the generator 38 can operate four electrodes in either a monopolar or bipolar mode. As also explained earlier, the four channels can also be configured to operate eight electrodes either in a monopolar mode or a bipolar mode.

The integrated controller 52 receives two temperature measurements through the I/O device 54 for each channel, one from the tip of each electrode on the treatment device TD, and one from tissue surrounding the electrode. The controller 52 can regulate power to the electrodes in a close-loop based upon the sensed tip temperature, or the sensed tissue temperature, or both, to achieve and maintain a targeted tip tissue temperature at each electrode. The controller 52 can also regulate power to the pump rotor 428 in a closed-loop based upon the sensed tip temperature, or the sensed tissue temperature, or both, to achieve an maintain a targeted tissue temperature at each electrode. Alternatively, or in combination, the physician can manually adjust the power level or pump speed based upon a visual display of the sensed tip and tissue temperatures.

Figure 73:
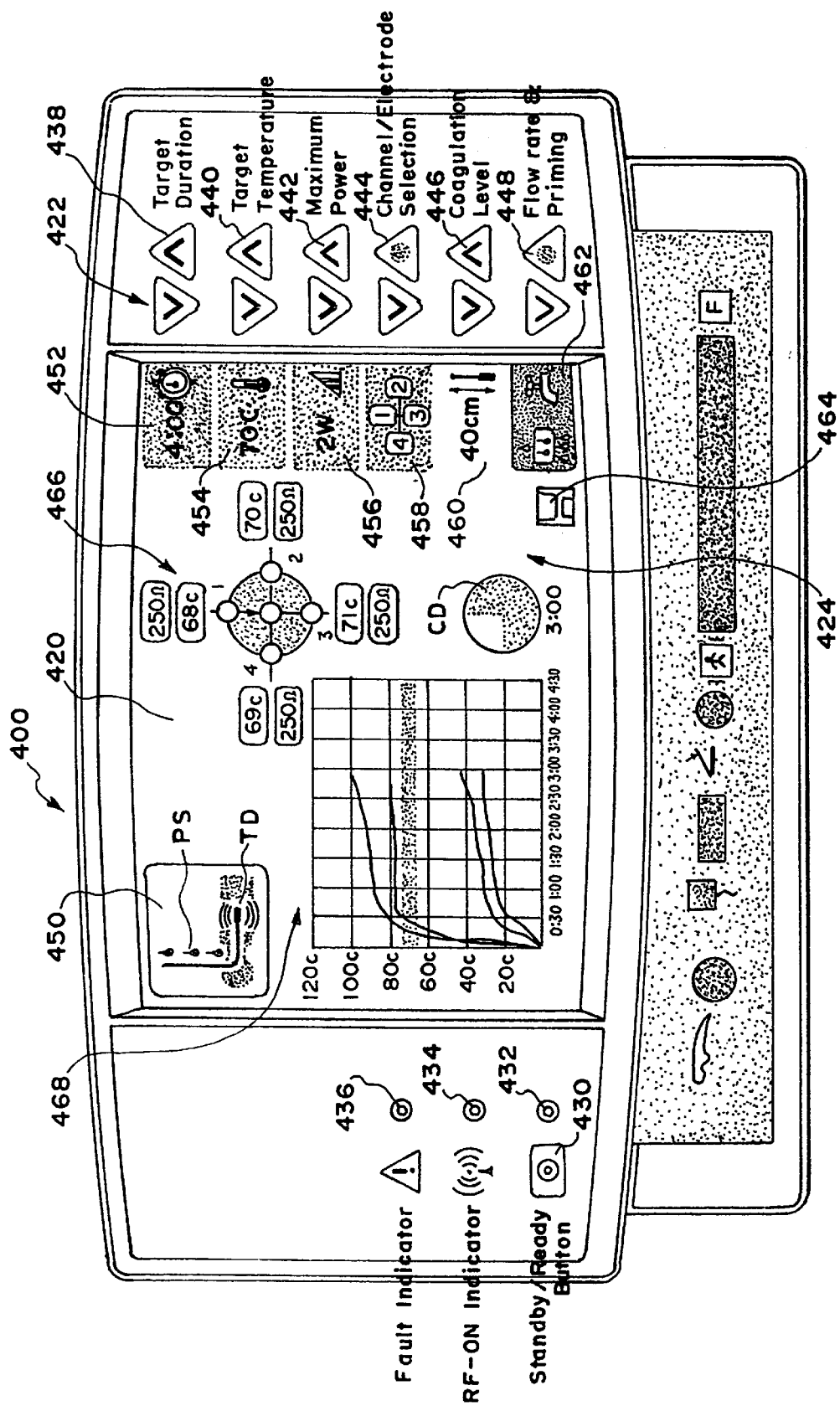
FIG. 73 is a front view of the device shown in FIGS. 72A and 72B showing the components of the graphical user interface.

As FIG. 73 best shows, the membrane keypads 422 and other indicators on the front panel of the device 400 show the various operational parameters and operating states and allow adjustments to be made. In the illustrated embodiment, as shown in FIG. 73, the keypads 422 and indicators include:

1. Standby/Ready Button 430, which allows switching from one mode of operation to another, as will be described later.

2. Standby/Ready Indicator 432, which displays a green light after the device 400 passes a self test upon start up.

3. RF On Indicator 434, which displays a blue light when radio frequency energy is being delivered.

4. Fault Indicator 436, which displays a red light when an internal error has been detected. No radio frequency energy can be delivered when the Fault Indicator 436 is illuminated.

5. Target Duration Keys 438, which allow increases and decreases in the target power duration at the start or during the course of a procedure.

6. Target Temperature Keys 440, which allow increases and decreases in the target temperature at the start or during the course of a procedure.

7. Maximum Power Keys 442, which allow increases and decreases in the maximum power setting at the start or during the course of a procedure.

8. Channel Selection Keys 444, which allow selection of any or all power channels.

9. Coagulation Level Keys 446, which manually increases and decreases the magnitude of the indicated depth of insertion of the electrodes within the esophagus. This depth is determined, e.g., by visually gauging the measured markings along the length of the catheter tube of the treatment device TD, as previously described. Alternatively, the coagulation level can be automatically detected by, e.g., placing optical, mechanical, or magnetic sensors on the mouth piece 82, which detect and differentiate among the measured markings along the catheter tube of the treatment device TD to read the magnitude of the depth of insertion.

10. Flow Rate and Priming Keys 448, which allow for selection of three internally calibrated flow rates, low (e.g., 15 ml/min), medium (e.g., 30 ml/min), and high (e.g., 45 ml/min). Pressing and holding the "Up" key activates the pump at a high flow rate for priming, overruling the other flow rates until the "Up" key is released.

In the illustrated embodiment, the graphics display monitor 420 comprises an active matrix LCD display screen located between the membrane keypads 422 and other indicators on the front panel. The GUI 424 is implemented by showing on the monitor 420 basic screen displays. In the illustrated embodiment, these displays signify four different operating modes: Start-Up, Standby, Ready, RF-On, and Pause.

(i) Start Up

Upon boot-up of the CPU, the operating system implements the GUI 424. The GUI 424 displays an appropriate start-up logo and title image (not shown), while the controller 52 performs a self-test. A moving horizontal bar or the like can be displayed with the title image to indicate the time remaining to complete the start-up operation.

(ii) Standby

Figure 74:
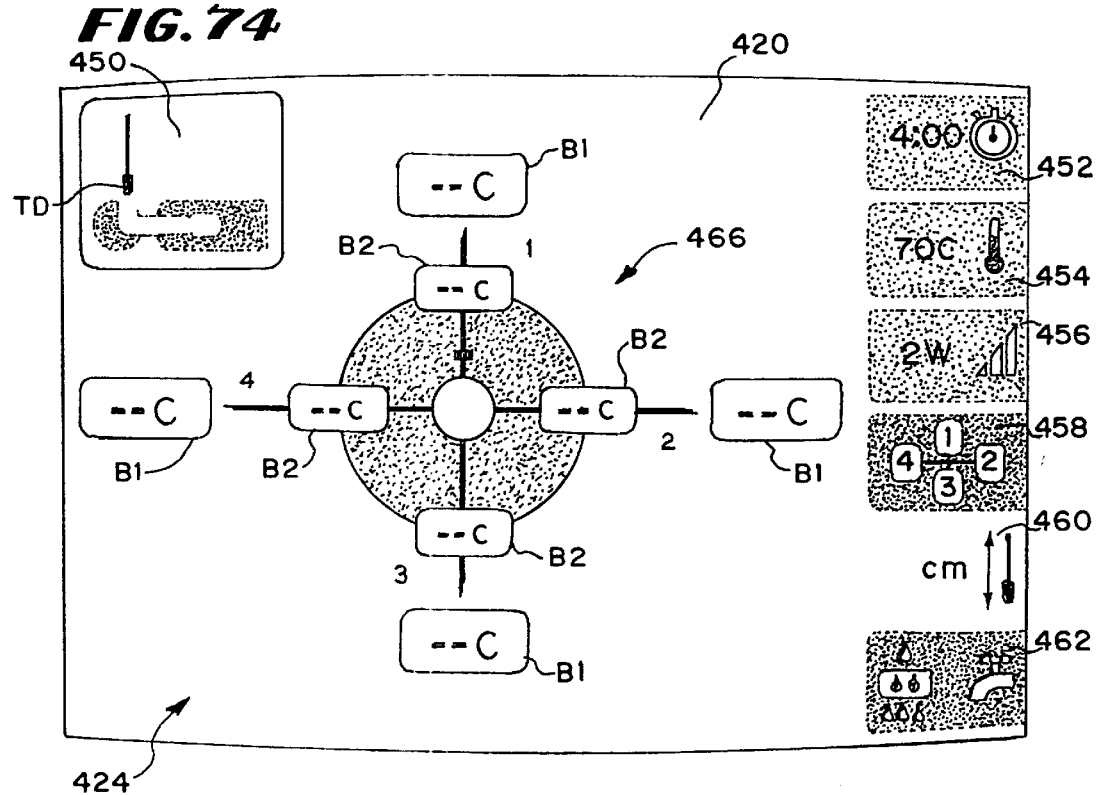
FIG. 74 is a view of the graphical user interface shown in FIG. 73 showing the Standby screen before connection of a treatment device.

Upon completion of the start-up operation, the Standby screen is displayed, as shown in FIG. 74. No radio frequency energy can be delivered while the Standby screen is displayed.

There are various icons common to the Standby, Ready, RF-On, and Pause screens.

The Screen Icon 450 is an icon in the left hand corner of the monitor 420, which indicates the operating condition of the treatment device TD and its position inside or outside the esophagus. In FIG. 74, the treatment device TD is shown to be disconnected and outside the esophagus. Pressing the "Up" priming key 448, to cause cooling liquid to flow through the treatment device TD, causes an animated priming stream PS to be displayed along the treatment device TD in the icon, as FIG. 73 shows. The animated priming stream PS is displayed in the Screen Icon 450 whenever the pump rotor 428 is operating to indicate the supply of cooling fluid through the treatment TD.

There are also parameter icons designating target duration 452, target temperature 454, maximum power 456, channel selection 458, coagulation level 460, and flow rate/priming 462. These icons are aligned with, respectively, the corresponding Target Duration Keys 438, Target Temperature Keys 440, Maximum Power Keys 442, Channel Selection Keys 444, Coagulation Level Keys 446, and Flow Rate and Priming Keys 448. The icons 452 to 462 indicate current selected parameter values. The flow rate/priming icon 462 shows the selected pump speed by highlighting a single droplet image (low speed), a double droplet image (medium speed), and a triple droplet image (high speed).

There is also a floppy disk icon 464 that is normally dimmed, along with the coagulation level icon 460, until a floppy disk is inserted in the drive 426. When a floppy disk is inserted in the drive 426, the icons 460 and 464 are illuminated (see FIG. 73), and data is saved automatically after each application of radio frequency energy (as will be described later).

There is also an Electrode Icon 466. The Electrode Icon 466 comprises an idealized graphical image, which spatially models the particular multiple electrode geometry of the treatment device TD selected to be deployed in the esophagus. As FIG. 74 shows, four electrodes are shown in the graphic image of the Icon 466, which are also spaced apart by 90 degrees. This graphic image is intended to indicate that the selected treatment device TD has the geometry of the four-electrode configuration shown, e.g., in FIG. 5.

For each electrode, the Icon 466 presents in a spatial display the magnitude of tip temperature as actually sensed (in outside box B1) and the magnitude of tissue temperatures as actually sensed (in inside box B2). Until a treatment device TD is connected, two dashes appear in the boxes B1 and B2. The existence of a faulty electrode in the treatment device will also lead to the same display.

Figure 75:
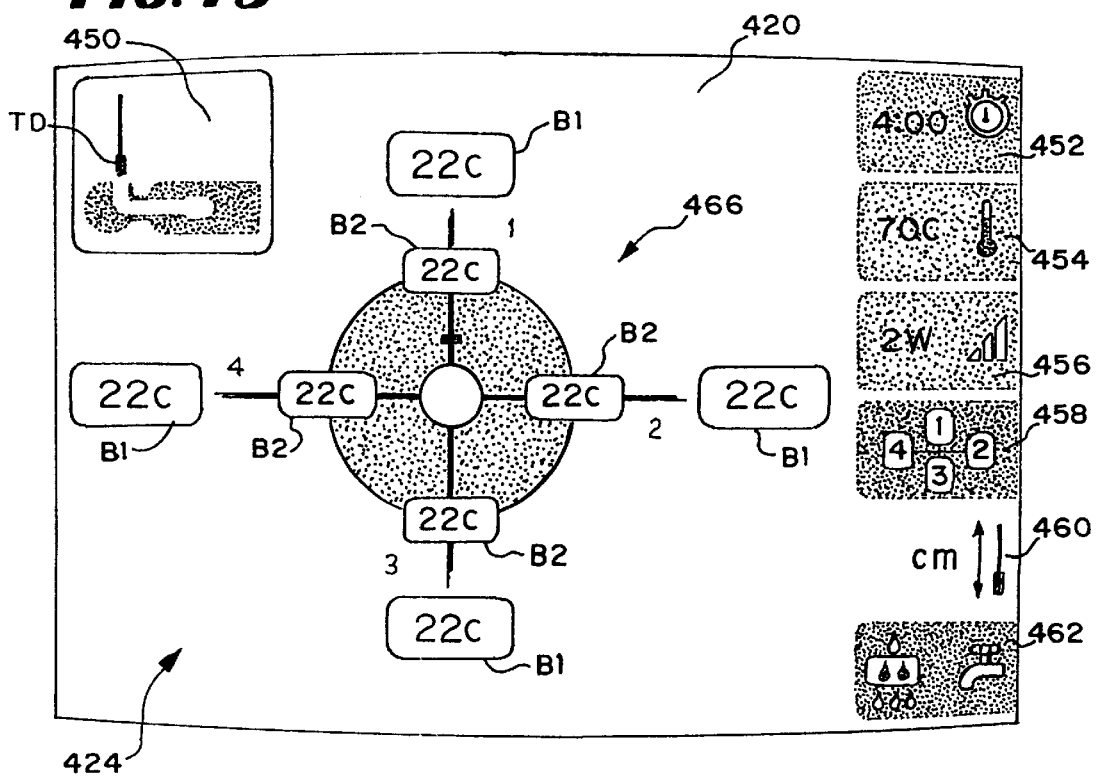
FIG. 75 is a view of the graphical user interface shown in FIG. 73 showing the Standby screen after connection of a treatment device.
Figure 78:
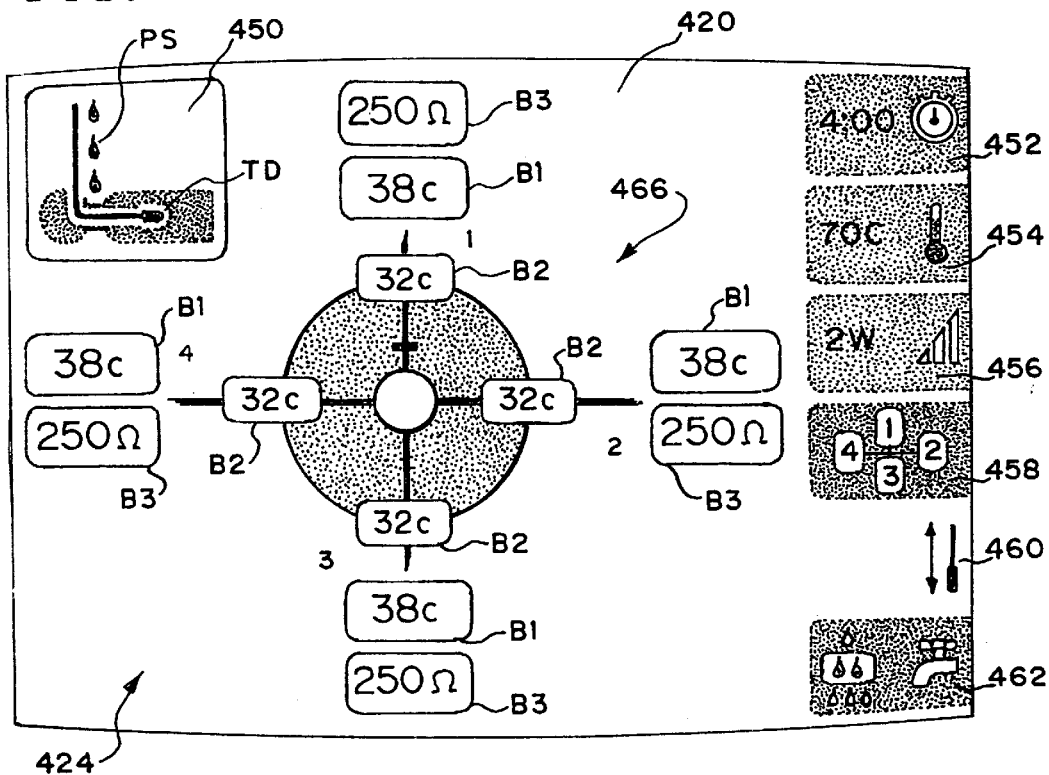
FIG. 78 is a view of the graphical user interface shown in FIG. 73 showing the Ready screen while priming of cooling liquid takes place.

The controller 52 prohibits advancement to the Ready screen until numeric values register in the boxes B1 and B2, as FIG. 75 shows. The display of numeric values indicate a functional treatment device TD.

No boxes B1 or B2 will appear in the Icon 466 for a given electrode if the corresponding electrode/channel has been disabled using the Channel Selection Keys 444, as FIG. 76 shows. In the illustrated embodiment, the physician is able to manually select or deselect individual electrodes using the Selection Keys 444 in the Standby or Ready Modes, but not in the RF-On Mode. However, the controller 52 can be configured to allow electrode selection while in the RF-On Mode, if desired.

While in the Standby Mode, the physician connects the treatment device TD to the device 400. The physician couples the source of cooling liquid to the appropriate port on the handle of the device TD (as previously described) and loads the tubing leading from the source of cooling liquid (e.g., a bag containing sterile water) in the pump rotor 428. The physician also couples the aspiration source to the appropriate port on the handle of the treatment device TD (as also already described). The physician also couples the patch electrode 412 and foot pedal 416. The physician can now deploy the treatment device TD to the targeted tissue region in the esophagus, in the manners previously described. The physician extends the electrodes through mucosal tissue and into underlying smooth muscle.

Once the treatment device TD is located at the desired location and the electrodes are deployed, the physician presses the Standby/Ready Button 430 to advance the device 400 from Standby to Ready Mode.

(iii) Ready

In the Ready Mode, the controller 52 commands the generator 38 to apply bursts of low level radio frequency energy through each electrode selected for operation. Based upon the transmission of these low level bursts of energy by each electrode, the controller 52 derives a local impedance value for each electrode. The impedance value indicates whether or nor the given electrode is in desired contact with submucosal, smooth muscle tissue. The use of impedance measurements for this purpose has been previously explained.

As FIG. 77 shows, the Ready screen updates the Screen Icon 450 to indicate that the treatment device TD is connected and deployed in the patient's esophagus. The Ready screen also intermittently blinks the RF On Indicator 434 to indicate that bursts of radio frequency energy are being applied by the electrodes. The Ready screen also updates the Electrode Icon 466 to spatially display in the inside and outside boxes B1 and B2 the actual sensed temperature conditions. The Ready screen also adds a further outside box B3 to spatially display the derived impedance value for each electrode.

On the Ready screen, instantaneous, sensed temperature readings from the tip electrode and tissue surface, as well as impedance values, are continuously displayed in spatial relation to the electrodes the boxes B1, B2, and B3 in the Electrode Icon 466. An "acceptable" color indicator (e.g., green) is also displayed in the background of box B1 as long as the tip temperature reading is within the desired pre-established temperature range (e.g., 15 to 120 C). However, if the tip temperature reading is outside the desired range, the color indicator changes to an "undesirable" color indicator (e.g., to white), and two dashes appear in box B1 instead of numeric values.

The controller 52 prevents the application of radio frequency energy if any temperature reading is outside a selected range (e.g., 15 to 120 degrees C).

The physician selects the "Up" key of the Flow Rate and Priming Keys 448 to operate the pump rotor 428 to prime the treatment device TD with cooling fluid. An animated droplet stream PS is displayed along the treatment device TD in the Icon 450, in the manner shown in FIG. 75, to indicate the delivery of cooling liquid by the pump rotor 428.

By touching the Target Duration Keys 438, the Target Temperature Keys 440, the Maximum Power Keys 442, the Channel Selection Keys 444, the Coagulation Level Keys 446, and the Flow Rate and Priming Keys 448, the physician can affect changes to the parameter values for the intended procedure. The controller 52 automatically adjusts to take these values into account in its control algorithms. The corresponding target duration icon 452, target temperature icon 454, maximum power icon 456, channel selection icon 458, coagulation level icon 460, and flow rate/priming icon 462 change accordingly to indicate the current selected parameter values.

When the physician is ready to apply energy to the targeted tissue region, the physician presses the foot pedal 416. In response, the device 400 advances from Ready to RF-On Mode, provided that all sensed temperatures are within the selected range.

(iv) RP-On

When the foot pedal 416 is pressed, the controller 52 activates the pump rotor 428. Cooling liquid is conveyed through the treatment device TD into contact with mucosal tissue at the targeted site. At the same time, cooling liquid is aspirated from the treatment device TD in an open loop. During a predetermined, preliminary time period (e.g. 2 to 5 seconds) while the flow of cooling liquid is established at the site, the controller 52 prevents the application of radio frequency energy.

Figure 79:
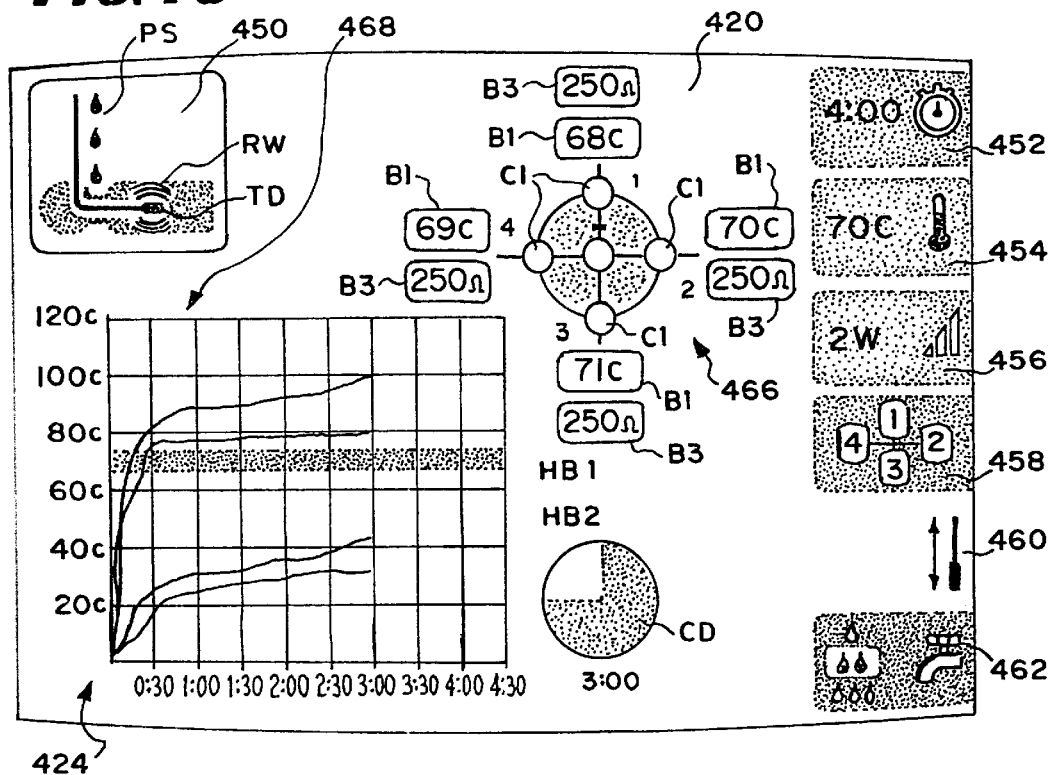
FIG. 79 is a view of the graphical user interface shown in FIG. 73 showing the RF-On screen.

After the preliminary time period, the controller 52 applies radio frequency energy through the electrodes. The RF-On screen, shown in FIG. 79, is displayed.

The RF-On screen displays the Screen Icon 450, indicate that the treatment device TD is connected and deployed in the patient's esophagus. The flow drop animation PS appears, indicating that cooling is taking place. A flashing radio wave animation RW also appears, indicating that radio frequency energy is being applied. The RF On Indicator 434 is also continuously illuminated to indicate that radio frequency energy is being applied by the electrodes.

The RF-On screen also updates the Electrode Icon 466 to display in the box B1 the actual sensed tip temperature conditions. The RF-On screen also displays the derived impedance value for each electrode in the boxes B3.

Unlike the Ready or Standby screens, the surface temperature is no longer displayed in a numerical format in a box B2. Instead, a circle C1 is displayed, which is color coded to indicate whether the surface temperature is less than the prescribed maximum (e.g., 45 degrees C). If the surface temperature is below the prescribed maximum, the circle is colored an "acceptable" color, e.g., green. If the surface temperature is exceeds the prescribed maximum, the color of the circle changes to an "not acceptable" color, e.g., to red.

Likewise, in addition to displaying numeric values, the boxes B1 and B3 are also color coded to indicate compliance with prescribed limits. If the tip temperature is below the prescribed maximum (e.g., 100 degrees C), the box B1 is colored, e.g., green. If the tip temperature is exceeds the prescribed maximum, the box border thickens and the color of the box B1 changes, e.g., to red. If the impedance is within prescribed bounds (e.g., between 25 ohms and 1000 ohms), the box B3 is colored, e.g., grey. If the impedance is outside the prescribed bounds, the box border thickens and the color of the box B3 changes, e.g., to red.

If desired, the Electrode Icon 466 can also display in a box or circle the power being applied to each electrode in spatial relation to the idealized image.

The RF-On screen displays the target duration icon 452, target temperature icon 454, maximum power icon 456, channel selection icon 458, coagulation level icon 460, and flow rate/priming icon 462, indicating the current selected parameter values. The physician can alter the target duration or target temperature or maximum power and pump flow rate through the corresponding selection keys 438, 440, 442, and 448 on the fly, and the controller 52 and GUI instantaneously adjust to the new parameter settings. As before mentioned, in the illustrated embodiment, the controller 52 does not permit change of the channel/electrode while radio frequency energy is being applied, and, for this reason, the channel selection icon 458 is dimmed.

Unlike the Standby and Ready screens, the RF-On screen also displays a real time line graph 468 to show changes to the temperature profile (Y-axis) over time (X-axis). The RF-On screen also shows a running clock icon 470, which changes appearance to count toward the target duration. In the illustrated embodiment, a digital clock display CD is also shown, indicating elapsed time.

The line graph 468 displays four trending lines to show the minimum and maximum surface and tip temperature readings from all active electrodes. In the illustrated embodiment, the time axis (X-axis) is scaled to one of five pre-set maximum durations, depending upon the set target duration. For example, if the target duration is 0 to 3 minutes, the maximum time scale is 3:30 minutes. If the target duration is 3 to 6 minutes, the maximum time scale is 6:30 seconds, and so on.

The line graph 468 displays two background horizontal bars HB1 and HB2 of different colors. The upper bar HB1 is colored, e.g., green, and is centered to the target coagulation temperature with a spread of plus and minus 10 degrees C. The lower bar HB2 is colored, e.g., red, and is fixed at a prescribed maximum (e.g., 40 degrees C) to alert potential surface overheating.

Figure 80:
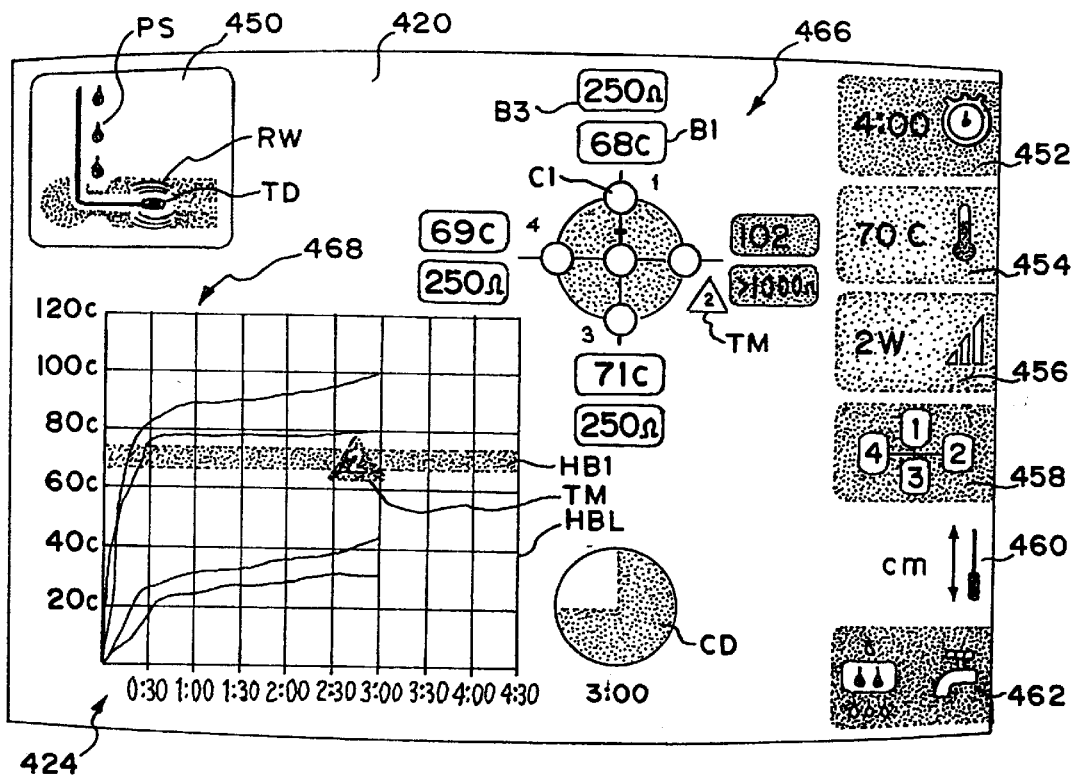
FIG. 80 is a view of the graphical user interface shown in FIG. 73 showing the RF-On screen after an electrode channel has been disabled due to an undesired operating condition.

The line graph 468 also displays a triangle marker TM of a selected color (e.g., red)(see FIG. 80) with a number corresponding to the channel/electrode that is automatically turned off by the controller 52 due to operation outside the selected parameters. As before described, the circle C1 and boxes B1 and B3 for this electrode/channel are also modified in the electrode icon 466 when this situation occurs.

The Electrode Icon 466 can graphically display other types of status or configuration information pertinent to the treatment device TD. For example, the Electrode Icon 466 can display a flashing animation in spatial relation to the idealized electrodes to constantly remind the physician that the electrode is extended into tissue. The flashing animation ceases to be shown when the electrode is retracted. The flashing animation reminds the physician to retract the electrodes before removing the treatment device TD. As another example, the Electrode Icon 466 can display another flashing animation when the expandable structure of the treatment device TD is expanded. The flashing animation reminds the physician to collapse the electrodes before removing the treatment device TD.

(v) Pause

Figure 81:
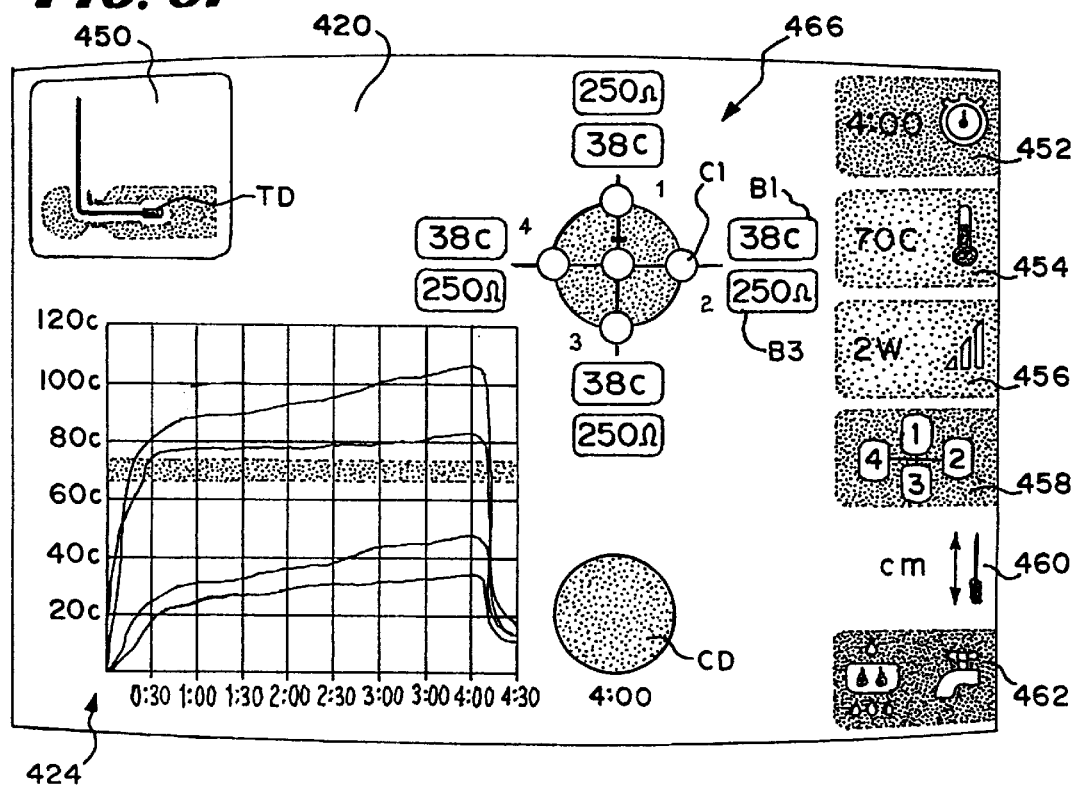
FIG. 81 is a view of the graphical user interface shown in FIG. 73 showing the Pause screen.

The controller 52 terminates the conveyance of radio frequency ablation energy to the electrodes and the RF-On screen changes into the Pause screen (see FIG. 81), due to any of the following conditions (i) target duration is reached, (ii) all channels/electrodes have an erroneous coagulation condition (electrode or surface temperature or impedance out of range), or (iii) manual termination of radio frequency energy application by pressing the foot pedal 416 or the Standby/Ready Button 430.

Upon termination of radio frequency ablation energy, the running clock icon 470 stops to indicate total elapsed time. The controller 52 commands the continued supply of cooling liquid through the treatment device TD into contact with mucosal tissue at the targeted site. At the same time, cooling liquid is aspirated from the treatment device TD in an open loop. This flow of cooling liquid continues for a predetermined time period (e.g. 2 to 5 seconds) after the supply of radio frequency ablation energy is terminated, after which the controller 52 stops the pump rotor 428.

During Pause, the controller 52 continues to supply intermittent bursts of low power radio frequency energy to acquire impedance information.

The Pause screen is in most respects similar to the RF-On screen. The Pause screen displays the Screen Icon 450, to indicate that the treatment device TD is connected and deployed in the patient's esophagus. The flashing radio wave animation is not present, indicating that radio frequency energy is no longer being applied. The RF On Indicator 434 is, however, intermittently illuminated to indicate that bursts of radio frequency energy are being applied by the electrodes to acquire impedance information.

The RF-On screen also updates the Electrode Icon 466 to display in the boxes B1 and B3 the actual sensed tip temperature and impedance conditions. However, no background color changes are registered on the Pause screen, regardless of whether the sensed conditions are without or outside the prescribed ranges.

The Pause screen continues to display the target duration icon 452, target temperature icon 454, maximum power icon 456, channel selection icon 458, coagulation level icon 460, and flow rate/priming icon 462, indicating the current selected parameter values.

The real time temperature line graph 468 continues to display the four trending lines, until the target duration is reached and five additional seconds elapse, to show the drop off of electrode temperature.

If further treatment is desired, pressing the Standby/Ready button 430 returns the device 400 from the Pause back to the Ready mode.

(vi) Procedure Log

As previously described, the floppy disk icon 464 and coagulation level icon 460 are normally dimmed on the various screens, until a floppy disk is inserted in the drive 426. When a floppy disk is inserted in the drive 426, the icons 460 and 464 are illuminated, and data is saved automatically after each application of radio frequency energy.

When the floppy disk is inserted, the controller 52 downloads data to the disk each time it leaves the RF-On screen, either by default or manual termination of the procedure. The downloaded data creates a procedure log. The log documents, by date of treatment and number of treatments, the coagulation level, the coagulation duration, energy delivered by each electrode, and the coolant flow rate. The procedure log also records at pre-established intervals (e.g., every 5 seconds) the temperatures of the electrode tips and surrounding tissue, impedance, and power delivered by each electrode. The procedure log preferably records these values in a spreadsheet format.

The housing 400 can carry an integrated printer, or can be coupled through the I/O device 54 to an external printer. The printer prints a procedure log in real time, as the procedure takes place.

Various features of the invention are set forth in the following claims.

We claim:

1. A device for association with an electrode structure which, in use, is deployed in a tissue region, the device comprising a housing, a generator integrated in the housing to generate energy capable of heating tissue and adapted to be coupled to the electrode structure to apply the energy to the tissue region, a pumping mechanism integrated in the housing and adapted to be attached to tubing to dispense cooling fluid from a source to the tissue region, a controller integrated in the housing and coupled to the generator and the pumping mechanism, to enable control of the generator in supplying energy to the electrode structure to raise tissue temperature in the tissue region, in concert with operation of the pumping mechanism in supplying cooling fluid to the tissue region to control the tissue temperature, a control panel on the housing supporting a consolidation of command input devices coupled to the controller, the command input devices including at least one generator control input for receiving from an operator an operating parameter affecting operation of the generator and at least one pump control input for receiving from an operator an operating parameter affecting operation of the pumping mechanism, and a display screen and an operating system coupled to the display screen to show an animated visual image indicating operation of the generator and an animated visual image indicating operation of the pumping mechanism.

2. A device according to claim 1 wherein the generator generates radio frequency energy.

3. A device according to claim 1 wherein the pumping mechanism includes a peristaltic pump rotor.

4. A device for association with an electrode structure which, in use, is deployed in a tissue region, the device comprising a housing, a generator integrated in the housing to generate energy capable of heating tissue and adapted to be coupled to the electrode structure to apply the energy to the tissue region, a pumping mechanism integrated in the housing and adapted to be attached to tubing to dispense cooling fluid from a source to the tissue region, a controller integrated in the housing and coupled to the generator and the pumping mechanism, to enable control of the generator in supplying energy to the electrode structure to raise tissue temperature in the tissue region, in concert with operation of the pumping mechanism in supplying cooling fluid to the tissue region to control the tissue temperature, a control panel on the housing supporting a consolidation of command input devices coupled to the controller, the command input devices including at least one generator control input for receiving from an operator an operating parameter affecting operation of the generator and at least one pump control input for receiving from an operator an operating parameter affecting operation of the pumping mechanism, and a display screen coupled to the controller, the controller including an operating system that generates a first image on the display screen that represents an operating condition of the generator, the operating system also generating a second image on the display screen concurrently with the first image that represents an operating condition of the pumping mechanism.

5. A device according to claim 4 wherein the pumping mechanism includes a peristaltic pump rotor.

6. A device according to claim 4 wherein the controller includes a pump drive function to monitor pumping rate of the pumping mechanism.

7. A device according to claim 4 wherein the controller includes a pump drive function to select a pumping rate for the pumping mechanism.

8. A device according to claim 4 wherein the controller enables manual control of the operation of the generator.

9. A device according to claim 4 wherein the controller enables automatic control of the operation of the generator.

10. A device according to claim 4 wherein the controller enables manual control of the operation of the pumping mechanism.

11. A device according to claim 4 wherein the controller enables automatic control of the operation of the pumping mechanism.

12. A device according to claim 4 wherein the first image changes according to operation of the generator.

13. A device according to claim 4 wherein the second image changes according to operation of the pumping mechanism.

14. A device according to claim 4 wherein the operating system generates an image of an electrode structure on the display screen.

15. A device according to claim 4 wherein the controller includes an input adapted to be attached to a sensor in the tissue region to monitor an operating condition in concert with operation of the generator and pumping mechanism.

16. A device according to claim 15 wherein the operating system generates an image on the display screen that represents the operation condition monitored by the sensor.

17. A device according to claim 15 wherein the operating system generates an image on the display screen that represents changes in the operating condition monitored by the sensor over time.

18. A device according to claim 15 wherein the operating system generates an image on the display screen of an electrode structure in association with an image that represents the operation condition monitored by the sensor.

19. A device according to claim 15 wherein the controller includes a feed-back function to vary operation of the generator according to the operating condition monitored by the sensor.

20. A device according to claim 15 wherein the controller includes a feed-back function to vary operation of the pumping mechanism according to the operating condition monitored by the sensor.

21. A device according to claim 15 wherein the sensor monitors tissue temperature conditions.

22. A device according to claim 4 further including an aspiration module adapted to be attached to tubing to remove cooling liquid from the tissue region.

23. A device according to claim 22 wherein the aspiration module is integrated in the housing.

24. A device according to claim 22 wherein the aspiration module includes an external vacuum source.

25. A device according to claim 4 wherein the generator generates radio frequency energy.

26. A device for association with an electrode structure which, in use, is deployed in a tissue region and which includes an electrode having a distal end that, in use, penetrates tissue in the tissue region, the device comprising
a housing,
a generator integrated in the housing to generate energy capable of heating tissue and adapted to be coupled to the electrode structure to apply the energy to the tissue region,
a pumping mechanism integrated in the housing and adapted to be attached to tubing to dispense cooling fluid from a source to the tissue region,
a controller integrated in the housing and including a first temperature sensor adapted to be carried by the electrode structure to monitor surface tissue temperature and a second temperature sensor adapted to be carried by the distal end of the electrode to monitor subsurface tissue temperature, the controller also including an input adapted to be attached to the first and second temperature sensors, and a function responsive to monitored surface tissue temperature, or monitored subsurface tissue temperature, or both, to control operation of the generator in concert with operation of the pumping mechanism, to thereby enable command of the generator and the pumping mechanism to controllably heat tissue in the tissue region,
a control panel on the housing supporting a consolidation of command input devices coupled to the controller, the command input devices including at least one generator control input for receiving from an operator an operating parameter affecting operation of the generator and at least one pump control input for receiving from an operator an operating parameter affecting operation of the pumping mechanism, and
a display screen coupled to the controller, the controller including an operating system that generates a first image on the display screen that represents an operating condition of the generator, the operating system also generating a second image on the display screen concurrently with the first image that represents an operating condition of the pumping mechanism.

27. A device according to claim 26 wherein the pumping mechanism includes a peristaltic pump rotor.

28. A device according to claim 26 wherein the controller includes a pump drive function to monitor pumping rate of the pumping mechanism.

29. A device according to claim 26 wherein the controller includes a pump drive function to select a pumping rate for the pumping mechanism.

30. A device according to claim 26 wherein the controller enables manual control of the operation of the generator.

31. A device according to claim 26 wherein the controller enables automatic control of the operation of the generator in response to monitored surface tissue temperature, or monitored subsurface tissue temperature, or both.

32. A device according to claim 26 wherein the controller enables manual control of the operation of the pumping mechanism.

33. A device according to claim 26 wherein the device enables automatic control of the operation of the pumping mechanism in response to monitored surface tissue temperature, or monitored subsurface tissue temperature, or both.

34. A device according to claim 26 wherein the first image changes according to operation of the generator.

35. A device according to claim 26 wherein the second image changes according to operation of the pumping mechanism.

36. A device according to claim 26 wherein the operating system generates an image of an electrode structure on the display screen.

37. A device according to claim 26 wherein the operating system generates an image on the display screen that represents monitored surface tissue temperature, or monitored subsurface tissue temperature, or both.

38. A device according to claim 26 wherein the operating system generates an image on the display screen that represents changes to monitored surface tissue temperature, or monitored subsurface tissue temperature, or both over time.

39. A device according to claim 26 wherein the operating system generates on the display screen a viewable image comprising an idealized image of the distal end of the electrode in spatial relation to an idealized image of the support structure, the viewable image including an indication of the monitored surface tissue temperature shown in spatial association with the idealized image of the support structure and an indication of the monitored subsurface tissue temperature shown in spatial association with the idealized image of the distal end of the electrode.

40. A device according to claim 26 further including an aspiration module adapted to be attached to tubing to remove cooling liquid from the tissue region.

41. A device according to claim 40 wherein the aspiration module is integrated in the housing.

42. A device according to claim 40 wherein the aspiration module includes an external vacuum source.

43. A device according to claim 26 wherein the generator generates radio frequency energy.

44. A device for association with an electrode structure which, in use, is deployed in a tissue region, the device comprising a housing, a generator integrated in the housing to generate energy capable of heating tissue and adapted to be coupled to the electrode structure to apply the energy to the tissue region, a pumping mechanism integrated in the housing and adapted to be attached to tubing to dispense cooling fluid from a source to the tissue region, and a controller integrated in the housing and coupled to the generator and the pumping mechanism, the controller including an ON input to command application of energy to the electrode structure and a function that, in response to the ON input, commences operation of the pumping mechanism for a prescribed time period while delaying operation of the generator until the prescribed time period lapses, a control panel on the housing supporting a consolidation of command input devices coupled to the controller, the command input devices including at least one generator control input for receiving from an operator an operating parameter affecting operation of the generator and at least one pump control input for receiving from an operator an operating parameter affecting operation of the pumping mechanism, and a display screen coupled to the controller, the controller including an operating system that generates a first image on the display screen that represents an operating condition of the generator, the operating system also generating a second image on the display screen concurrently with the first image that represents an operating condition of the pumping mechanism.

45. A device for association with an electrode structure which, in use, is deployed in a tissue region, the device comprising a housing, a generator integrated in the housing to generate energy capable of heating tissue and adapted to be coupled to the electrode structure to apply the energy to the tissue region, a pumping mechanism integrated in the housing and adapted to be attached to tubing to dispense cooling fluid from a source to the tissue region, and a controller integrated in the housing and coupled to the generator and the pumping mechanism, the controller including an OFF input to command termination of the application of energy to the electrode structure and a function that, in response to the OFF input, operates the pumping mechanism for a prescribed time period after the supply of energy is terminated, a control panel on the housing supporting a consolidation of command input devices coupled to the controller, the command input devices including at least one generator control input for receiving from an operator an operating parameter affecting operation of the generator and at least one pump control input for receiving from an operator an operating parameter affecting operation of the pumping mechanism, and a display screen coupled to the controller, the controller including an operating system that generates a first image on the display screen that represents an operating condition of the generator, the operating system also generating a second image on the display screen concurrently with the first image that represents an operating condition of the pumping mechanism.

46. A device according to claim 44 or 45 wherein the generator generates radio frequency energy.

47. A device according to claim 44 or 45 wherein the pumping mechanism includes a peristaltic pump rotor.

48. A device for association with an electrode structure which, in use, is deployed in a tissue region, the device comprising a housing, a generator integrated in the housing to generate energy capable of heating tissue and adapted to be coupled to the electrode structure to apply the energy to the tissue region, a pumping mechanism integrated in the housing and adapted to be attached to tubing to dispense cooling fluid from a source to the tissue region, and a controller integrated in the housing and coupled to the generator and the pumping mechanism, the controller including an ON input to command application of energy to the electrode structure in concert with operation of the pumping mechanism and an OFF input to command termination of the application of energy to the electrode structure, the controller further including a display screen and an operating system coupled to the display screen to generate, after the ON input, an ON image comprising a time record of changes in at least one operating condition over time during operation of the generator and the pumping mechanism and, after the OFF input, a PAUSE image that preserves the time record.

49. A device according to claim 48 wherein the PAUSE image updates the time record according to changes in the operating condition after the OFF input.

50. A device according to claim 48 wherein the controller includes a function that, in response to the ON input, commences operation of the pumping mechanism for a prescribed time period while delaying operation of the generator until the prescribed time period lapses.

51. A device according to claim 48 wherein the controller includes and a function that, in response to the OFF input, operates the pumping mechanism for a prescribed time period after the supply of energy is terminated.

52. A device according to claim 51 wherein the PAUSE image updates the time record according to changes in the operating condition after the OFF input.

* * * * *